United States Patent
Utsumi et al.

(10) Patent No.: US 8,268,530 B2
(45) Date of Patent: Sep. 18, 2012

(54) POSITIVE RESIST COMPOSITION, METHOD OF FORMING RESIST PATTERN, POLYMERIC COMPOUND, AND COMPOUND

(75) Inventors: Yoshiyuki Utsumi, Kawasaki (JP); Jun Iwashita, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 339 days.

(21) Appl. No.: 12/762,715

(22) Filed: Apr. 19, 2010

(65) Prior Publication Data

US 2010/0273106 A1    Oct. 28, 2010

(51) Int. Cl.
- C08F 24/00 (2006.01)
- C08F 34/02 (2006.01)
- G03C 1/00 (2006.01)
- G03F 7/00 (2006.01)
- G03F 1/00 (2006.01)

(52) U.S. Cl. ............ 430/270.1; 430/326; 526/268; 526/270

(58) Field of Classification Search .......... 430/270.1, 430/326; 526/268, 270; 549/434
See application file for complete search history.

(56) References Cited

U.S. PATENT DOCUMENTS

| | | | |
|---|---|---|---|
| 5,945,517 A | 8/1999 | Nitta et al. | |
| 6,153,733 A | 11/2000 | Yukawa et al. | |
| 7,074,543 B2 | 7/2006 | Iwai et al. | |

FOREIGN PATENT DOCUMENTS

| | | |
|---|---|---|
| JP | H09-208554 | 8/1997 |
| JP | H11-035551 | 2/1999 |
| JP | H11-035552 | 2/1999 |
| JP | H11-035573 | 2/1999 |
| JP | H11-322707 | 11/1999 |
| JP | 2003-241385 | 8/2003 |
| WO | WO 2004/074242 | 9/2004 |

*Primary Examiner* — Cynthia Kelly
*Assistant Examiner* — Connie P Johnson
(74) *Attorney, Agent, or Firm* — Knobbe Martens Olson & Bear LLP

(57) ABSTRACT

A positive resist composition including a base component (A) which exhibits increased solubility in an alkali developing solution under the action of acid and an acid generator component (B) which generates acid upon exposure, wherein the base component (A) includes a polymeric compound (A1) having a structural unit (a0) containing an acid-dissociable, dissolution-inhibiting group, and the acid-dissociable, dissolution-inhibiting group has a 1,3-dioxole skeleton.

12 Claims, No Drawings

US 8,268,530 B2

POSITIVE RESIST COMPOSITION, METHOD OF FORMING RESIST PATTERN, POLYMERIC COMPOUND, AND COMPOUND

TECHNICAL FIELD

The present invention relates to a positive resist composition, a polymeric compound which can be used as a base component for the positive resist composition, a compound that can be used for synthesizing the polymeric compound, and a method of forming a resist pattern using the positive resist composition.

Priority is claimed on Japanese Patent Application No. 2009-106711, filed Apr. 24, 2009, the content of which is incorporated herein by reference.

BACKGROUND ART

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film.

A resist material in which the exposed portions of the resist film become soluble in a developing solution is called a positive-type, and a resist material in which the exposed portions of the resist film become insoluble in a developing solution is called a negative-type.

In recent years, in the production of semiconductor elements and liquid crystal display elements, advances in lithography techniques have lead to rapid progress in the field of pattern miniaturization.

Typically, these miniaturization techniques involve shortening the wavelength (and increasing the energy) of the exposure light source. Conventionally, ultraviolet radiation typified by g-line and i-line radiation has been used, but nowadays KrF excimer lasers and ArF excimer lasers are starting to be introduced in mass production. Furthermore, research is also being conducted into lithography techniques that use an exposure light source having a shorter wavelength (and a higher energy level) than these excimer lasers, such as an electron beam, extreme ultraviolet radiation (EUV), and X-ray.

Resist materials for use with these types of exposure light sources require lithography properties such as a high resolution capable of reproducing patterns of minute dimensions, and a high level of sensitivity to these types of exposure light sources.

As a resist material that satisfies these conditions, a chemically amplified resist composition is used, which includes a base material component that exhibits changed solubility in an alkali developing solution under the action of acid, and an acid generator that generates acid upon exposure.

For example, a chemically amplified positive resist typically contains a resin component (base resin) that exhibits increased solubility in an alkali developing solution under the action of acid, and an acid generator component. If the resist film formed using the resist composition is selectively exposed during formation of a resist pattern, then within the exposed portions, acid is generated from the acid generator, and the action of this acid causes an increase in the solubility of the resin component in an alkali developing solution, making the exposed portions soluble in the alkali developing solution.

Currently, resins that contain structural units derived from (meth)acrylate esters within the main chain (acrylic resins) are widely used as base resins for resists that use ArF excimer laser lithography, as they exhibit excellent transparency in the vicinity of 193 nm (for example, see Patent Document 1).

Here, the term "(meth)acrylic acid" is a generic term that includes either or both of acrylic acid having a hydrogen atom bonded to the α-position and methacrylic acid having a methyl group bonded to the α-position. The term "(meth)acrylate ester" is a generic term that includes either or both of the acrylate ester having a hydrogen atom bonded to the α-position and the methacrylate ester having a methyl group bonded to the α-position. The term "(meth)acrylate" is a generic term that includes either or both of the acrylate having a hydrogen atom bonded to the α-position and the methacrylate having a methyl group bonded to the α-position.

Further, in order to improve various lithography properties, a base resin having a plurality of structural units is currently used for a chemically amplified resist. For example, in the case of a positive resist, a base resin containing a structural unit having an acid-dissociable, dissolution-inhibiting group that is dissociated by the action of acid generated from the acid generator, a structural unit having a polar group such as a hydroxyl group, and a structural unit having a lactone structure and the like is typically used. Among these structural units, a structural unit having a lactone structure is generally considered as being effective in improving the adhesion between the resist film and the substrate, and increasing the compatibility with an alkali developing solution, thereby contributing to improvement in various lithography properties.

[Patent Document 1] Japanese Unexamined Patent Application, First Publication No. 2003-241385

SUMMARY OF THE INVENTION

Problems to be Solved by the Invention

As further progress is made in lithography techniques and the application field for lithography techniques expands, the development of novel materials for use in lithography applications will be desirable.

In particular, as the miniaturization of resist patterns progresses, there is a possibility that because of problems such as low rectangularity of the cross-sectional shape of the resist pattern and significant levels of line width roughness (LWR), conventional resist materials may have adverse effects on the formation of very fine semiconductor elements and the like.

In this description, LWR refers to a phenomenon in which pattern surface roughness occurs during the formation of a resist pattern using a resist composition, resulting in a lack of uniformity in the line widths of a line pattern.

Accordingly, as resist patterns have become increasingly finer, the requirements that the resist material provides high resolution, exhibits excellent lithography properties such as LWR, and is capable of forming a resist pattern of favorable shape have become more important than is currently the case.

The present invention has been developed in light of the above circumstances, and has an object of providing a positive resist composition that is capable of forming a resist pattern of favorable shape that exhibits excellent resolution and reduced line width roughness (LWR), as well as providing a polymeric compound that can be used as the base component of this positive resist composition, a compound that can be used in synthesizing the polymeric compound, and a method of forming a resist pattern.

Means to Solve the Problems

In order to achieve the above-mentioned object, the present invention employs the following aspects.

Specifically, a first aspect of the present invention is a positive resist composition including a base component (A) which exhibits increased solubility in an alkali developing solution under the action of acid, and an acid generator component (B) which generates acid upon exposure, wherein the base component (A) includes a polymeric compound (A1) having a structural unit (a0) containing an acid-dissociable, dissolution-inhibiting group, and the acid-dissociable, dissolution-inhibiting group has a 1,3-dioxole skeleton.

A second aspect of the present invention is a method of forming a resist pattern, including applying a positive resist composition according to the first aspect onto a substrate to form a resist film, subjecting the resist film to exposure, and subjecting the resist film to alkali developing to form a resist pattern.

A third aspect of the present invention is a polymeric compound including a structural unit represented by general formula (a0-1') shown below.

[Chemical Formula 1]

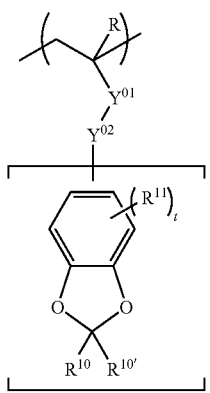

(a0-1')

In formula (a0-1'), R represents a hydrogen atom, an alkyl group of 1 to 5 carbon atoms or a halogenated alkyl group of 1 to 5 carbon atoms, $Y^{01}$ represents a divalent organic group that becomes an alkali-soluble group upon cleavage of the bond to $Y^{02}$ under the action of acid, $Y^{02}$ represents a single bond or a divalent linking group, which substitutes one of the hydrogen atoms of the group within the brackets [ ] of formula (a0-1') that is derived from either a 1,3-benzodioxole or a derivative thereof, $R^{11}$ represents a hydrocarbon group of 1 to 30 carbon atoms which may have a substituent, t represents an integer of 0 to 3, and in those cases where t is 2 or 3, a plurality of $R^{11}$ groups may be bonded together to form a ring, or may be bonded to the benzene ring to form an aromatic ring, $R^{10}$ represents a hydrogen atom or an alkyl group of 1 to 5 carbon atoms which may have a substituent, $R^{10'}$ represents a hydrogen atom or an alkyl group of 1 to 5 carbon atoms which may have a substituent, and $R^{10}$ and $R^{10'}$ may be bonded together to form a ring.

A fourth aspect of the present invention provides a compound represented by general formula (a0-1-1) shown below.

[Chemical Formula 2]

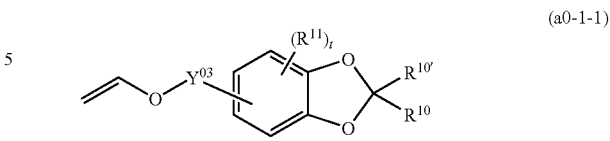

(a0-1-1)

In formula (a0-1-1), $Y^{03}$ represents a single bond or a divalent linking group, $R^{11}$ represents a hydrocarbon group of 1 to 30 carbon atoms which may have a substituent, t represents an integer of 0 to 3, and in those cases where t is 2 or 3, a plurality of $R^{11}$ groups may be bonded together to form a ring, or may be bonded to the benzene ring to form an aromatic ring, $R^{10}$ represents a hydrogen atom or an alkyl group of 1 to 5 carbon atoms which may have a substituent, $R^{10'}$ represents a hydrogen atom or an alkyl group of 1 to 5 carbon atoms which may have a substituent, and $R^{10}$ and $R^{10'}$ may be bonded together to form a ring.

A fifth aspect of the present invention is a compound represented by general formula (a0-1-1-1) shown below.

[Chemical Formula 3]

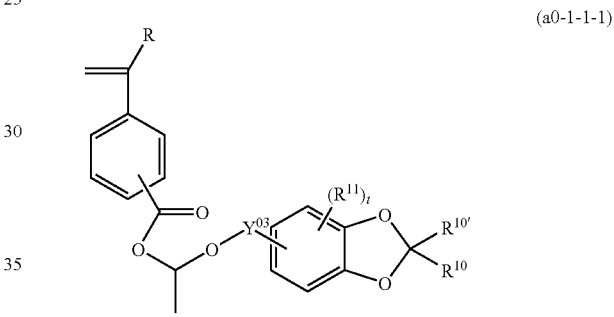

(a0-1-1-1)

In formula (a0-1-1-1), R represents a hydrogen atom, an alkyl group of 1 to 5 carbon atoms or a halogenated alkyl group of 1 to 5 carbon atoms, $Y^{03}$ represents a single bond or a divalent linking group, $R^{11}$ represents a hydrocarbon group of 1 to 30 carbon atoms which may have a substituent, t represents an integer of 0 to 3, and in those cases where t is 2 or 3, a plurality of $R^{11}$ groups may be bonded together to form a ring, or may be bonded to the benzene ring to form an aromatic ring, $R^{10}$ represents a hydrogen atom or an alkyl group of 1 to 5 carbon atoms which may have a substituent, $R^{10'}$ represents a hydrogen atom or an alkyl group of 1 to 5 carbon atoms which may have a substituent, and $R^{10}$ and $R^{10'}$ may be bonded together to form a ring.

In the present description and claims, the term "alkyl group" includes linear, branched and cyclic monovalent saturated hydrocarbon groups, unless otherwise specified.

The term "alkylene group" includes linear, branched and cyclic divalent saturated hydrocarbon groups, unless otherwise specified.

A "lower alkyl group" describes an alkyl group of 1 to 5 carbon atoms.

A "halogenated alkyl group" is a group in which part or all of the hydrogen atoms of an alkyl group have been substituted with halogen atoms. Examples of the halogen atoms include fluorine atoms, chlorine atoms, bromine atoms and iodine atoms.

The term "aliphatic" is a relative concept used in relation to the term "aromatic", and defines a group or compound or the like that has no aromaticity.

The term "structural unit" refers to a monomer unit that contributes to the formation of a polymeric compound (polymer or copolymer).

The term "exposure" is used as a general concept that includes irradiation with any form of radiation.

Effect of the Invention

According to the present invention, there are provided a positive resist composition that is capable of forming a resist pattern of favorable shape that exhibits excellent resolution and reduced line width roughness (LWR), a polymeric compound that can be used as the base component for the positive resist composition, a compound that can be used in synthesizing the polymeric compound, and a method of forming a resist pattern.

DETAILED DESCRIPTION OF THE INVENTION

<<Positive Resist Composition>>

The positive resist composition of the first aspect of the present invention includes a base component (A) (hereafter, referred to as "component (A)") which exhibits increased solubility in an alkali developing solution under the action of acid, and an acid generator component (B) (hereafter, referred to as "component (B)") which generates acid upon exposure.

In the positive resist composition, the component (A) is insoluble in an alkali developing solution prior to exposure, but the action of the acid generated from the component (B) upon exposure increases the solubility in an alkali developing solution of the entire component (A), so that the component (A) changes from an alkali-insoluble state to an alkali-soluble state. Accordingly, during the formation of a resist pattern, by conducting selective exposure of a resist film formed using the positive resist composition, the exposed portions of the resist film become alkali-soluble, whereas the unexposed portions remain alkali-insoluble, and therefore a resist pattern can be formed by alkali developing.

The positive resist composition of the present invention may also include a nitrogen-containing organic compound component (D).

<Component (A)>

In the present invention, the term "base component" refers to an organic compound capable of forming a film.

As the base component, an organic compound having a molecular weight of 500 or more can be preferably used. When the organic compound has a molecular weight of 500 or more, the film-forming ability is improved, and a nano level resist pattern can be easily formed.

The "organic compound having a molecular weight of 500 or more" which can be used as a base component is broadly classified into non-polymers and polymers.

In general, as a non-polymer, any of those compounds which have a molecular weight in the range of 500 to less than 4,000 may be used. Hereafter, a non-polymer having a molecular weight in the range of 500 to less than 4,000 is referred to as a "low molecular weight compound".

As a polymer, any of those compounds which have a molecular weight of 1,000 or more may be used. Hereafter, a polymer having a molecular weight of 1,000 or more is referred to as a "polymeric compound". In the case of a polymeric compound, the "molecular weight" is the weight average molecular weight in terms of the polystyrene equivalent value determined by gel permeation chromatography (GPC). Hereafter, a polymeric compound is frequently referred to as simply a "resin".

In the present invention, the component (A) includes a polymeric compound (A1) (hereafter, referred to as "component (A1)") having a structural unit (a0) containing an acid-dissociable, dissolution-inhibiting group.

Further, the component (A) may also include, in addition to the component (A1), a low molecular weight compound component (A2) (hereafter, referred to as "component (A2)") that exhibits increased solubility in an alkali developing solution under the action of acid.

[Component (A1)]

The component (A1) is a polymeric compound having a structural unit (a0) containing an acid-dissociable, dissolution-inhibiting group, wherein the acid-dissociable, dissolution-inhibiting group has a 1,3-dioxole skeleton.

As the component (A1), one type of polymeric compound may be used alone, or two or more types of polymeric compounds may be used in combination.

In the positive resist composition of the present invention, it is preferable that in addition to the structural unit (a0) containing an "acid-dissociable, dissolution-inhibiting group having a 1,3-dioxole skeleton", the component (A1) also includes a structural unit (a5) derived from a hydroxystyrene.

Further, the component (A1) may also include structural units other than the structural unit (a0) and the structural unit (a5), either in addition to the structural unit (a0), or in addition to the structural unit (a0) and the structural unit (a5).

Structural Unit (a0)

The structural unit (a0) is a structural unit containing an "acid-dissociable, dissolution-inhibiting group having a 1,3-dioxole skeleton".

In the present description and claims, a "1,3-dioxole skeleton" describes a structure represented by a chemical formula shown below. In the formula below, each of the carbon atoms $C^a$, $C^b$ and $C^c$ is bonded to another atom or group. The term "1,3-dioxole skeleton", also includes those structures in which the carbon atoms $C^a$ and $C^b$ are bonded to other atoms or groups to form a resonance structure.

[Chemical Formula 4]

The acid-dissociable, dissolution-inhibiting group within the structural unit (a0) has an alkali dissolution-inhibiting effect that renders the entire component (A1) substantially insoluble in an alkali developing solution prior to dissociation, but then dissociates under the action of acid, thereby increasing the solubility of the entire component (A1) in the alkali developing solution. Examples of the acid-dissociable, dissolution-inhibiting group include groups that substitute the hydrogen atom within a phenolic hydroxyl group (—OH), a thiol group (—SH) or a carboxyl group (—C(=O)—OH) or the like, namely, groups that protect an alkali-soluble group. Typical examples of these groups that protect an alkali-soluble group include groups that form a cyclic or chain-like tertiary alkyl ester with the alkali-soluble group, and acetal-type acid-dissociable, dissolution-inhibiting groups such as alkoxyalkyl groups.

Here, a "tertiary alkyl ester" describes a structure in which an ester is formed by substituting the hydrogen atom of an aforementioned alkali-soluble group with a chain-like or cyclic tertiary alkyl group, and a tertiary carbon atom within the chain-like or cyclic tertiary alkyl group is bonded to the atom within the alkali-soluble group to which the hydrogen atom was originally bonded (such as an oxygen atom or sulfur atom). In this tertiary alkyl ester, the action of acid causes cleavage of the bond between the atom within the alkali-soluble group to which the hydrogen atom was originally bonded (such as an oxygen atom or sulfur atom) and the tertiary carbon atom.

The chain-like or cyclic alkyl group may have a substituent.

Hereafter, for the sake of simplicity, groups that exhibit acid dissociability as a result of the formation of a tertiary alkyl ester with the atom within an alkali-soluble group to which the hydrogen atom was originally bonded are referred to as "tertiary alkyl ester-type acid-dissociable, dissolution-inhibiting groups".

An "acetal-type acid-dissociable, dissolution-inhibiting group" is bonded to the atom within an aforementioned alkali-soluble group to which the hydrogen atom was originally bonded (such as an oxygen atom or sulfur atom). When acid is generated upon exposure, the generated acid acts to break the bond between the acetal-type acid-dissociable, dissolution-inhibiting group and the atom within the alkali-soluble group to which the acetal-type, acid-dissociable, dissolution-inhibiting group is bonded and to which the hydrogen atom was originally bonded.

Examples of the acetal-type acid-dissociable, dissolution-inhibiting group within the structural unit (a0) include acid-dissociable, dissolution-inhibiting groups (p11) represented by general formula (p11) shown below.

[Chemical Formula 5]

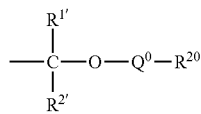

(p11)

In the formula, each of $R^{1'}$ and $R^{2'}$ independently represents a hydrogen atom or an alkyl group of 1 to 5 carbon atoms, $Q^0$ represents a single bond or a divalent linking group, and represents an organic group having a 1,3-dioxole skeleton.

In formula (p11) above, examples of the alkyl groups for $R^{1'}$ and $R^{2'}$ include the same alkyl groups as those described above for R, although a methyl group or ethyl group is preferable, and a methyl group is the most desirable.

In the present invention, it is preferable that at least one of $R^{1'}$ and $R^{2'}$ is a hydrogen atom. In other words, it is preferable that the acid-dissociable, dissolution-inhibiting group (p11) is a group represented by general formula (p11-1) shown below.

[Chemical Formula 6]

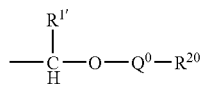

(p11-1)

In the formula, $R^{1'}$, $Q^0$ and $R^{20}$ are the same as defined above.

In formula (p11) and (p11-1), $Q^0$ represents a single bond or a divalent linking group.

Examples of the divalent linking group for $Q^0$ include alkylene groups, divalent aliphatic cyclic groups, and divalent linking groups containing a hetero atom.

The "aliphatic cyclic group" for $Q^0$ refers to a monocyclic group or polycyclic group that has no aromaticity.

The "aliphatic cyclic group" for $Q^0$ may or may not have a substituent. Examples of the substituent include an alkyl group of 1 to 5 carbon atoms, an alkoxy group of 1 to 5 carbon atoms, a fluorine atom, a fluorinated alkyl group of 1 to 5 carbon atoms, and an oxygen atom (=O) or the like.

The basic ring structure of the "aliphatic cyclic group" exclusive of substituents is not limited to groups constituted solely from carbon and hydrogen (not limited to hydrocarbon groups), but is preferably a hydrocarbon group. Further, the "hydrocarbon group" may be either saturated or unsaturated, but is preferably saturated. Furthermore, the "aliphatic cyclic group" is preferably a polycyclic group. The aliphatic cyclic group preferably contains 3 to 20 carbon atoms, and more preferably 3 to 12 carbon atoms.

Examples of such aliphatic cyclic groups include groups in which two or more hydrogen atoms have been removed from a monocycloalkane or a polycycloalkane such as a bicycloalkane, tricycloalkane or tetracycloalkane, which may or may not be substituted with a lower alkyl group, a fluorine atom or a fluorinated alkyl group. Specific examples include groups in which two or more hydrogen atoms have been removed from a monocycloalkane such as cyclopentane or cyclohexane, or a polycycloalkane such as adamantane, norbornane, isobornane, tricyclodecane or tetracyclododecane.

Of the above groups, in those cases where $Q^0$ is a divalent aliphatic cyclic group, a group in which two or more hydrogen atom have been removed from cyclopentane, cyclohexane, norbornane, isobornane, adamantane, tricyclodecane or tetracyclododecane is particularly desirable.

In those cases where $Q^0$ represents an alkylene group, the alkylene group preferably contains 1 to 10 carbon atoms, more preferably 1 to 6 carbon atoms, still more preferably 1 to 4 carbon atoms, and most preferably 1 to 3 carbon atoms.

In those cases where $Q^0$ represents a divalent linking group containing a hetero atom, examples of the divalent linking group containing a hetero atom include —O—, —C(=O)—O—, —C(=O)—, —O—C(=O)—O—, —C(=O)—NH—, —NH— (wherein H may be replaced with a substituent such as an alkyl group or acyl group or the like), —S—, —S(=O)$_2$—O—, -A-O (oxygen atom)-B—, -A-O—C(=O)—B—, and -A-O—C(=O)—, wherein each of A and B independently represents a divalent hydrocarbon group which may have a substituent.

When $Q^0$ represents —NH—, the substituent (such as an alkyl group or acyl group or the like) that may replace the H preferably has 1 to 10 carbon atoms, more preferably 1 to 8 carbon atoms, and most preferably 1 to 5 carbon atoms.

In those cases where $Q^0$ represents -A-O (oxygen atom)-B—, -A-O—C(=O)—B— or -A-O—C(=O)—, each of A and B independently represents a divalent hydrocarbon group which may have a substituent.

The expression that the hydrocarbon group "may have a substituent" means that part or all of the hydrogen atoms within the hydrocarbon group may be substituted with groups or atoms other than hydrogen atoms.

The hydrocarbon group for A may be either an aliphatic hydrocarbon group or an aromatic hydrocarbon group. An "aliphatic hydrocarbon group" describes a hydrocarbon group that has no aromaticity.

The aliphatic hydrocarbon group for A may be saturated or unsaturated, but is preferably saturated.

More specific examples of the aliphatic hydrocarbon group for A include linear and branched aliphatic hydrocarbon groups, an aliphatic hydrocarbon groups containing a ring in the structure thereof.

The linear and branched aliphatic hydrocarbon groups preferably contain 1 to 10 carbon atoms, and more preferably 1 to 8, still more preferably 2 to 5, and most preferably 1 or 2 carbon atoms.

As the linear aliphatic hydrocarbon group, a linear alkylene group is preferable, and specific examples thereof include a methylene group, an ethylene group [—$CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, a branched alkylene group is preferable, and specific examples include alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$— and —$C(CH_2CH_3)_2$—, alkylethylene groups such as —$CH(CH_3)CH_2$—, —$CH(CH_3)CH(CH_3)$—, —$C(CH_3)_2CH_2$— and —$CH(CH_2CH_3)CH_2$—, alkyltrimethylene groups such as —$CH(CH_3)CH_2CH_2$— and —$CH_2CH(CH_3)CH_2$—, and alkyltetramethylene groups such as —$CH(CH_3)CH_2CH_2CH_2$— and —$CH_2CH(CH_3)CH_2CH_2$—. As the alkyl group within the alkylalkylene group, a linear alkyl group of 1 to 5 carbon atoms is preferable.

The linear or branched aliphatic hydrocarbon group (chain-like aliphatic hydrocarbon group) may or may not have a substituent. Examples of the substituent include a fluorine atom, a fluorinated alkyl group of 1 to 5 carbon atoms, and an oxygen atom (=O).

Examples of the aliphatic hydrocarbon group containing a ring in the structure thereof include cyclic aliphatic hydrocarbon groups (groups in which two or more hydrogen atoms have been removed from an aliphatic hydrocarbon ring), and groups in which the cyclic aliphatic hydrocarbon group is bonded to the terminal of an aforementioned chain-like aliphatic hydrocarbon group or interposed within the chain of an aforementioned chain-like aliphatic hydrocarbon group.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic group, a group in which two or more hydrogen atoms have been removed from a monocycloalkane of 3 to 6 carbon atoms is preferable.

Examples of the monocycloalkane include cyclopentane and cyclohexane. As the polycyclic group, a group in which two or more hydrogen atoms have been removed from a polycycloalkane of 7 to 12 carbon atoms is preferable. Examples of the polycycloalkane include adamantane, norbornane, isobornane, tricyclodecane and tetracyclododecane.

The cyclic aliphatic hydrocarbon group may or may not have a substituent. Examples of the substituent include a lower alkyl group of 1 to 5 carbon atoms, a fluorine atom, a fluorinated alkyl group of 1 to 5 carbon atoms, and an oxygen atom (=O).

For the group A, a linear aliphatic hydrocarbon group is preferred, a linear alkylene group is more preferable, a linear alkylene group of 1 to 5 carbon atoms is still more preferable, and a methylene group or ethylene group is the most desirable.

Further, a group composed of a linear alkylene group and a monocyclic group is also preferred as the group A. Specific examples include -(methylene group)-(cyclohexyl group)-(methylene group)-structures, and the group in which the methylene groups are bonded to the 1st and 4th positions of the cyclohexyl group is the most desirable.

Examples of the hydrocarbon group for B include the same divalent hydrocarbon groups as those described above for A.

For the group B, a linear or branched aliphatic hydrocarbon group is preferred, and a methylene group or ethylene group is particularly desirable.

In the above formulas (p11) and (p11-1), $R^{20}$ represents an organic group having a 1,3-dioxole skeleton.

The organic group for $R^{20}$ may be a group that has no aromaticity or a group that has aromaticity, but is preferably a group that has aromaticity, and is more preferably a group in which one or more hydrogen atoms have been removed from a benzodioxole or a derivative thereof.

Specific examples of $R^{20}$ are shown below.

[Chemical Formula 7]

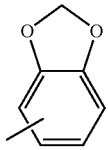
(g1-1)

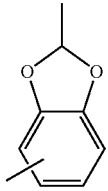
(g1-2)

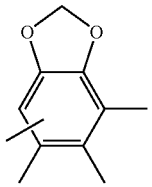
(g1-3)

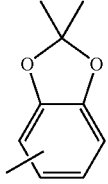
(g1-4)

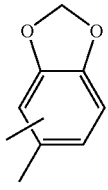
(g1-5)

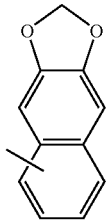
(g1-6)

(g1-7) 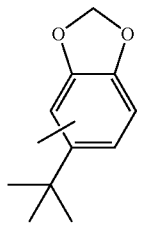

[Chemical Formula 8]

(g1-8) 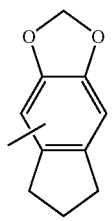

(g1-9) 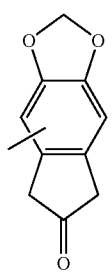

(g1-10) 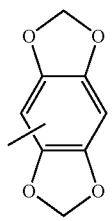

(g1-11) 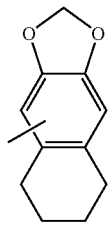

(g1-12) 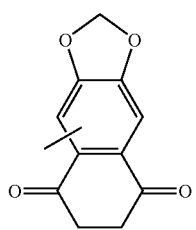

(g1-13) 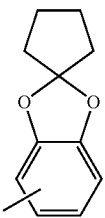

Further, examples of the acetal-type acid-dissociable, dissolution-inhibiting group include groups represented by general formula (p12) shown below.

[Chemical Formula 9]

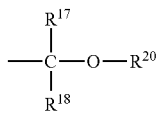

(p12)

In this formula, each of $R^{17}$ and $R^{18}$ independently represents a linear or branched alkyl group or a hydrogen atom, and $R^{20}$ represents an organic group having a 1,3-dioxole skeleton. Further, $R^{17}$ may be a linear or branched alkylene group, wherein the terminal of $R^{17}$ is bonded to $R^{20}$ to form a ring.

In formula (p12), the alkyl group for $R^{17}$ and $R^{18}$ preferably contains 1 to 15 carbon atoms, and may be either a linear or branched alkyl group, although an ethyl group or methyl group is preferable, and a methyl group is the most desirable. It is particularly desirable that one of $R^{17}$ and $R^{18}$ is a hydrogen atom and the other is a methyl group.

Further, in the above formula, $R^{17}$ may be a linear or branched alkylene group (and preferably an alkylene group of 1 to 5 carbon atoms) wherein the terminal of $R^{17}$ is bonded to $R^{20}$ to form a ring.

In such a case, a ring is formed by $R^{17}$, $R^{20}$, the oxygen atom having $R^{20}$ bonded thereto, and the carbon atom having the oxygen atom and $R^{17}$ bonded thereto.

In formula (p12), $R^{20}$ represents an organic group having a 1,3-dioxole skeleton, and is the same as defined for $R^{20}$ in the above formulas (p11) and (p11-1).

Specific examples of the "acid-dissociable, dissolution-inhibiting group having a 1,3-dioxole skeleton" are shown below.

[Chemical Formula 10]

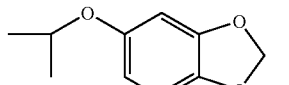

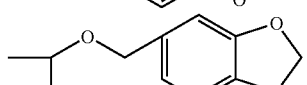

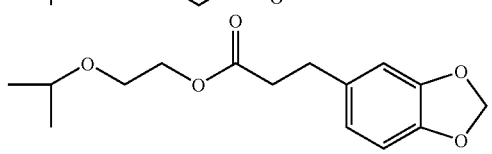

-continued

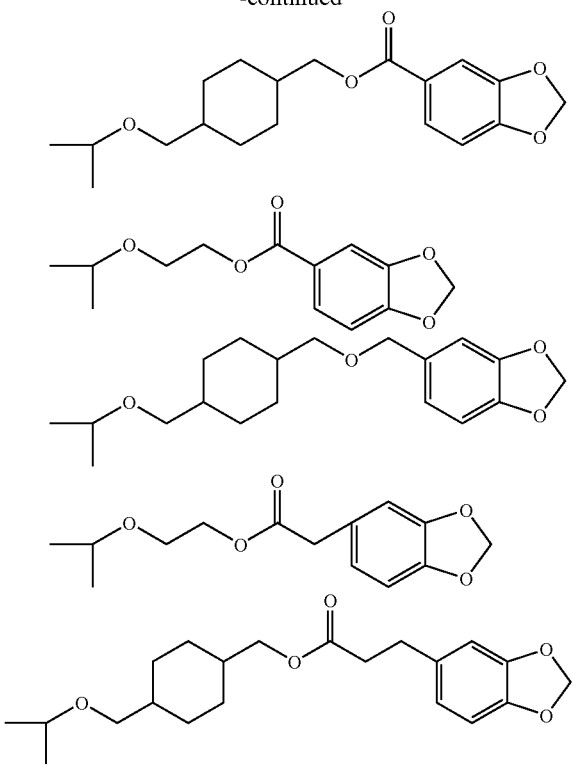

There are no particular restrictions on the main chain within the structural unit (a0), although examples of preferred main chains include structural units derived from a hydroxystyrene, structural units derived from a vinylnaphthol, structural units derived from a vinylbenzoic acid, structural units derived from an acrylate ester, and structural units having a cyclic main chain (hereafter referred to as a "cyclic main chain structural unit"). Of these structural units, structural units derived from a hydroxystyrene, structural units derived from a vinylnaphthol, structural units derived from a vinylbenzoic acid and structural units derived from an acrylate ester are more preferable, structural units derived from a hydroxystyrene and structural units derived from a vinylbenzoic acid are still more preferable, and structural units derived from a hydroxystyrene are the most desirable.

In the present description and the claims, the expression "structural unit derived from a hydroxystyrene" describes a structural unit formed by cleavage of the ethylenic double bond of a hydroxystyrene.

A "structural unit derived from a vinylnaphthol" describes a structural unit formed by cleavage of the ethylenic double bond of a vinylnaphthol.

A "structural unit derived from a vinylbenzoic acid" describes a structural unit formed by cleavage of the ethylenic double bond of a vinylbenzoic acid.

A "structural unit derived from an acrylate ester" describes a structural unit formed by cleavage of the ethylenic double bond of an acrylate ester.

Further, in the present description, the expression "cyclic main chain structural unit" describes a structural unit having a monocyclic or polycyclic structure, wherein at least one, and preferably two or more, of the carbon atoms within a ring of the cyclic structure constitute part of the main chain.

The term "hydroxystyrene" includes hydroxystyrenes, compounds in which the hydrogen atom at the α-position of a hydroxystyrene has been substituted with another substituent such as an alkyl group, and derivatives thereof. Unless specified otherwise, the α-position (α-position carbon atom) of a structural unit derived from a hydroxystyrene refers to the carbon atom to which the benzene ring is bonded.

Examples of the alkyl group for the substituent at the α-position of the hydroxystyrene include alkyl groups of 1 to 5 carbon atoms, and specific examples include linear and branched alkyl groups such as a methyl group, ethyl group, propyl group, isopropyl group, n-butyl group, isobutyl group, tert-butyl group, pentyl group, isopentyl group or neopentyl group.

The term "vinylnaphthol" includes vinylnaphthols, compounds in which the hydrogen atom at the α-position of a vinylnaphthol has been substituted with another substituent such as an alkyl group, and derivatives thereof. Unless specified otherwise, the α-position (α-position carbon atom) of a structural unit derived from a vinylnaphthol refers to the carbon atom to which the naphthalene ring is bonded.

Examples of the alkyl group for the substituent at the α-position of the vinylnaphthol include alkyl groups of 1 to 5 carbon atoms, and specific examples include linear and branched alkyl groups such as a methyl group, ethyl group, propyl group, isopropyl group, n-butyl group, isobutyl group, tert-butyl group, pentyl group, isopentyl group or neopentyl group.

The term "vinylbenzoic acid" includes vinylbenzoic acids, compounds in which the hydrogen atom at the α-position of a vinylbenzoic acid has been substituted with another substituent such as an alkyl group, and derivatives thereof. Unless specified otherwise, the α-position (α-position carbon atom) of a structural unit derived from a vinylbenzoic acid refers to the carbon atom to which the benzene ring is bonded.

Examples of the alkyl group for the substituent at the α-position of the vinylbenzoic acid include alkyl groups of 1 to 5 carbon atoms, and specific examples include linear and branched alkyl groups such as a methyl group, ethyl group, propyl group, isopropyl group, n-butyl group, isobutyl group, tert-butyl group, pentyl group, isopentyl group or neopentyl group.

The term "acrylate ester" includes acrylate esters having a hydrogen atom bonded to the α-position carbon atom, and compounds having a substituent (an atom other than hydrogen, or a group) bonded to the α-position carbon atom. Examples of the substituent include lower alkyl groups and halogenated lower alkyl groups. Unless specified otherwise, the α-position (α-position carbon atom) of a structural unit derived from an acrylate ester refers to the carbon atom to which the carbonyl group is bonded.

In the acrylate ester, examples of the lower alkyl group for the substituent at the α-position include linear and branched alkyl groups such as a methyl group, ethyl group, propyl group, isopropyl group, n-butyl group, isobutyl group, tert-butyl group, pentyl group, isopentyl group or neopentyl group.

Further, examples of the halogenated lower alkyl group include groups in which part or all of the hydrogen atoms within an aforementioned "lower alkyl group for the substituent at the α-position" have been substituted with halogen atoms. Examples of the halogen atoms include a fluorine atom, chlorine atom, bromine atom or iodine atom, and a fluorine atom is particularly desirable.

In the present invention, the moiety bonded to the α-position of the acrylate ester is preferably a hydrogen atom, a lower alkyl group or a halogenated lower alkyl group, is more preferably a hydrogen atom, a lower alkyl group or a fluorinated lower alkyl group, and in terms of industrial availability, is most preferably a hydrogen atom or a methyl group.

In the present invention, the structural unit (a0) is preferably a structural unit represented by general formula (a0-1) shown below.

[Chemical Formula 11]

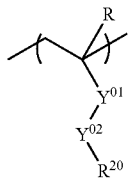

(a0-1)

In formula (a0-1), R represents a hydrogen atom, an alkyl group of 1 to 5 carbon atoms or a halogenated alkyl group of 1 to 5 carbon atoms, $Y^{01}$ represents a divalent organic group that becomes an alkali-soluble group upon cleavage of the bond to $Y^{02}$ under the action of acid, $Y^{02}$ represents a single bond or a divalent linking group, and $R^{20}$ represents an organic group having a 1,3-benzodioxole skeleton.

In formula (a0-1), R represents a hydrogen atom, an alkyl group of 1 to 5 carbon atoms, or a halogenated alkyl group of 1 to 5 carbon atoms.

Examples of the alkyl group or halogenated alkyl group for R include the same groups as those listed above for the lower alkyl group or halogenated lower alkyl group that may be bonded to the α-position of an acrylate ester.

R is preferably a hydrogen atom, an alkyl group of 1 to 5 carbon atoms or a fluorinated alkyl group of 1 to 5 carbon atoms, and in terms of industrial availability, is most preferably a hydrogen atom or a methyl group.

In formula (a0-1), $Y^{01}$ represents a divalent organic group that becomes an alkali-soluble group upon cleavage of the bond to $Y^{02}$ under the action of acid.

Examples of the alkali-soluble group that is formed include a phenolic hydroxyl group (—OH), a thiol group (—SH) or a carboxyl group (—C(=O)—OH) or the like.

Accordingly, examples of $Y^{01}$ include $Y^{01\prime}$—O—, $Y^{01\prime}$—S— or $Y^{01\prime}$—C(=O)—O— (wherein $Y^{01\prime}$ represents a divalent aromatic group), and —C(=O)—O—.

Specific examples of the divalent aromatic group for $Y^{01\prime}$ include groups in which two or more hydrogen atoms have been removed from an aromatic hydrocarbon ring which may have a substituent.

The aromatic hydrocarbon ring preferably contains 6 to 15 carbon atoms, and specific examples include a benzene ring, naphthalene ring, phenanthrene ring or anthracene ring. Of these, a benzene ring or naphthalene ring is particularly desirable.

Examples of the substituent which the aromatic hydrocarbon ring may have include halogen atoms, alkyl groups, alkoxy groups, hydrogenated alkyl groups of 1 to 5 carbon atoms, and an oxygen atom (=O). Specific examples of the halogen atoms include a fluorine atom, chlorine atom, iodine atom or bromine atom. The substituent which the aromatic hydrocarbon ring may have is preferably a fluorine atom.

The divalent aromatic group for $Y^{01\prime}$ preferably has no substituents.

In those cases where the divalent aromatic group for $Y^{01\prime}$ does have a substituent, the number of substituent may be either one, or two or more, but is preferably one or two, and is most preferably one.

In formula (a0-1), $Y^{02}$ represents a single bond or a divalent linking group.

The divalent linking group for $Y^{02}$ may be any group for which the bond to $Y^{01}$ is cleaved under the action of acid, and examples include groups that form a tertiary alkyl ester with the atom (such as an oxygen atom or sulfur atom) at the terminal of $Y^{01}$, and groups having an acetal bond. Examples of groups having an acetal bond include groups represented by a general formula —C(R$^{1\prime}$)(R$^{2\prime}$)—O—Q$^0$-. In this general formula, R$^{1\prime}$, R$^{2\prime}$ and Q$^0$ are the same as defined above for R$^{1\prime}$, R$^{2\prime}$ and Q$^0$ in formula (p11).

Of the various possibilities, the divalent organic group for $Y^{02}$ is preferably a group having an acetal bond, as such groups are more likely to yield the desired effects for the present invention. Groups represented by the general formula —C(R$^{1\prime}$)(R$^{2\prime}$)—O—Q$^0$- are more preferred, and divalent linking groups containing a group represented by general formula (p11') shown below are particularly desirable.

[Chemical Formula 12]

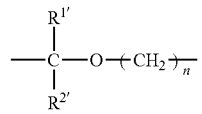

(p11')

In formula (p11'), each of R$^{1\prime}$ and R$^{2\prime}$ independently represents a hydrogen atom or an alkyl group of 1 to 5 carbon atoms, and n represents an integer of 0 to 3.

In formula (p11'), R$^{1\prime}$ and R$^{2\prime}$ are the same as defined above for R$^{1\prime}$ and R$^{2\prime}$ in formula (p11).

n represents an integer of 0 to 3, is preferably an integer of 0 to 2, and is most preferably 1 or 2.

In formula (a0-1), R$^{20}$ represents an organic group having a 1,3-dioxole skeleton, and is the same as defined above for R$^{20}$ in formula (p11).

In the present invention, the structural unit (a0) is preferably a structural unit represented by general formula (a0-1') shown below.

[Chemical Formula 13]

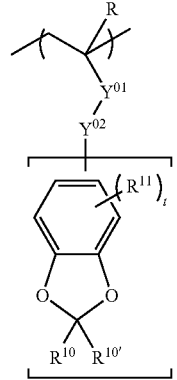

(a0-1')

In formula (a0-1'), R represents a hydrogen atom, an alkyl group of 1 to 5 carbon atoms or a halogenated alkyl group of 1 to 5 carbon atoms, $Y^{01}$ represents a divalent organic group that becomes an alkali-soluble group upon cleavage of the bond to $Y^{02}$ under the action of acid, $Y^{02}$ represents a single bond or a divalent linking group, which substitutes one of the hydrogen atoms of the group within the brackets [ ] of formula (a0-1') that is derived from either a 1,3-benzodioxole or a derivative thereof, $R^{11}$ represents a hydrocarbon group of 1 to 30 carbon atoms which may have a substituent, t represents an integer of 0 to 3, and in those cases where t is 2 or 3, a plurality of $R^{11}$ groups may be bonded together to form a ring, or may be bonded to the benzene ring to form an aromatic ring, $R^{10}$ represents a hydrogen atom or an alkyl group of 1 to 5 carbon atoms which may have a substituent, $R^{10'}$ represents a hydrogen atom or an alkyl group of 1 to 5 carbon atoms which may have a substituent, and $R^{10}$ and $R^{10'}$ may be bonded together to form a ring.

In formula (a0-1'), R and $Y^{01}$ are the same as defined above for R and $Y^{01}$ in formula (a0-1).

In formula (a0-1'), $Y^{02}$ is the same single bond or divalent linking group as defined above for $Y^{02}$ in formula (a0-1), and substitutes one of the hydrogen atoms of the group within the brackets [ ] of formula (a0-1') that is derived from either a 1,3-benzodioxole or a derivative thereof.

In those cases where $Y^{02}$ is a single bond, the hydrogen atom within the alkali-soluble group described above for $Y^{01}$ is substituted with the group within the brackets [ ] of formula (a0-1') that is derived from either a 1,3-benzodioxole or a derivative thereof (or in other words, $Y^{01}$ substitutes one of the hydrogen atoms of the group within the brackets [ ] of formula (a0-1') that is derived from either a 1,3-benzodioxole or a derivative thereof).

In those cases where $Y^{02}$ is a divalent linking group, $Y^{02}$ substitutes one of the hydrogen atoms of the group derived from either a 1,3-benzodioxole or a derivative thereof.

$Y^{02}$ (or $Y^{01}$ in those cases where $Y^{02}$ is a single bond) is preferably bonded to a carbon atom within the group inside the brackets [ ] of formula (a0-1') that is derived from either a 1,3-benzodioxole or a derivative thereof, and is more preferably bonded to a carbon atom that constitutes part of the aromatic ring.

In formula (a0-1'), $R^H$ represents a hydrocarbon group of 1 to 30 carbon atoms which may have a substituent. The hydrocarbon group for $R^{11}$ may be either an aromatic hydrocarbon group or an aliphatic hydrocarbon group.

The aromatic hydrocarbon group for $R^{11}$ is a hydrocarbon group having an aromatic ring.

The aromatic hydrocarbon group preferably has 3 to 30 carbon atoms, more preferably 5 to 30, still more preferably 5 to 20, still more preferably 6 to 15, and most preferably 6 to 12 carbon atoms. Here, the number of carbon atoms within substituent(s) is not included in the number of carbon atoms of the aromatic hydrocarbon group.

Specific examples of the aromatic hydrocarbon group include aryl groups, which are groups in which one hydrogen atom has been removed from an aromatic hydrocarbon ring, such as a phenyl group, biphenyl group, fluorenyl group, naphthyl group, anthryl group or phenanthryl group, and arylalkyl groups such as a benzyl group, phenethyl group, 1-naphthylmethyl group, 2-naphthylmethyl group, 1-naphthylethyl group or 2-naphthylethyl group. The alkyl chain within the arylalkyl group preferably has 1 to 4 carbon atoms, more preferably 1 to 3 carbon atoms, and most preferably 1 or 2 carbon atoms.

The aromatic hydrocarbon group may have a substituent. For example, some of the carbon atoms constituting the aromatic ring within the aromatic hydrocarbon group may be substituted with a hetero atom, or a hydrogen atom bonded to the aromatic ring within the aromatic hydrocarbon group may be substituted with a substituent.

Examples of the former case include heteroaryl groups in which some of the carbon atoms constituting the ring within an aforementioned aryl group have been substituted with a hetero atom such as an oxygen atom, a sulfur atom or a nitrogen atom, and heteroarylalkyl groups in which some of the carbon atoms constituting the aromatic hydrocarbon ring within an aforementioned arylalkyl group have been substituted with an aforementioned hetero atom.

In the latter case, examples of the substituent for the aromatic hydrocarbon group include an alkyl group, an alkoxy group, a halogen atom, a halogenated alkyl group, a hydroxyl group or an oxygen atom (=O) or the like.

The alkyl group used as the substituent is preferably an alkyl group of 1 to 5 carbon atoms, and a methyl group, ethyl group, propyl group, n-butyl group or tert-butyl group is particularly desirable.

The alkoxy group used as the substituent is preferably an alkoxy group having 1 to 5 carbon atoms, is more preferably a methoxy group, ethoxy group, n-propoxy group, iso-propoxy group, n-butoxy group or tert-butoxy group, and is most preferably a methoxy group or an ethoxy group.

Examples of the halogen atom used as the substituent include a fluorine atom, a chlorine atom, a bromine atom and an iodine atom, and a fluorine atom is preferable.

Examples of the halogenated alkyl group used as the substituent include groups in which some or all of the hydrogen atoms within an alkyl group of 1 to 5 carbon atoms (such as a methyl group, ethyl group, propyl group, n-butyl group or tert-butyl group) have been substituted with the above halogen atoms.

The aliphatic hydrocarbon group for $R^{11}$ may be either a saturated aliphatic hydrocarbon group or an unsaturated aliphatic hydrocarbon group. Further, the aliphatic hydrocarbon group may be linear, branched or cyclic.

As the aliphatic hydrocarbon group, a linear or branched monovalent saturated hydrocarbon group, a linear or branched monovalent unsaturated hydrocarbon group, or a cyclic aliphatic hydrocarbon group (aliphatic cyclic group) is preferred.

In the aliphatic hydrocarbon group for $R^{11}$, some of the carbon atoms that constitute the aliphatic hydrocarbon group may be substituted with a substituent containing a hetero atom, or some or all of the hydrogen atoms that constitute the aliphatic hydrocarbon group may be substituted with a substituent containing a hetero atom.

There are no particular limitations on this "hetero atom", provided it is an atom other than a carbon atom and a hydrogen atom. Examples of the hetero atom include a halogen atom, an oxygen atom, a sulfur atom and a nitrogen atom. Examples of halogen atoms include a fluorine atom, chlorine atom, iodine atom or bromine atom.

The substituent containing a hetero atom may consist solely of the hetero atom, or may be a group that also contains a group or atom other than the hetero atom.

Specific examples of the substituent for substituting some of the carbon atoms of the aliphatic hydrocarbon group include —O—, —C(=O)—O—, —O—C(=O)—O—, —C(=O)—NH—, —NH— (wherein H may be replaced with a substituent such as an alkyl group or an acyl group), —S—, —S(=O)$_2$— and —S(=O)$_2$—O—. When the aliphatic hydrocarbon group is cyclic, the aliphatic hydrocarbon group may contain any of these substituent groups within the ring structure.

Examples of the substituent for substituting some or all of the hydrogen atoms of the aliphatic hydrocarbon group include an alkoxy group, a halogen atom, a halogenated alkyl group, a hydroxyl group, an oxygen atom (=O), a cyano group and an alkyl group.

The alkoxy group is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the halogen atom include a fluorine atom, a chlorine atom, a bromine atom and an iodine atom, and a fluorine atom is preferable.

Examples of the halogenated alkyl group include groups in which some or all of the hydrogen atoms within an alkyl group of 1 to 5 carbon atoms (such as a methyl group, ethyl group, propyl group, n-butyl group or tert-butyl group) have been substituted with the aforementioned halogen atoms.

Examples of the alkyl group include alkyl groups of 1 to 5 carbon atoms, and a methyl group, ethyl group, propyl group, n-butyl group or tert-butyl group is preferable.

The linear saturated hydrocarbon group (alkyl group) preferably has 1 to 20 carbon atoms, more preferably 1 to 15 carbon atoms, and most preferably 1 to 10 carbon atoms. Specific examples include a methyl group, ethyl group, propyl group, butyl group, pentyl group, hexyl group, heptyl group, octyl group, nonyl group, decyl group, undecyl group, dodecyl group, tridecyl group, isotridecyl group, tetradecyl group, pentadecyl group, hexadecyl group, isohexadecyl group, heptadecyl group, octadecyl group, nonadecyl group, eicosyl group, heneicosyl group or docosyl group.

The branched saturated hydrocarbon group (alkyl group) preferably has 3 to 20 carbon atoms, more preferably 3 to 15 carbon atoms, and most preferably 3 to 10 carbon atoms. Specific examples include a 1-methylethyl group, 1-methylpropyl group, 2-methylpropyl group, 1-methylbutyl group, 2-methylbutyl group, 3-methylbutyl group, 1-ethylbutyl group, 2-ethylbutyl group, 1-methylpentyl group, 2-methylpentyl group, 3-methylpentyl group or 4-methylpentyl group.

The unsaturated hydrocarbon group preferably has 2 to 10 carbon atoms, more preferably 2 to 5, still more preferably 2 to 4, and most preferably 3 carbon atoms.

Examples of linear monovalent unsaturated hydrocarbon groups include a vinyl group, a propenyl group (an allyl group) and a butynyl group.

Examples of branched monovalent unsaturated hydrocarbon groups include a 1-methylpropenyl group and a 2-methylpropenyl group.

Among the above examples, the unsaturated hydrocarbon group is most preferably a propenyl group.

The cyclic aliphatic hydrocarbon group (aliphatic cyclic group) for $R^{11}$ is an aliphatic cyclic group of 3 to 30 carbon atoms which may have a substituent.

The aliphatic cyclic group may be either a monocyclic group or a polycyclic group. The aliphatic cyclic group preferably has 3 to 30 carbon atoms, more preferably 5 to 30, still more preferably 5 to 20, still more preferably 6 to 15, and most preferably 6 to 12 carbon atoms.

Examples of the aliphatic cyclic group include groups in which one or more hydrogen atoms have been removed from a monocycloalkane, and groups in which one or more hydrogen atoms have been removed from a polycycloalkane such as a bicycloalkane, tricycloalkane or tetracycloalkane. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane.

Of the above possibilities, in the present invention, $R^{11}$ is preferably an aliphatic hydrocarbon group which may have a substituent, and is more preferably an alkyl group of 1 to 5 carbon atoms which may have a substituent. t is preferably 0.

In the above formula (a0-1'), each of $R^{10}$ and $R^{10'}$ independently represents a hydrogen atom or an alkyl group of 1 to 5 carbon atoms which may have a substituent, and $R^{10}$ and $R^{10'}$ may be bonded together to form a ring. Here, the "1 to 5 carbon atoms" excludes the carbon atoms within any substituents.

Specific examples of the alkyl groups for $R^{10}$ and $R^{10'}$ include a methyl group, ethyl group, n-propyl group, i-propyl group, n-butyl group or tert-butyl group.

Examples of the substituent include a fluorine atom, a fluorinated lower alkyl group, an oxygen atom (=O) or a hydroxyl group. Further, part of the carbon atoms that constitute the alkyl group of 1 to 5 carbon atoms may be substituted with a substituent containing a hetero atom. Specific examples of this substituent containing a hetero atom include —O—, —C(=O)—O—, —C(=O)—, —C(=O)—NH—, —NH— (wherein H may be replaced with a substituent such as an alkyl group or an acyl group), —S—, —S(=O)$_2$— and —S(=O)$_2$—O—.

Of the various possibilities above, those cases where $R^{10}$ and $R^{10'}$ are both hydrogen atoms, those cases where $R^{10}$ and $R^{10'}$ are both alkyl groups of 1 to 5 carbon atoms (that contain no substituents), and those cases where one of $R^{10}$ and $R^{10'}$ is a hydrogen atom and the other is an alkyl group of 1 to 5 carbon atoms (that contains no substituents) are preferred as they yield superior lithography properties such as resolution and resist pattern shape, and also offer superior sensitivity.

More specific examples of the structural unit (a0) include structural units (a01) represented by general formula (a0-1-10) shown below, structural units (a02) represented by general formula (a0-1-20) shown below, structural units (a03) represented by general formula (a0-1-30) shown below, structural units (a04) represented by general formula (a0-1-40) shown below, structural units (a05) represented by general formula (a0-1-50) shown below, and structural units (a06) represented by general formula (a0-1-60) shown below.

[Chemical Formula 14]

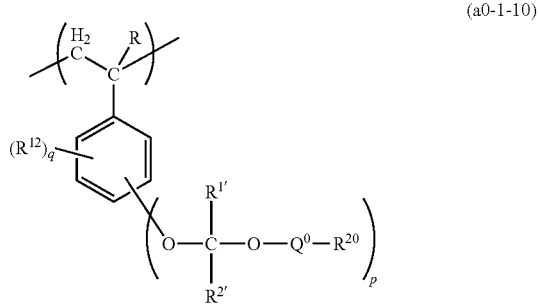

(a0-1-10)

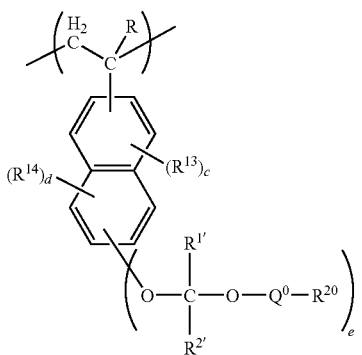
(a0-1-20)

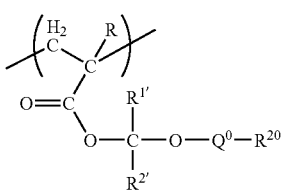
(a0-1-30)

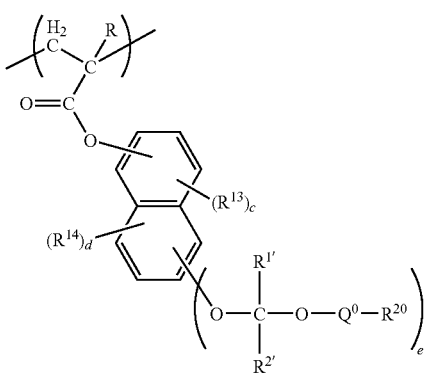
(a0-1-40)

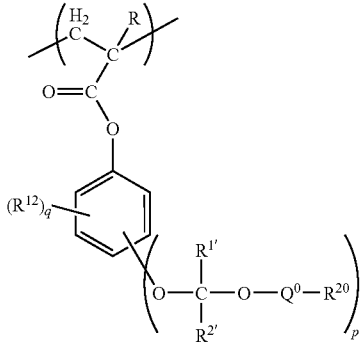
(a0-1-50)

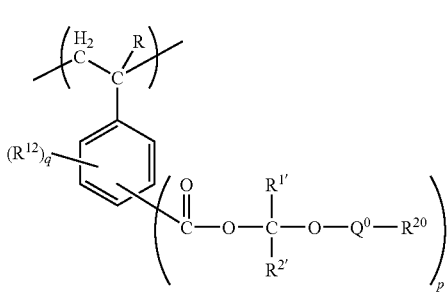
(a0-1-60)

In the above formulas, each R independently represents a hydrogen atom, an alkyl group of 1 to 5 carbon atoms or a halogenated alkyl group of 1 to 5 carbon atoms, each of $R^{1'}$ and $R^{2'}$ independently represents a hydrogen atom or an alkyl group of 1 to 5 carbon atoms, each $Q^0$ independently represents a single bond or a divalent linking group, and each $R^{20}$ independently represents an organic group having a 1,3-dioxole skeleton. In formulas (a0-1-10), (a0-1-50) and (a0-1-60), each $R^{12}$ independently represents a halogen atom, an alkyl group of 1 to 5 carbon atoms or a halogenated alkyl group of 1 to 5 carbon atoms, each p independently represents an integer of 1 to 3, and each q independently represents an integer of 0 to 4, provided that the value of p+q in each case is an integer of 1 to 5. In formulas (a0-1-20) and (a0-1-40), each of $R^{13}$ and $R^{14}$ independently represents a halogen atom, an alkyl group of 1 to 5 carbon atoms or a halogenated alkyl group of 1 to 5 carbon atoms, each c independently represents an integer of 0 to 3, each d independently represents an integer of 0 to 2, and each e independently represents an integer of 1 to 3, provided that the value of d+e in each case is an integer of 1 to 4.

In the above formulas, R represents a hydrogen atom, an alkyl group of 1 to 5 carbon atoms or a halogenated alkyl group of 1 to 5 carbon atoms.

Examples of the alkyl group or halogenated alkyl group for R include the same groups as the lower alkyl group or halogenated lower alkyl group that may be bonded to the α-position of an acrylate ester or a hydroxystyrene.

R is preferably a hydrogen atom, an alkyl group of 1 to 5 carbon atoms or a fluorinated alkyl group of 1 to 5 carbon atoms, and in terms of industrial availability, is most preferably a hydrogen atom or a methyl group.

In the above formulas, each of $R^{1'}$ and $R^{2'}$ independently represents a hydrogen atom or an alkyl group of 1 to 5 carbon atoms, $Q^0$ represents a single bond or a divalent linking group, and $R^{20}$ represents an organic group having a 1,3-dioxole skeleton. $R^{1'}$, $R^{2'}$, $Q^0$ and $R^{20}$ are as defined above for $R^{1'}$, $R^{2'}$, $Q^0$ and $R^{20}$ in formula (p11).

In formulas (a0-1-10), (a0-1-50) and (a0-1-60), $R^{12}$ represents a halogen atom, an alkyl group of 1 to 5 carbon atoms or a halogenated alkyl group of 1 to 5 carbon atoms.

Examples of the halogen atom for $R^{12}$ include a fluorine atom, chlorine atom, bromine atom or iodine atom, and a fluorine atom is particularly desirable.

Examples of the alkyl group for $R^{12}$ include the same groups as the alkyl group of 1 to 5 carbon atoms that may be bonded to the α-position of an aforementioned hydroxystyrene.

Examples of the halogenated alkyl group for $R^{12}$ include groups in which some or all of the hydrogen atoms within an aforementioned "alkyl group of 1 to 5 carbon atoms that may be bonded to the α-position of a hydroxystyrene" have been substituted with halogen atoms, and fluorinated alkyl groups of 1 to 5 carbon atoms are preferred.

In formulas (a0-1-10), (a0-1-50) and (a0-1-60), p represents an integer of 1 to 3, and is most preferably 1.

The bonding position for the group (—O—C($R^{1'}$)($R^{2'}$)—O-$Q^0$-$R^{20}$) may be the o-position, the m-position or the p-position of the phenyl group. In those cases where p is 1, the p-position is preferred in terms of ready availability and low cost. In those cases where p is 2 or 3, any combination of substitution positions can be used.

In formulas (a0-1-10), (a0-1-50) and (a0-1-60), q represents an integer of 0 to 4, preferably an integer of 0 to 2, and more preferably 0 or 1. From an industrial perspective, q is most preferably 0.

When q is 1, the substitution position for $R^{12}$ may be the α-position, the m-position or the p-position. When q is 2, and combination of substitution positions can be used. In such cases, the plurality of $R^{12}$ groups may be the same or different.

However, p+q represents an integer of 1 to 5.

In formulas (a0-1-20) and (a0-1-40), each of $R^{13}$ and $R^{14}$ independently represents a halogen atom, an alkyl group of 1 to 5 carbon atoms or a halogenated alkyl group of 1 to 5 carbon atoms, and specific examples include the same atoms and groups as those listed above for $R^{12}$.

c represents an integer of 0 to 3, is preferably 0 or 1, and for industrial reasons, is most preferably 0.

d represents an integer of 0 to 2, is preferably 0 or 1, and in terms of improving the effects of the present invention, is most preferably 0.

e represents an integer of 1 to 3, and is most preferably 1.

However, d+e represents an integer of 1 to 4.

The α-position carbon atom in formula (a0-1-20) or formula (a0-1-40) may be bonded to either the 1st position of the naphthyl group or the 2nd position of the naphthyl group. Of these options, the α-position carbon atom is preferably bonded to the 1st position of the naphthyl group.

The bonding position for the group (—O—C($R^{1'}$)($R^{2'}$)—O-$Q^0$-$R^{20}$) may be any position other than the bonding position of the above α-position carbon atom.

In those cases where the α-position carbon atom is bonded to the 1st position of the naphthyl group, the bonding position of the group (—O—C($R^{1'}$)($R^{2'}$)—O-$Q^0$-$R^{20}$) in the case where e represents 1 may be any of the 2nd to 8th positions of the naphthyl group. Of these bonding positions, the 4th position or the 5th position is preferred, and in terms of ease of synthesis, the 5th position is the most desirable.

Further, in those cases where the α-position carbon atom is bonded to the 2nd position of the naphthyl group, the bonding position of the group (—O—C($R^{1'}$)($R^{2'}$)—O-$Q^0$-$R^{20}$) may be any position other than the 2nd position, is preferably the 6th or 7th position, and is most preferably the 6th position.

In those cases where e represents 2 or 3, the bonding positions for the groups (—O—C($R^{1'}$)($R^{2'}$)—O-$Q^0$-$R^{20}$) may be any combination of positions not including the bonding position of the aforementioned α-position carbon atom.

The substitution position for $R^{13}$ when c is 1 may be any position other than the bonding position of the above α-position carbon atom. When c is 2, the substitution positions for the $R^{13}$ groups may be any combination of positions not including the bonding position of the aforementioned α-position carbon atom.

The substitution position for $R^{14}$ when d is 1 may be any position other than the bonding position for the group (—O—C($R^{1'}$)($R^{2'}$)—O-$Q^0$-$R^{20}$. When d is 2, the substitution positions for the $R^{14}$ groups may be any combination of positions not including the bonding position for the group (—O—C($R^{1'}$)($R^{2'}$)—O-$Q^0$-$R^{20}$).

In those cases where the substitution position for $R^{14}$ is from the 5th position to the 8th position, the substitution position for $R^{13}$ is preferably from the 1st position to the 4th position.

Specific examples of the above structural units (a01), (a02), (a03), (a04), (a05) and (a06) are shown below.

In each of the following formulas, $R^α$ represents a hydrogen atom, a methyl group or a trifluoromethyl group.

[Chemical Formula 15]

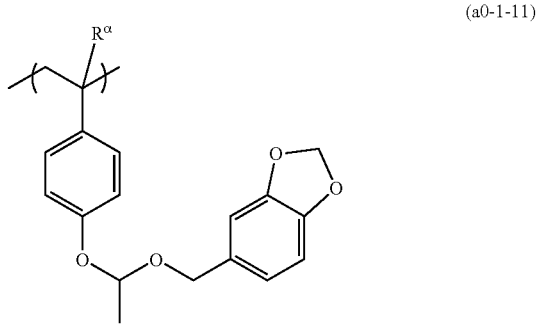

(a0-1-11)

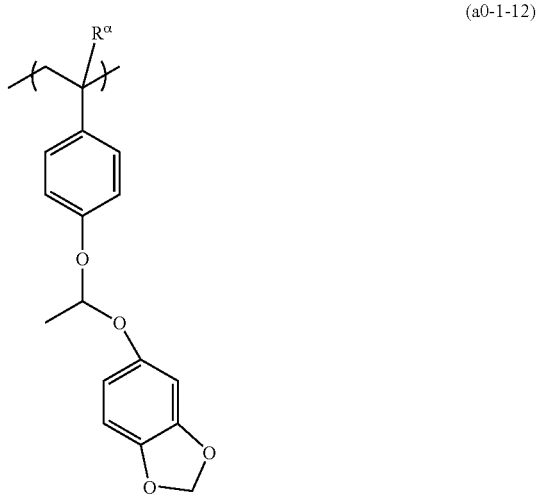

(a0-1-12)

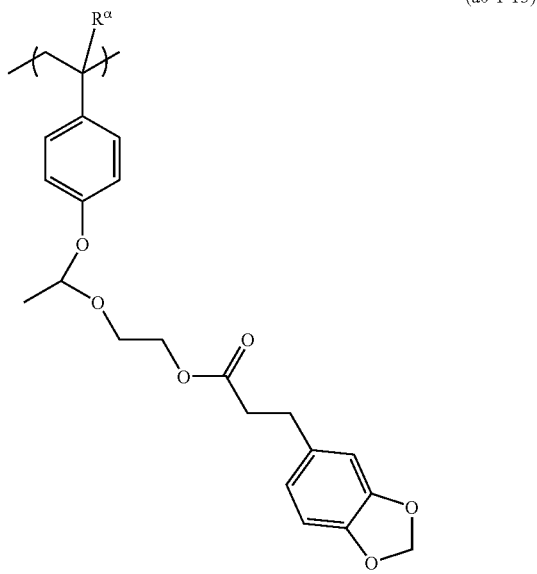

(a0-1-13)

(a0-1-14)
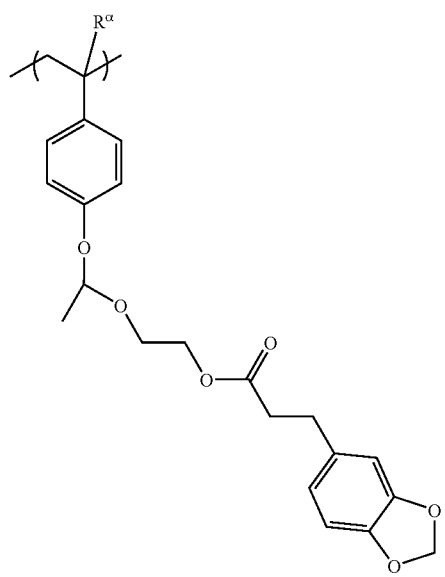
(a0-1-15)
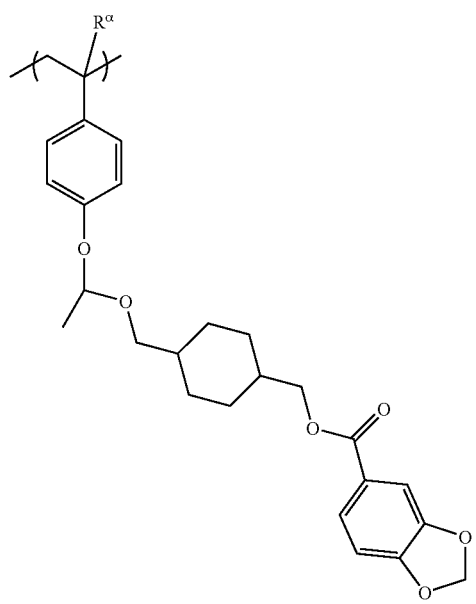
(a0-1-16)
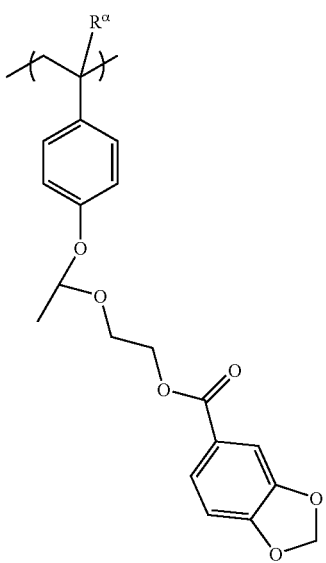
(a0-1-17)
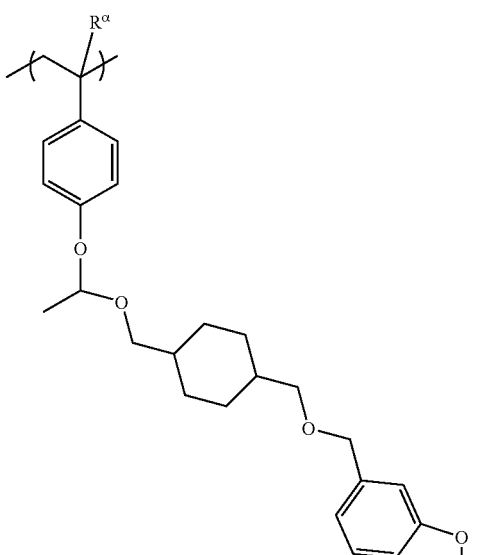

(a0-1-18)
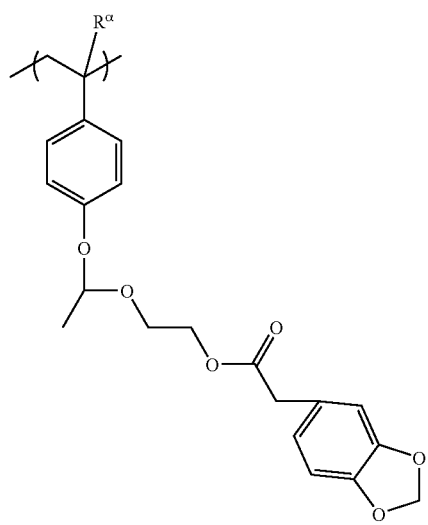
(a0-1-19)
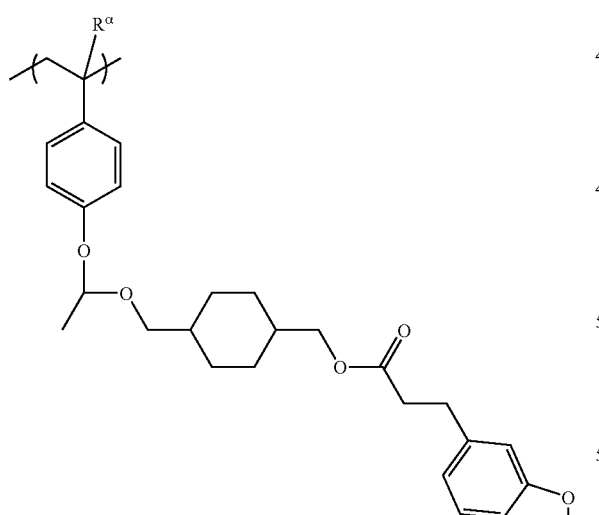
[Chemical Formula 16]
(a0-1-21)
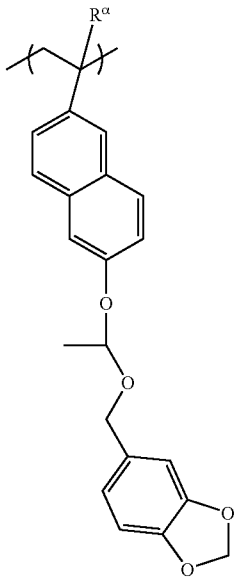
(a0-1-22)
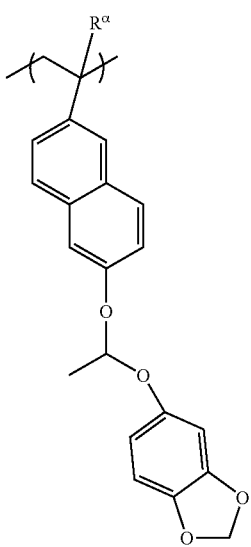

(a0-1-23)
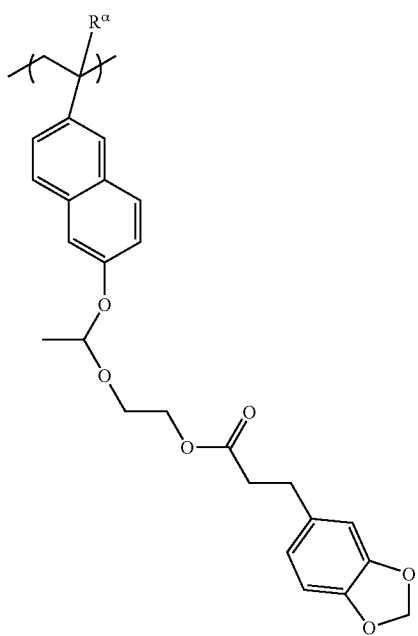
(a0-1-24)
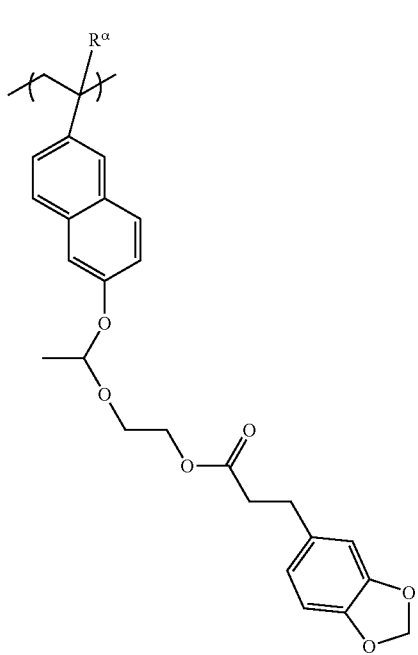
(a0-1-25)
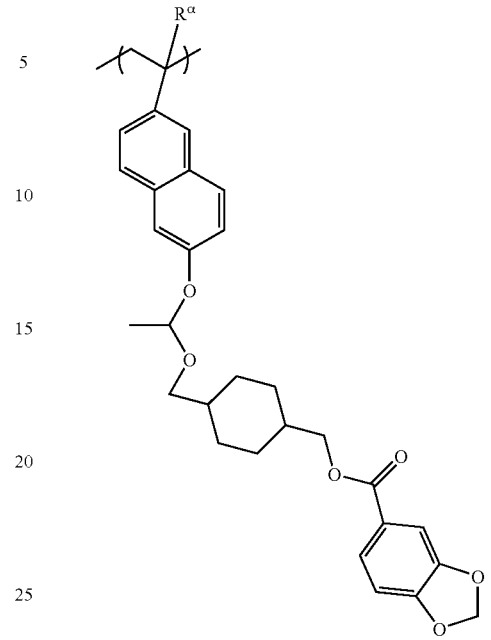
(a0-1-26)
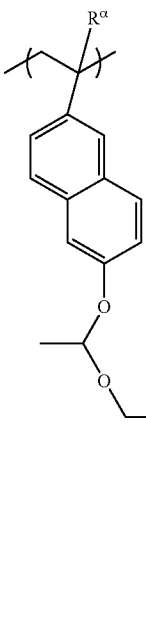

(a0-1-27)
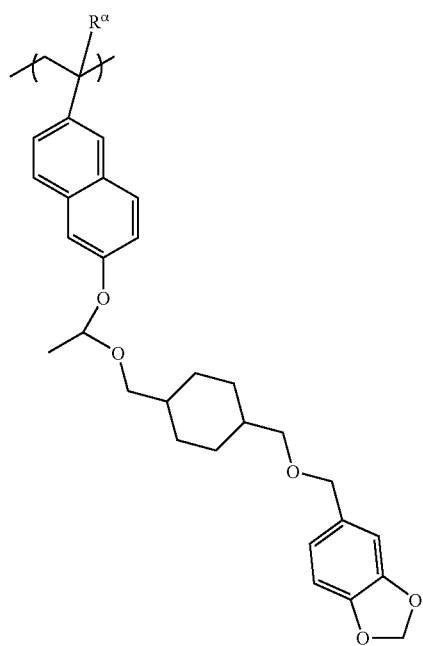
(a0-1-29)
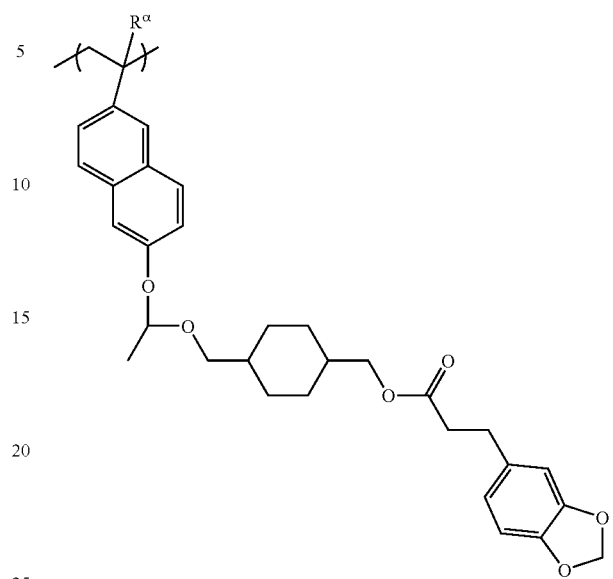
[Chemical Formula 17]
(a0-1-31)
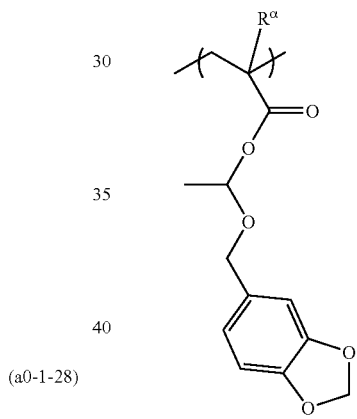
(a0-1-28)
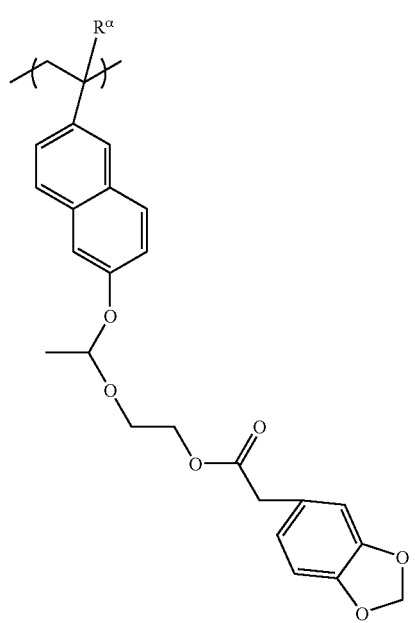
(a0-1-32)
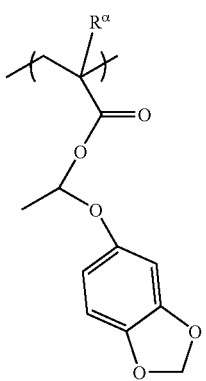

(a0-1-33)
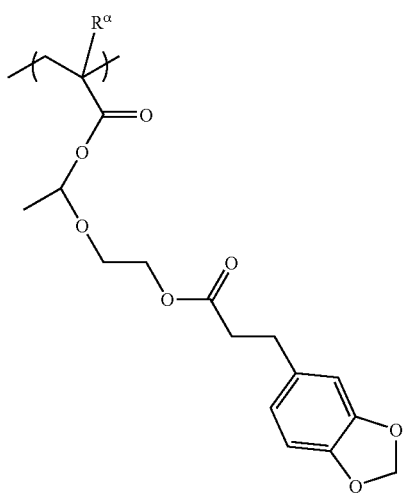
(a0-1-36)
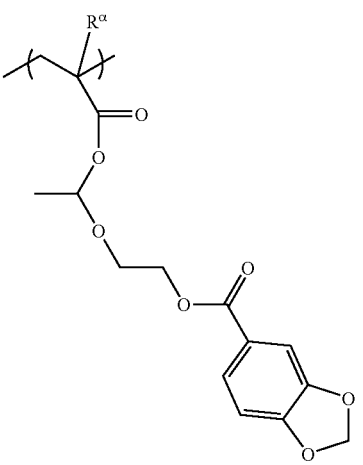
(a0-1-34)
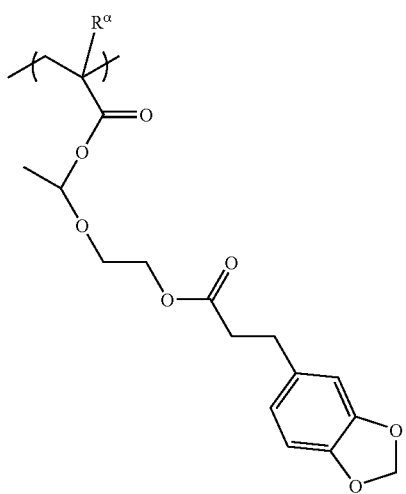
(a0-1-37)
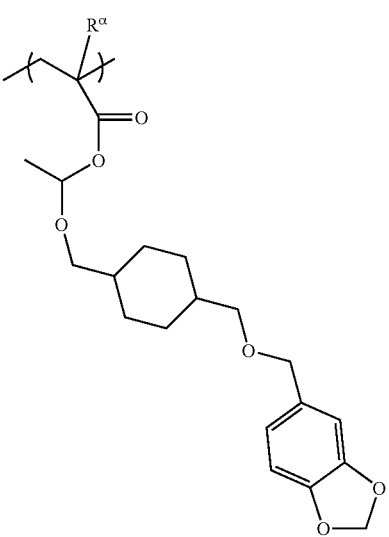
(a0-1-35)
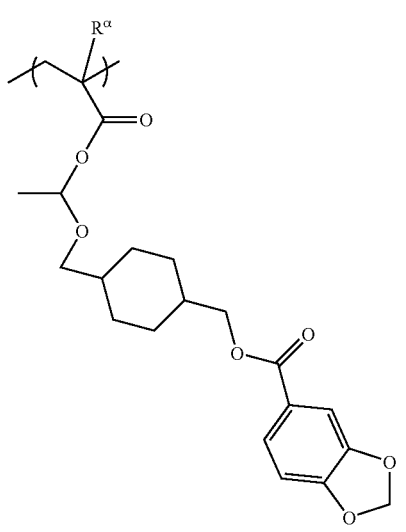
(a0-1-38)
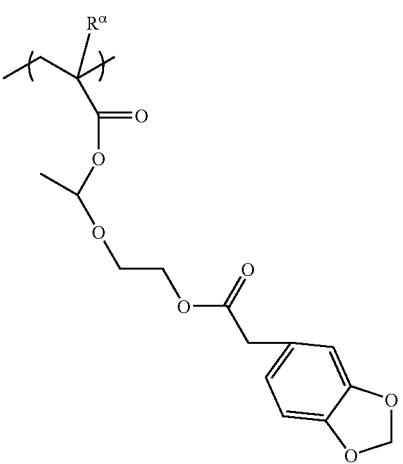

(a0-1-39)
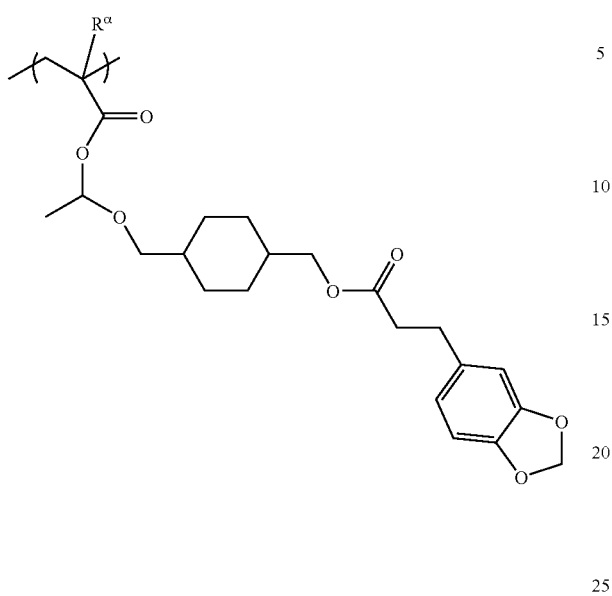
[Chemical Formula 18]
(a0-1-41)
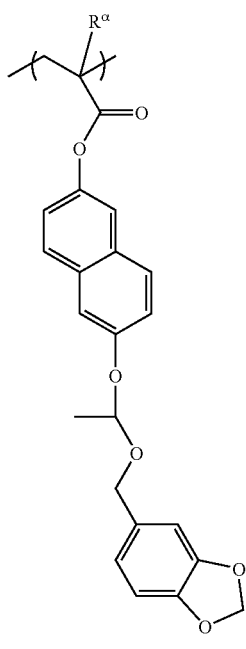
(a0-1-42)
(a0-1-43)
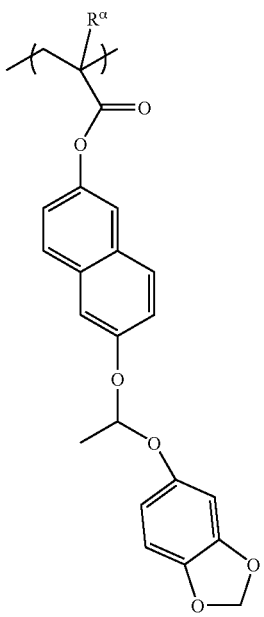

(a0-1-44)
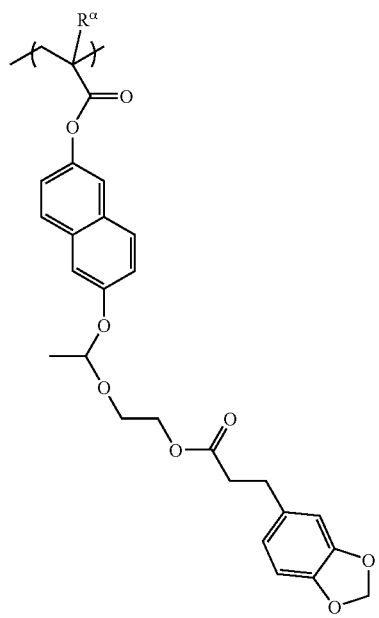
(a0-1-45)
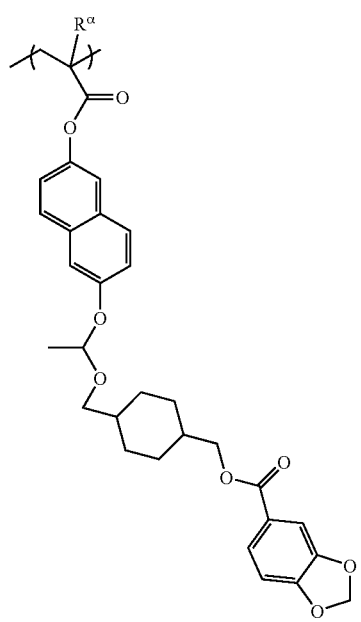
(a0-1-46)
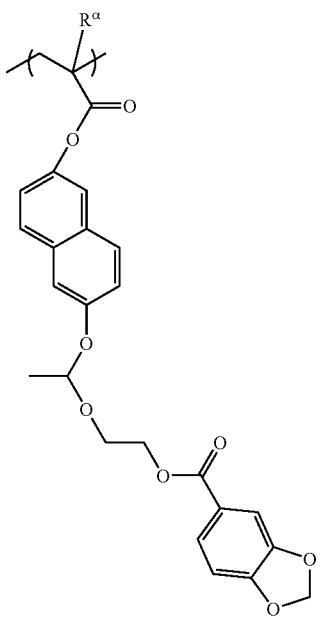
(a0-1-47)
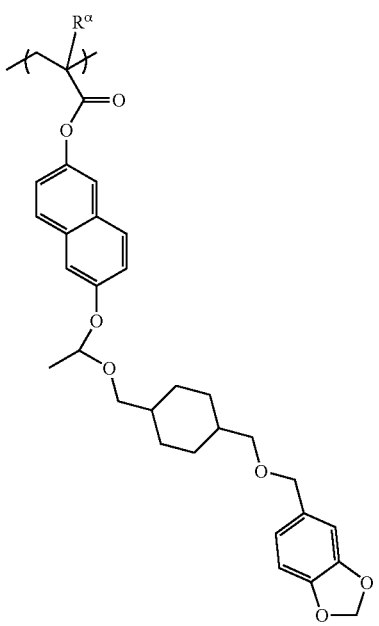

(a0-1-48)
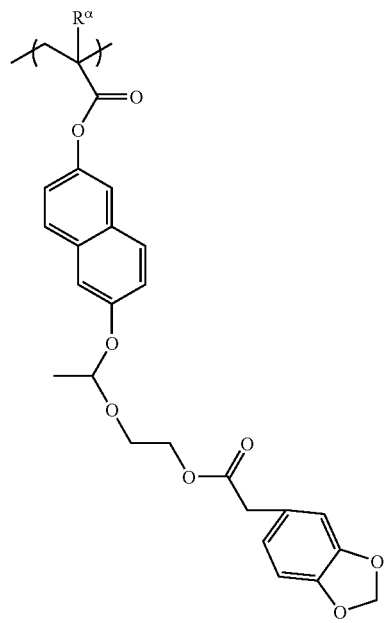
(a0-1-49)
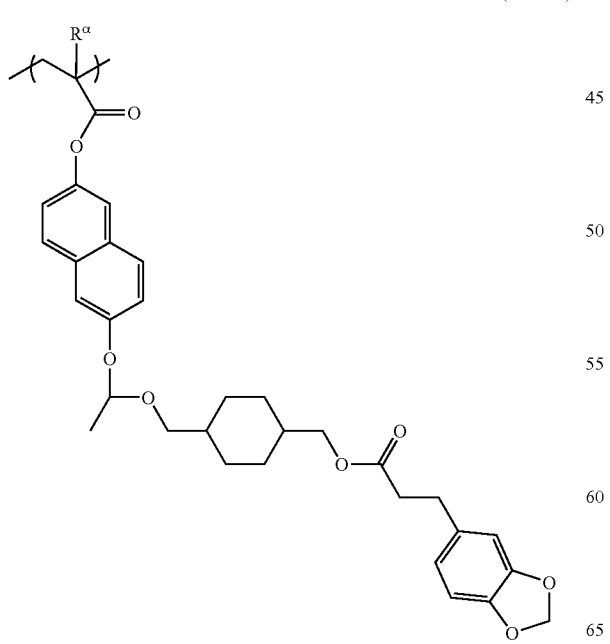
[Chemical Formula 19]
(a0-1-51)
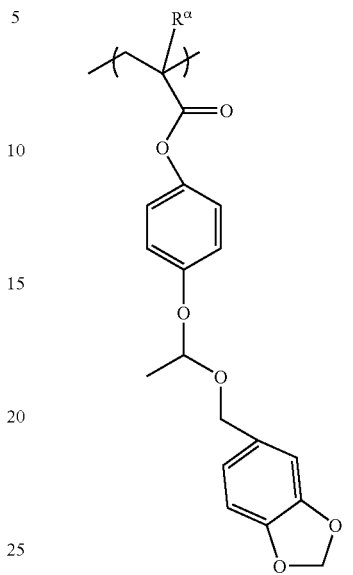
(a0-1-52)
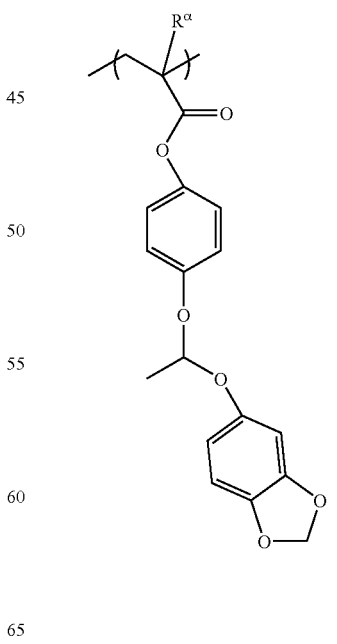

(a0-1-53)
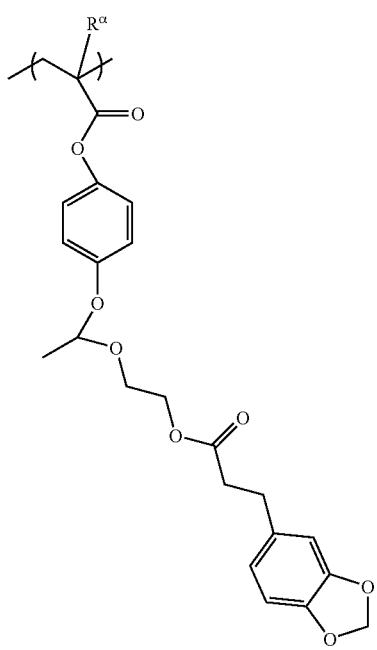
(a0-1-55)
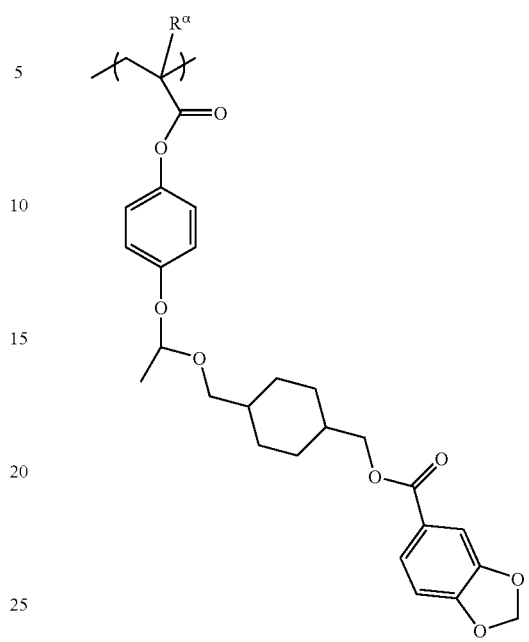
(a0-1-54)
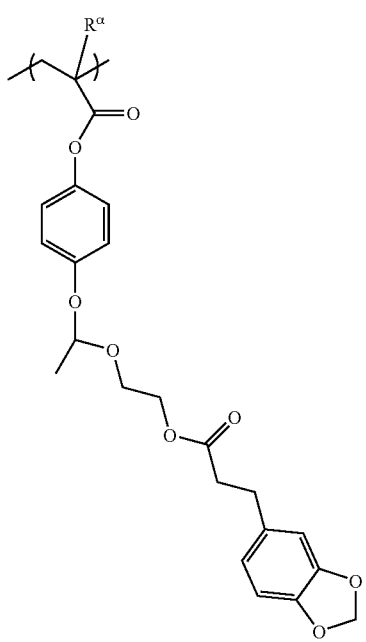
(a0-1-56)

(a0-1-57)
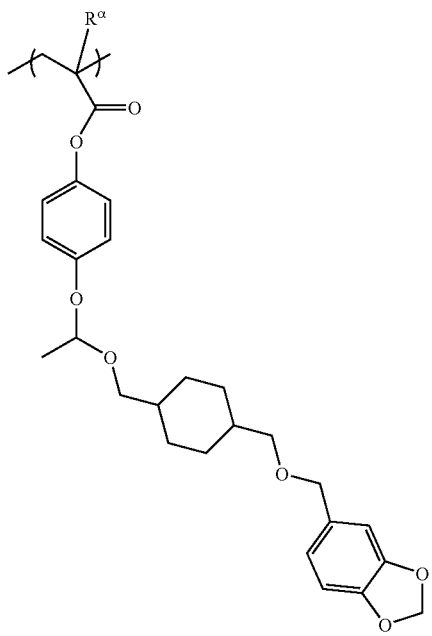
(a0-1-59)
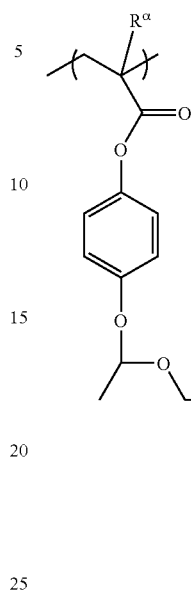
(a0-1-58)
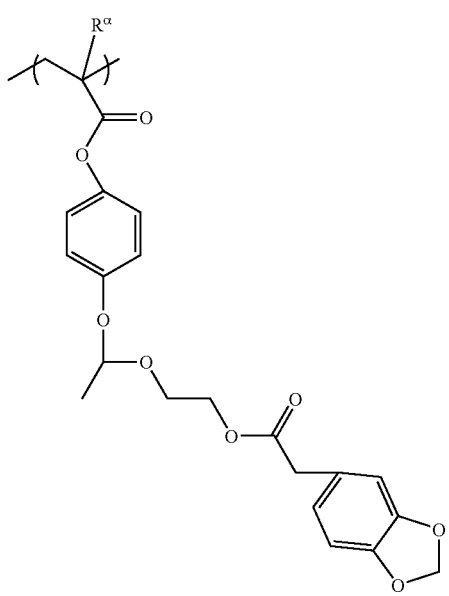
[Chemical Formula 20]
(a0-1-61)
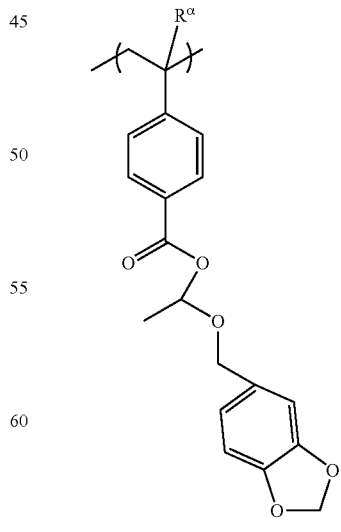

(a0-1-62)
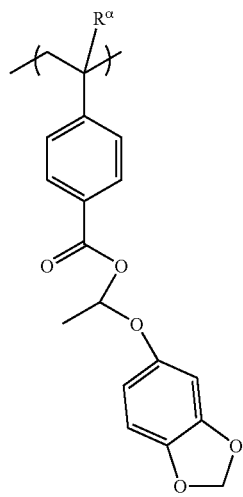
(a0-1-63)
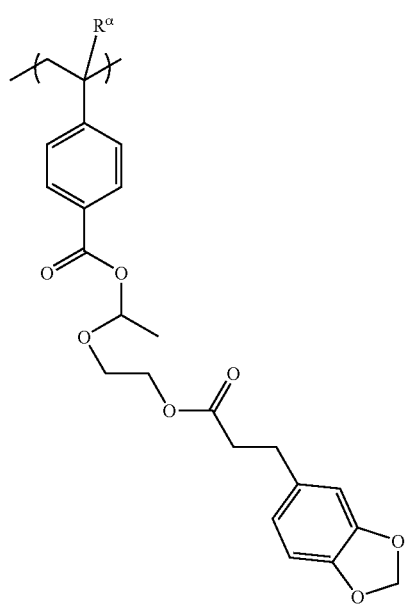
(a0-1-64)
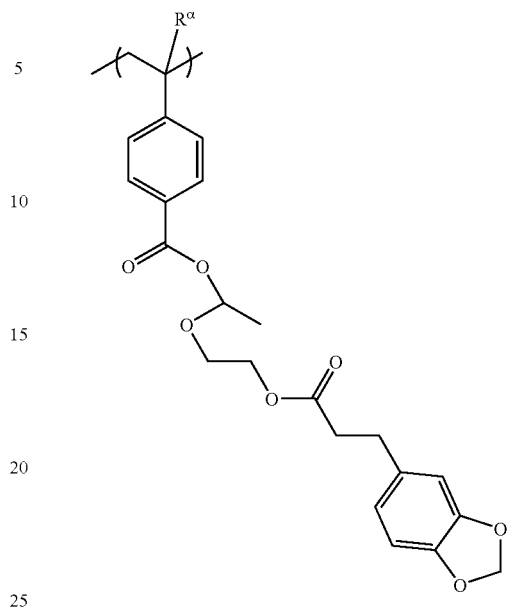
(a0-1-65)
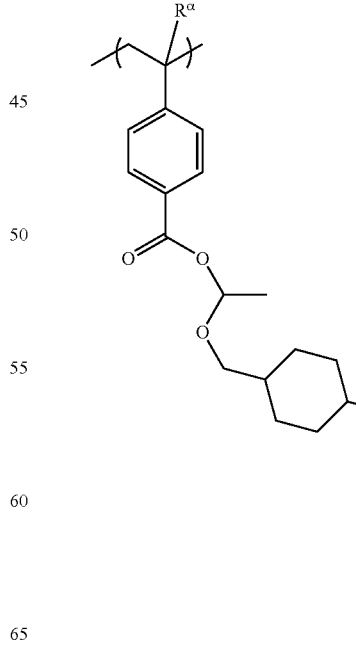

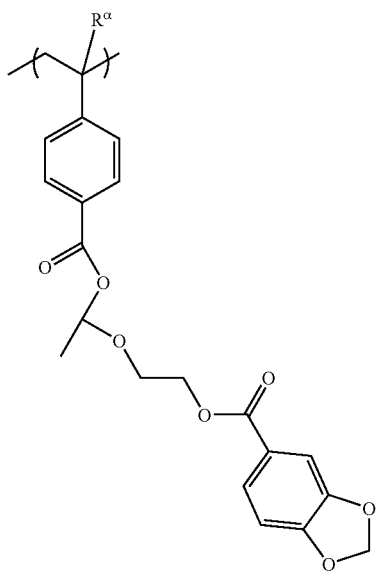
(a0-1-66)

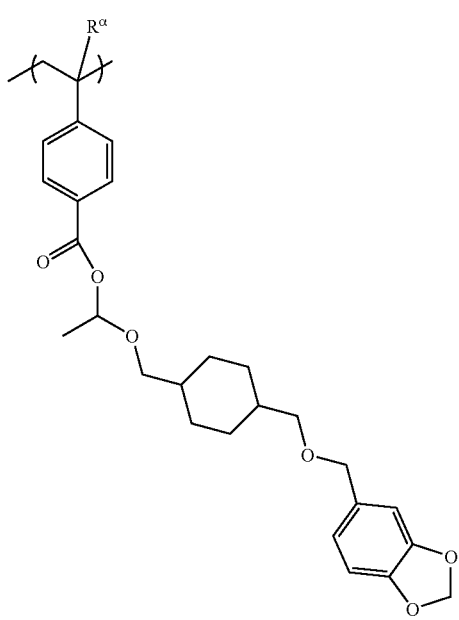
(a0-1-67)

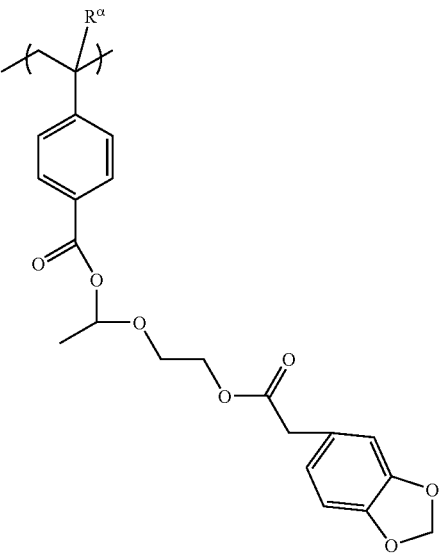
(a0-1-68)

(a0-1-69)

In the component (A1), as the structural unit (a0), either a single type of structural unit may be used alone, or a combination of two or more types of structural units may be used.

Of the various possibilities described above, the structural unit (a0) is preferably a structural unit represented by the above general formula (a0-1').

Further, the structural unit (a0) is preferably at least one unit selected from the group consisting of the structural unit (a01), the structural unit (a02), the structural unit (a03), the structural unit (a04), the structural unit (a05) and the structural unit (a06). The structural unit (a01) and the structural unit (a06) are particularly desirable.

The amount of the structural unit (a0) within the component (A1), based on the combined total of all the structural units that constitute the component (A1), is preferably within a range from 5 to 60 mol %, more preferably from 5 to 50 mol %, and still more preferably from 10 to 40 mol %. By ensuring that this amount is at least as large as the lower limit of the above range, a higher level of resolution can be obtained. Further, a resist pattern of more favorable shape, with reduced line width roughness (LWR), can be formed. On the other hand, by ensuring that the amount is not more than the upper limit of the above range, a good balance can be achieved with the other structural units.

Structural Unit (a5)

The structural unit (a5) is a structural unit derived from a hydroxystyrene.

Including the structural unit (a5) within the component (A1) improves the dry etching resistance in addition to the other effects of the present invention. Moreover, the structural unit (a5) also offers other advantages such as the ready availability and low cost of the hydroxystyrene that functions as the raw material for the structural unit.

The structural unit (a5) may be any structural unit generated by cleavage of the ethylenic double bond of a hydroxystyrene, a hydroxystyrene in which the α-position hydrogen atom has been substituted with a substituent such as an alkyl group, or a derivative of one of these hydroxystyrenes.

Preferred examples of the structural unit (a5) include structural units represented by general formula (a5-1) shown below.

[Chemical Formula 21]

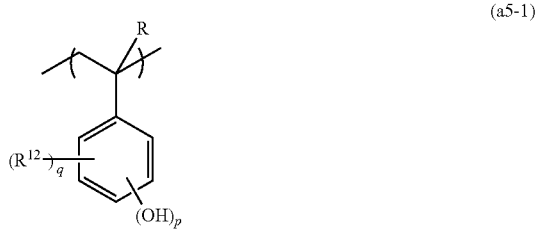

(a5-1)

In formula (a5-1), R represents a hydrogen atom, an alkyl group of 1 to 5 carbon atoms or a halogenated alkyl group of 1 to 5 carbon atoms, $R^{12}$ represents a halogen atom, an alkyl group of 1 to 5 carbon atoms or a halogenated alkyl group of 1 to 5 carbon atoms, p represents an integer of 1 to 3, and q represents an integer of 0 to 4, provided that p+q is an integer of 1 to 5.

In formula (a5-1), R, $R^{12}$, p and q are the same as defined above for R, $R^{12}$, p and q in formula (a0-1-10).

In the component (A1), as the structural unit (a5), either a single type of structural unit may be used alone, or a combination of two or more types of structural units may be used.

The amount of the structural unit (a5) within the component (A1), based on the combined total of all the structural units that constitute the component (A1), is preferably within a range from 40 to 95 mol %, more preferably from 45 to 90 mol %, still more preferably from 50 to 85 mol %, and most preferably from 55 to 80 mol %. By ensuring that this amount is at least as large as the lower limit of the above range, an appropriate level of alkali solubility can be obtained. Further, the effects achieved by including the structural unit (a5) are able to manifest satisfactorily. On the other hand, by ensuring that the amount is not more than the upper limit of the above range, a good balance can be achieved with the other structural units.

Other Structural Units

The component (A1) may also include other structural units besides the structural unit (a0) and the structural unit (a5), provided the inclusion of these other structural units does not impair the effects of the present invention.

There are no particular limitations on these other structural units, and any other structural unit which cannot be classified as one of the above structural units (a0) or (a5) can be used without any particular limitations. Any of the multitude of conventional structural units used within resist resins for ArF excimer lasers or KrF excimer lasers can be used.

Examples of these other structural units include a structural unit (a1) derived from an acrylate ester containing an acid-dissociable, dissolution-inhibiting group (but excluding the above structural unit (a0)), a structural unit (a2) derived from an acrylate ester containing a lactone-containing cyclic group, a structural unit (a3) derived from an acrylate ester containing a polar group-containing aliphatic hydrocarbon group, a structural unit (a4) derived from an acrylate ester containing a non-acid-dissociable aliphatic polycyclic group, a structural unit (a6) derived from a styrene, a structural unit (a7) derived from a hydroxystyrene in which at least a portion of the hydroxyl group hydrogen atoms have been protected with a substituent, a structural unit (a8) derived from a vinylnaphthol, and a structural unit (a9) derived from a vinylbenzoic acid.

Structural Unit (a1)

The structural unit (a1) is a structural unit derived from an acrylate ester containing an acid-dissociable, dissolution-inhibiting group that does not fall under the category of the aforementioned structural unit (a0).

The acid-dissociable, dissolution-inhibiting group within the structural unit (a1) is a group that has an alkali dissolution-inhibiting effect that renders the entire component (A1) substantially insoluble in an alkali developing solution prior to dissociation, but then dissociates under the action of acid, resulting in an increase in the solubility of the entire component (A1) in the alkali developing solution. As this acid-dissociable, dissolution-inhibiting group, any of the groups that have been proposed as acid-dissociable, dissolution-inhibiting groups for the base resins of chemically amplified resists can be used. Generally, groups that form either a cyclic or chain-like tertiary alkyl ester with the carboxyl group of the (meth)acrylic acid or the like, and acetal-type acid-dissociable, dissolution-inhibiting groups such as alkoxyalkyl groups are the most widely known.

Here, a "tertiary alkyl ester" describes a structure in which an ester is formed by substituting the hydrogen atom of a carboxyl group with a chain-like or cyclic alkyl group, and a tertiary carbon atom within the chain-like or cyclic alkyl group is bonded to the oxygen atom at the terminal of the carbonyloxy group (—C(O)—O—). In this tertiary alkyl ester, the action of acid causes cleavage of the bond between the oxygen atom and the tertiary carbon atom.

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid-dissociable, dissolution-inhibiting groups".

Examples of tertiary alkyl ester-type acid-dissociable, dissolution-inhibiting groups include aliphatic branched, acid-dissociable, dissolution-inhibiting groups and aliphatic cyclic group-containing acid-dissociable, dissolution-inhibiting groups.

In the present description and claims, the term "aliphatic" is a relative concept used in relation to the term "aromatic", and defines a group or compound or the like that has no aromaticity.

The term "aliphatic branched" refers to a branched structure having no aromaticity.

The "aliphatic branched, acid-dissociable, dissolution-inhibiting group" is not limited to groups constituted solely of carbon atoms and hydrogen atoms (not limited to hydrocarbon groups), but is preferably a hydrocarbon group.

Further, the "hydrocarbon group" may be either saturated or unsaturated, but is preferably saturated.

The aliphatic branched, acid-dissociable, dissolution-inhibiting group is preferably a tertiary alkyl group of 4 to 8 carbon atoms, and specific examples thereof include a tert-butyl group, tert-pentyl group or tert-heptyl group.

The term "aliphatic cyclic group" refers to a monocyclic group or polycyclic group that has no aromaticity.

The "aliphatic cyclic group" in the structural unit (a1) may or may not have a substituent. Examples of the substituent include lower alkyl groups of 1 to 5 carbon atoms, lower alkoxy groups of 1 to 5 carbon atoms, a fluorine atom, fluorinated lower alkyl groups of 1 to 5 carbon atoms, and an oxygen atom (=O).

The basic ring of the "aliphatic cyclic group" excluding substituents is not limited to groups constituted solely from carbon and hydrogen (not limited to hydrocarbon groups), but is preferably a hydrocarbon group. Further, the "hydrocarbon group" may be either saturated or unsaturated, but is preferably saturated. The "aliphatic cyclic group" is preferably a polycyclic group.

Examples of such aliphatic cyclic groups include groups in which one or more hydrogen atoms have been removed from a monocycloalkane or a polycycloalkane such as a bicycloalkane, tricycloalkane or tetracycloalkane, which may or may not be substituted with a lower alkyl group, a fluorine atom or a fluorinated lower alkyl group. Specific examples include groups in which one or more hydrogen atoms have been removed from a monocycloalkane such as cyclopentane or cyclohexane, or a polycycloalkane such as adamantane, norbornane, isobornane, tricyclodecane or tetracyclododecane.

Examples of the aliphatic cyclic group-containing acid-dissociable, dissolution-inhibiting group include groups having a tertiary carbon atom within the ring structure of a cyclic alkyl group. Specific examples include a 2-methyl-2-adamantyl group and a 2-ethyl-2-adamantyl group. Alternatively, groups having an aliphatic cyclic group such as an adamantyl group, cyclohexyl group, cyclopentyl group, norbornyl group, tricyclodecyl group or tetracyclododecyl group, and a branched alkylene group having a tertiary carbon atom bonded thereto, such as the groups bonded to the oxygen atom of the carbonyloxy group (—C(O)—O—) in the structural units represented by general formulas (a1"-1) to (a1"-6) shown below, may also be used.

[Chemical Formula 22]

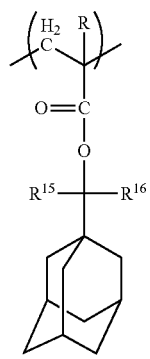

(a1"-1)

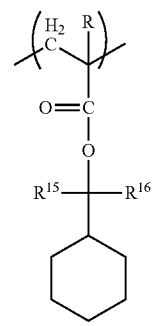

(a1"-2)

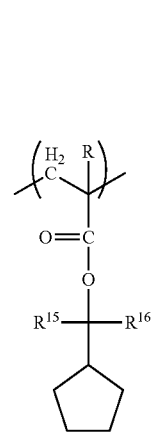

(a1"-3)

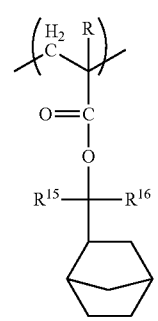

(a1"-4)

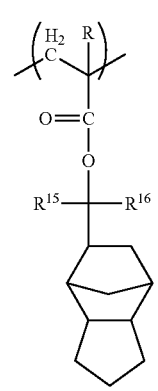

(a1"-5)

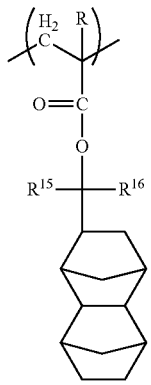

(a1″-6)

In the above formulas, each R independently represents a hydrogen atom, a lower alkyl group or a halogenated lower alkyl group, and each of $R^{15}$ and $R^{16}$ independently represents an alkyl group (which may be linear or branched, and preferably has 1 to 5 carbon atoms).

In general formulas (a1″-1) to (a1″-6), the lower alkyl group or halogenated lower alkyl group for R is the same as defined for the lower alkyl group or halogenated lower alkyl group that may be bonded to the α-position of an aforementioned acrylate ester.

An "acetal-type acid-dissociable, dissolution-inhibiting group" generally substitutes a hydrogen atom at the terminal of an alkali-soluble group such as a carboxyl group or hydroxyl group, so as to be bonded with an oxygen atom. When acid is generated upon exposure, this generated acid acts to break the bond between the acetal-type acid-dissociable, dissolution-inhibiting group and the oxygen atom to which the acetal-type, acid-dissociable, dissolution-inhibiting group is bonded.

Examples of acetal-type acid-dissociable, dissolution-inhibiting groups include groups represented by general formula (p1) shown below.

[Chemical Formula 23]

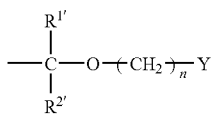

(p1)

In the formula, $R^{1\prime}$, $R^{2\prime}$ and n are the same as defined above, and Y represents a lower alkyl group or an aliphatic cyclic group.

In the above formula, n represents an integer of 0 to 3, is preferably an integer of 0 to 2, more preferably 0 or 1, and is most preferably 0.

Each of $R^{1\prime}$ and $R^{2\prime}$ independently represents a hydrogen atom or a lower alkyl group.

Examples of the lower alkyl group for $R^{1\prime}$ and $R^{2\prime}$ include the same lower alkyl groups as those listed above for R, although a methyl group or ethyl group is preferable, and a methyl group is particularly desirable.

In the present invention, it is preferable that at least one of $R^{1\prime}$ and $R^{2\prime}$ is a hydrogen atom. That is, it is preferable that the acid-dissociable, dissolution-inhibiting group (p1) is a group represented by general formula (p1-1) shown below.

[Chemical Formula 24]

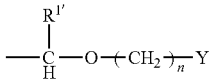

(p1-1)

In the formula, $R^{1\prime}$, n and Y are the same as defined above.

Examples of the lower alkyl group for Y include the same groups as those listed above for the lower alkyl group for R.

As the aliphatic cyclic group for Y, any of the monocyclic or polycyclic aliphatic cyclic groups which have been proposed for conventional ArF resists and the like can be appropriately selected for use. For example, the same groups described above in connection with the "aliphatic cyclic group" can be used.

Further, as the acetal-type, acid-dissociable, dissolution-inhibiting group, groups represented by general formula (p2) shown below may also be used.

[Chemical Formula 25]

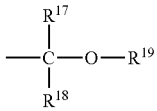

(p2)

In the formula, $R^{17}$ and $R^{18}$ are the same as defined above, and $R^{19}$ represents a linear, branched or cyclic alkyl group. Alternatively, each of $R^{17}$ and $R^{19}$ may independently represent a linear or branched alkylene group, wherein $R^{17}$ is bonded to $R^{19}$ to form a ring.

In the above formula (p2), each of $R^{17}$ and $R^{18}$ represents a linear or branched alkyl group or a hydrogen atom.

The alkyl group for $R^{17}$ or $R^{18}$ preferably has 1 to 15 carbon atoms, and may be either linear or branched. As the alkyl group, an ethyl group or a methyl group is preferable, and a methyl group is most preferable. It is particularly desirable that one of $R^{17}$ and $R^{18}$ is a hydrogen atom and the other is a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cyclic alkyl group, it preferably has 4 to 15 carbon atoms, more preferably 4 to 12 carbon atoms, and most preferably 5 to 10 carbon atoms. Examples of the cyclic alkyl group include groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group. Specific examples include groups in which one or more hydrogen atoms have been removed from a monocycloalkane such as cyclopentane and cyclohexane, or a polycycloalkane such as adamantane, norbornane, isobornane, tricyclodecane or tetracyclododecane. Among these, a group in which one or more hydrogen atoms have been removed from adamantane is preferable.

In formula (p2) above, each of $R^{17}$ and $R^{19}$ may independently represent a linear or branched alkylene group (and preferably an alkylene group of 1 to 5 carbon atoms), wherein $R^{19}$ is bonded to $R^{17}$.

In such a case, a cyclic group is formed by $R^{17}$, $R^{19}$, the oxygen atom having $R^{19}$ bonded thereto, and the carbon atom having the oxygen atom and $R^{17}$ bonded thereto. Such a cyclic group is preferably a 4- to 7-membered ring, and more preferably a 4- to 6-membered ring. Specific examples of this cyclic group include a tetrahydropyranyl group and a tetrahydrofuranyl group.

As the structural unit (a1), it is preferable to use at least one type of structural unit selected from the group consisting of structural units represented by general formula (a1-0-1) shown below and structural units represented by general formula (a1-0-2) shown below.

[Chemical Formula 26]

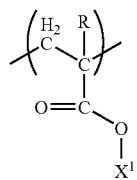

(a1-0-1)

In the formula, R represents a hydrogen atom, a lower alkyl group or a halogenated lower alkyl group, and $X^1$ represents an acid-dissociable, dissolution-inhibiting group.

[Chemical Formula 27]

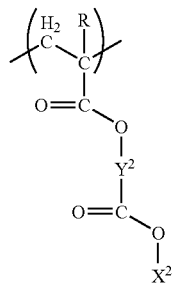

(a1-0-2)

In the formula, R represents a hydrogen atom, a lower alkyl group or a halogenated lower alkyl group, $X^2$ represents an acid-dissociable, dissolution-inhibiting group, and $Y^2$ represents a divalent linking group.

In general formula (a1-0-1), the lower alkyl group or halogenated lower alkyl group for R is the same as defined above for the lower alkyl group or halogenated lower alkyl group that may be bonded to the α-position of an aforementioned acrylate ester.

$X^1$ is not particularly limited, as long as it is an acid-dissociable, dissolution-inhibiting group. Examples include the aforementioned tertiary alkyl ester-type acid-dissociable, dissolution-inhibiting groups and acetal-type acid-dissociable, dissolution-inhibiting groups, and of these, tertiary alkyl ester-type acid-dissociable, dissolution-inhibiting groups are preferable.

In general formula (a1-0-2), R is the same as defined above. $X^2$ is the same as defined for $X^1$ in formula (a1-0-1).

Examples of the divalent linking group for $Y^2$ include alkylene groups, divalent aliphatic cyclic groups, and divalent linking groups containing a hetero atom.

Examples of the aliphatic cyclic group include the same groups as those exemplified above within the description of the "aliphatic cyclic group" with the exception that two or more hydrogen atoms have been removed therefrom.

When $Y^2$ represents an alkylene group, the group preferably contains 1 to 10 carbon atoms, more preferably 1 to 6 carbon atoms, still more preferably 1 to 4 carbon atoms, and most preferably 1 to 3 carbon atoms.

When $Y^2$ represents a divalent aliphatic cyclic group, it is particularly desirable that the divalent aliphatic cyclic group is a group in which two or more hydrogen atoms have been removed from cyclopentane, cyclohexane, norbornane, isobornane, adamantine, tricyclodecane or tetracyclododecane.

When $Y^2$ represents a divalent linking group containing a hetero atom, examples of the divalent linking group containing a hetero atom include —O—, —C(=O)—O—, —C(=O)—, —O—C(=O)—O—, —C(=O)—NH—, —NH— (wherein H may be replaced with a substituent such as an alkyl group or acyl group or the like), —S—, —S(=O)$_2$—, —S(=O)$_2$—O—, and -A-O (oxygen atom)-B— (wherein each of A and B independently represents a divalent hydrocarbon group which may have a substituent).

In those cases where $Y^2$ is —NH— and the H has been replaced with a substituent such as an alkyl group or acyl group or the like, the number of carbon atoms within the substituent is preferably from 1 to 10 carbon atoms, more preferably from 1 to 8 carbon atoms, and most preferably from 1 to 5 carbon atoms.

When $Y^2$ represents -A-O—B—, each of A and B independently represents a divalent hydrocarbon group that may have a substituent.

The description that the hydrocarbon group "may have a substituent" means that some or all of the hydrogen atoms within the hydrocarbon group may be substituted with an atom other than a hydrogen atom or with a group.

The hydrocarbon group for A may be either an aliphatic hydrocarbon group or an aromatic hydrocarbon group. An "aliphatic hydrocarbon group" refers to a hydrocarbon group that has no aromaticity.

The aliphatic hydrocarbon group for A may be saturated or unsaturated. In general, the aliphatic hydrocarbon group is preferably saturated.

Specific examples of the aliphatic hydrocarbon group include linear and branched aliphatic hydrocarbon groups, and aliphatic hydrocarbon groups containing a ring in the structure thereof.

The linear or branched aliphatic hydrocarbon group preferably has 1 to 10 carbon atoms, more preferably 1 to 8, still more preferably 1 to 5, and most preferably 1 or 2 carbon atoms.

As the linear aliphatic hydrocarbon group, a linear alkylene group is preferable. Specific examples thereof include a methylene group, an ethylene group [—(CH$_2$)$_2$—], a trimethylene group [—(CH$_2$)$_3$—], a tetramethylene group [—(CH$_2$)$_4$—] and a pentamethylene group [—(CH$_2$)$_5$—].

As the branched aliphatic hydrocarbon group, a branched alkylene group is preferable, and specific examples include alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, and —C(CH$_2$CH$_3$)$_2$—; alkylethylene groups such as —CH(CH$_3$)CH$_2$—, —CH(CH$_3$)CH (CH$_3$)—, —C(CH$_3$)$_2$CH$_2$— and —CH(CH$_2$CH$_3$)CH$_2$—; alkyltrimethylene groups such as —CH(CH$_3$)CH$_2$CH$_2$—, and —CH$_2$CH(CH$_3$)CH$_2$—; and alkyltetramethylene groups such as —CH(CH$_3$)CH$_2$CH$_2$CH$_2$—, and —CH$_2$CH(CH$_3$)

$CH_2CH_2$—. As the alkyl group within the alkylalkylene group, a linear alkyl group of 1 to 5 carbon atoms is preferable.

The linear or branched aliphatic hydrocarbon group (chain-like aliphatic hydrocarbon group) may or may not have a substituent. Examples of substituents include a fluorine atom, a fluorinated lower alkyl group of 1 to 5 carbon atoms, and an oxygen atom (=O).

Examples of the hydrocarbon group containing a ring in the structure thereof include cyclic aliphatic hydrocarbon groups (groups in which two hydrogen atoms have been removed from an aliphatic hydrocarbon ring), and groups in which this type of cyclic aliphatic hydrocarbon group is either bonded to the terminal of an aforementioned chain-like aliphatic hydrocarbon group, or interposed within the chain of an aforementioned chain-like aliphatic hydrocarbon group.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic group, a group in which two hydrogen atoms have been removed from a monocycloalkane of 3 to 6 carbon atoms is preferable. Specific examples of the monocycloalkane include cyclopentane and cyclohexane. As the polycyclic group, a group in which two hydrogen atoms have been removed from a polycycloalkane of 7 to 12 carbon atoms is preferable. Specific examples of the polycycloalkane include adamantane, norbornane, isobornane, tricyclodecane and tetracyclododecane.

The cyclic aliphatic hydrocarbon group may or may not have a substituent. Examples of the substituent include lower alkyl groups of 1 to 5 carbon atoms, a fluorine atom, fluorinated lower alkyl groups of 1 to 5 carbon atoms, and an oxygen atom (=O).

As the group A, a linear aliphatic hydrocarbon group is preferred, a linear alkylene group is more preferred, a linear alkylene group of 2 to 5 carbon atoms is still more preferred, and an ethylene group is the most desirable.

Examples of the hydrocarbon group for B include the same divalent hydrocarbon groups as those listed above for A.

As the group B, a linear or branched aliphatic hydrocarbon group is preferred, and a methylene group or an alkylmethylene group is particularly desirable.

The alkyl group within the alkylmethylene group is preferably a linear alkyl group of 1 to 5 carbon atoms, more preferably a linear alkyl group of 1 to 3 carbon atoms, and is most preferably a methyl group.

Specific examples of the structural unit (a1) include structural units represented by general formulas (a1-1) to (a1-4) shown below.

[Chemical Formula 28]

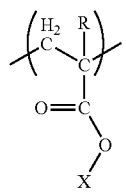
(a1-1)

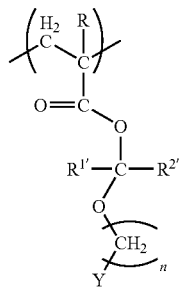
(a1-2)

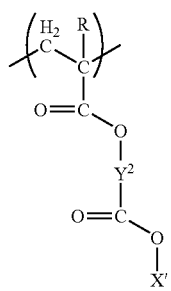
(a1-3)

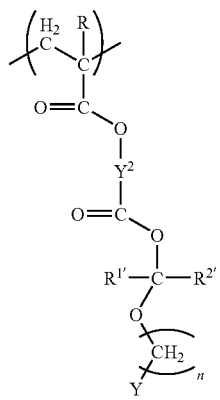
(a1-4)

In the formulas, X' represents a tertiary alkyl ester-type acid-dissociable, dissolution-inhibiting group, Y represents a lower alkyl group of 1 to 5 carbon atoms or an aliphatic cyclic group, n represents an integer of 0 to 3, $Y^2$ represents a divalent linking group, R is the same as defined above, and each of $R^{1'}$ and $R^{2'}$ independently represents a hydrogen atom or a lower alkyl group of 1 to 5 carbon atoms.

In the formulas, examples of X' include the same groups as the tertiary alkyl ester-type acid-dissociable, dissolution-inhibiting groups described above for $X^1$.

Examples of $R^{1'}$, $R^{2'}$, n and Y include the same groups and numbers as those listed above for $R^{1'}$, $R^{2'}$, n and Y in general formula (p1) described above in connection with the "acetal-type acid-dissociable, dissolution-inhibiting groups".

Examples of $Y^2$ include the same groups as those listed above for $Y^2$ in general formula (a1-0-2).

Specific examples of structural units represented by general formulas (a1-1) to (a1-4) are shown below.

In each of the formulas shown below, $R^\alpha$ represents a hydrogen atom, a methyl group or a trifluoromethyl group.

[Chemical Formula 29]
(a1-1-1)
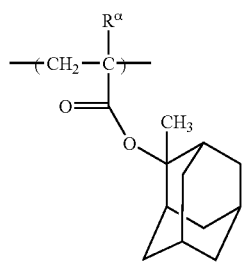
(a1-1-2)
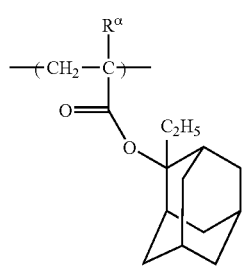
(a1-1-3)
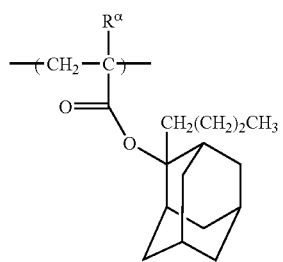
(a1-1-4)
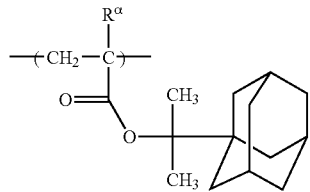
(a1-1-5)
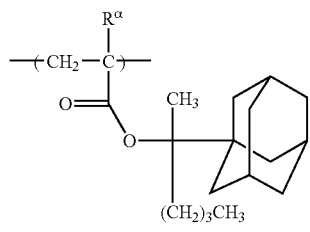
(a1-1-6)
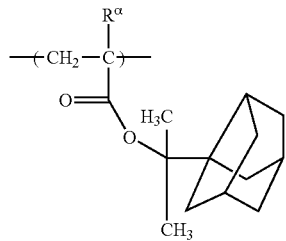
(a1-1-7)
(a1-1-8)
(a1-1-9)
[Chemical Formula 30]
(a1-1-10)
(a1-1-11)
(a1-1-12)

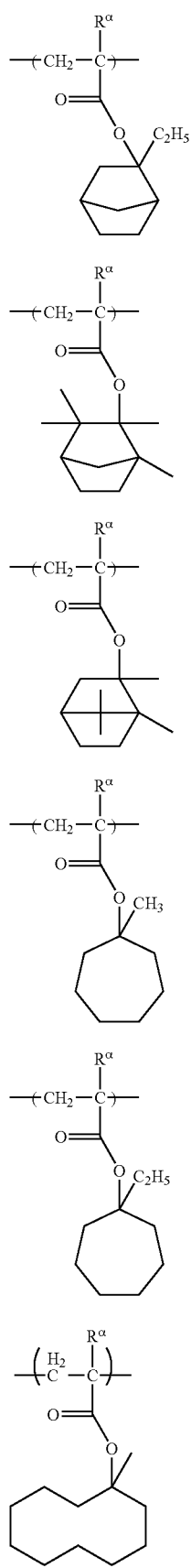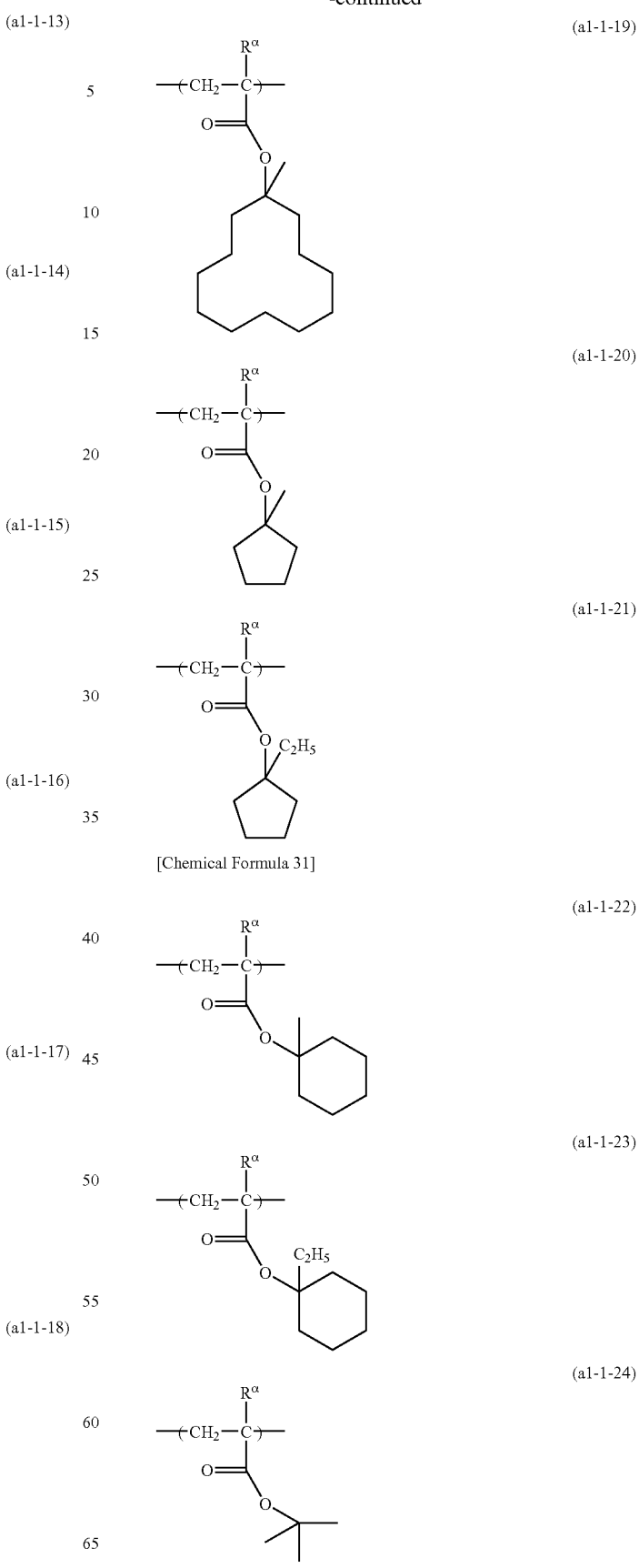

(a1-1-25) 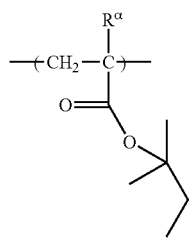
(a1-1-26) 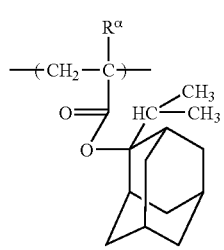
(a1-1-27) 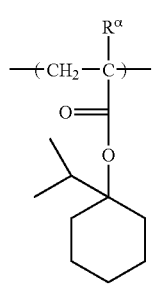
(a1-1-28) 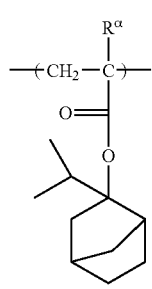
(a1-1-29) 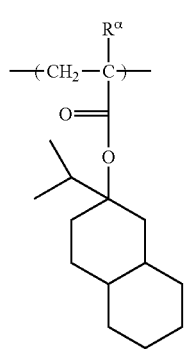
(a1-1-30) 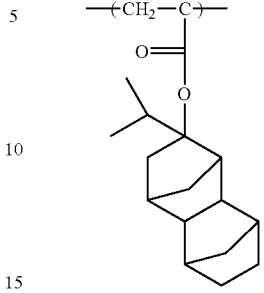
(a1-1-31) 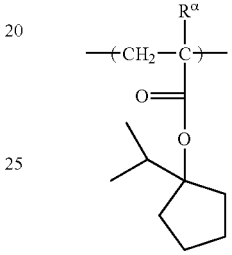
[Chemical Formula 32]
(a1-2-1) 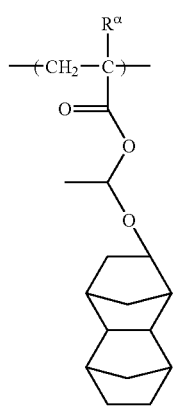
(a1-2-2) 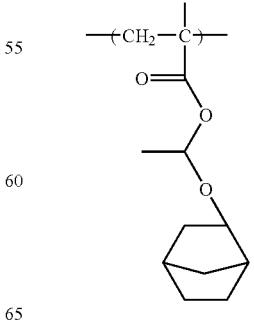

(a1-2-3) 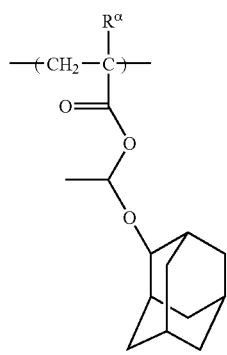
(a1-2-4) 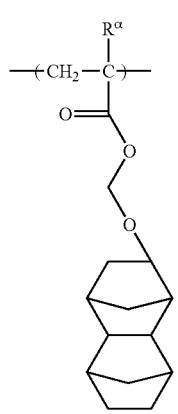
(a1-2-5) 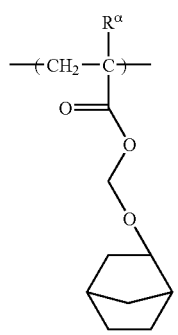
(a1-2-6) 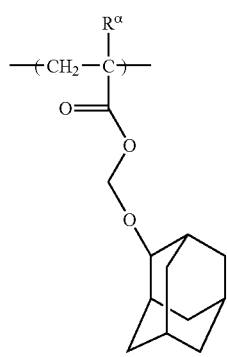
(a1-2-7) 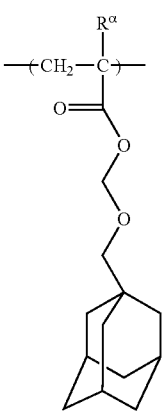
(a1-2-8) 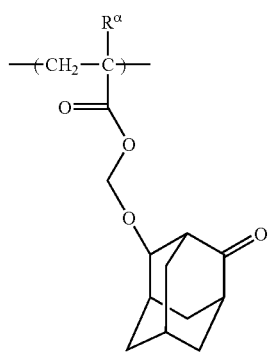
(a1-2-9) 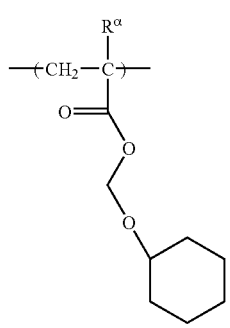
(a1-2-10) 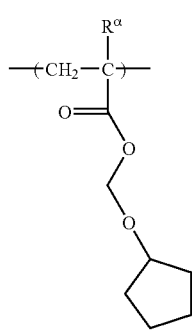

(a1-2-11) 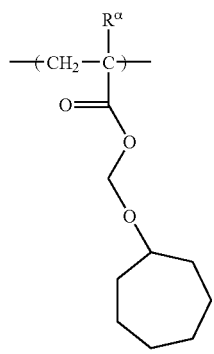
(a1-2-12) 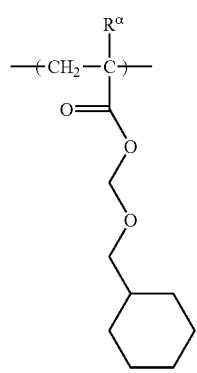
(a1-2-13) 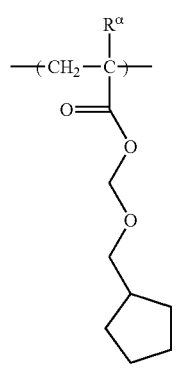
(a1-2-14) 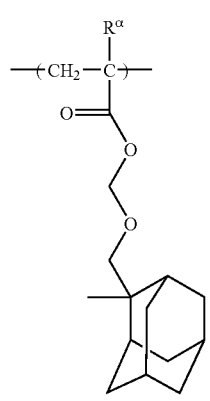
(a1-2-15) 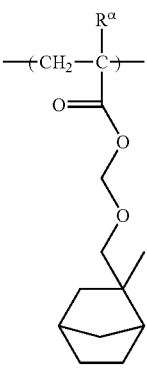
(a1-2-16) 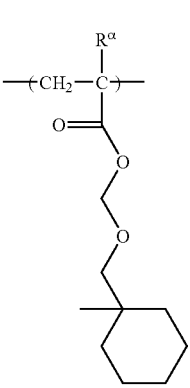
(a1-2-17) 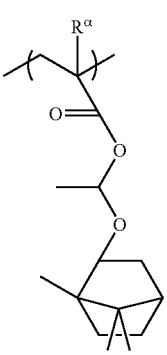
(a1-2-18) 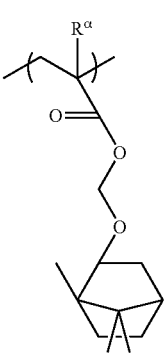

(a1-2-19)
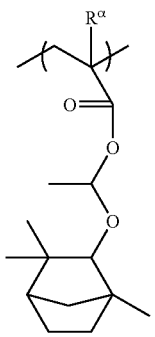
(a1-2-20)
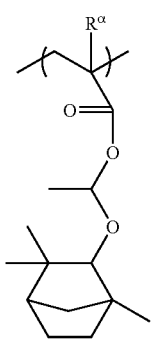
(a1-2-21)
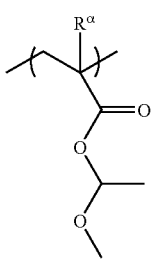
(a1-2-22)
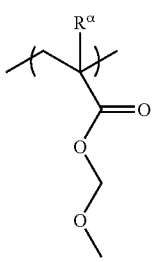
(a1-2-23)
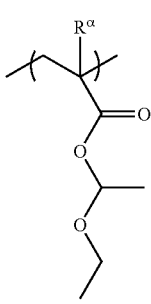
(a1-2-24)
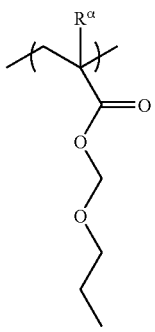
[Chemical Formula 33]
(a1-3-1)
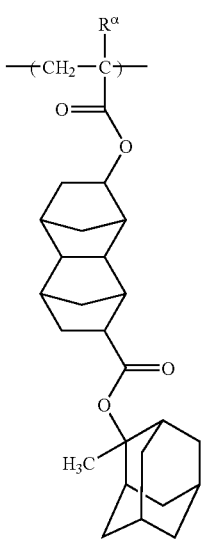
(a1-3-2)
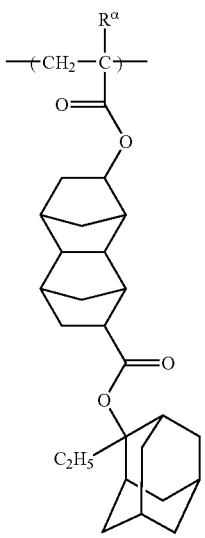

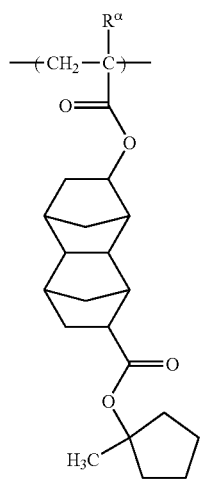
(a1-3-3)
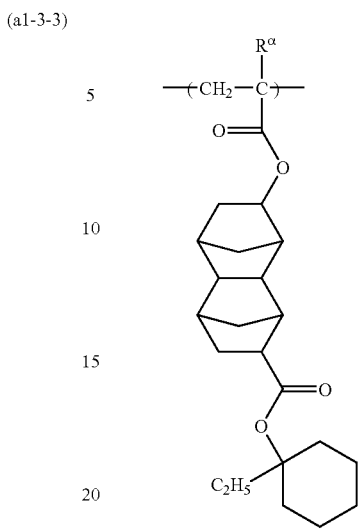
(a1-3-6)
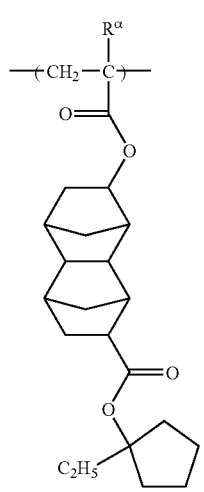
(a1-3-4)
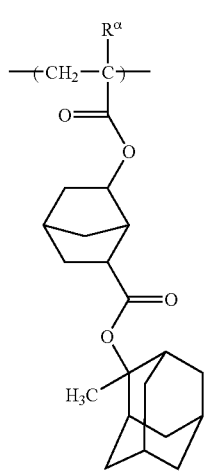
(a1-3-7)
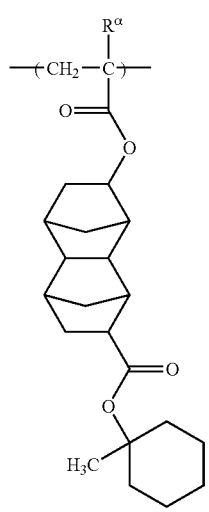
(a1-3-5)
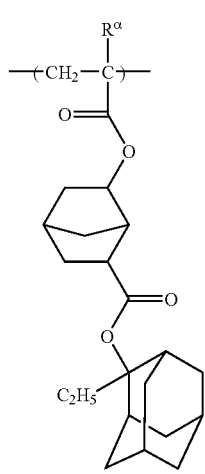
(a1-3-8)

(a1-3-9)
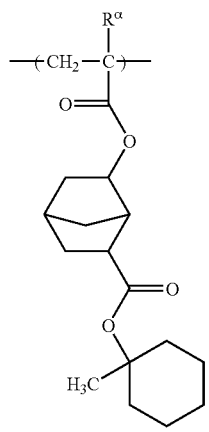
(a1-3-10)
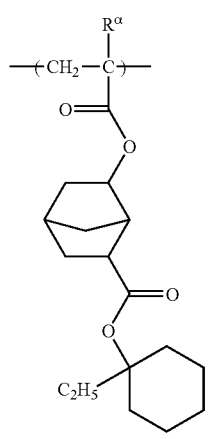
(a1-3-11)
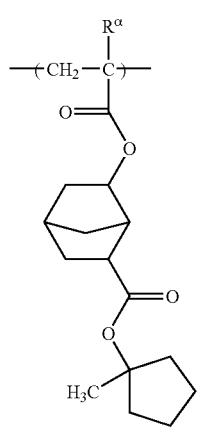
(a1-3-12)
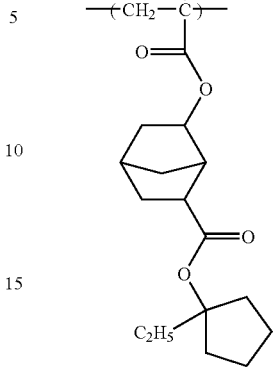
(a1-3-13)
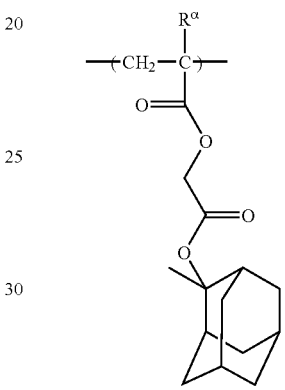
(a1-3-14)
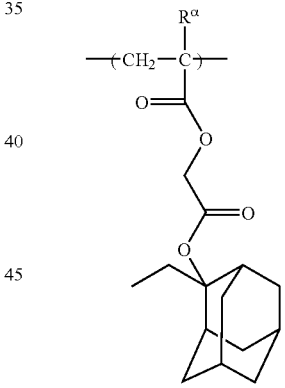
(a1-3-15)
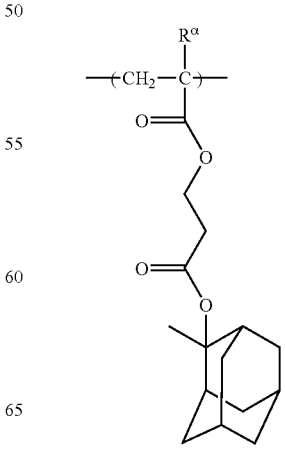

(a1-3-16)
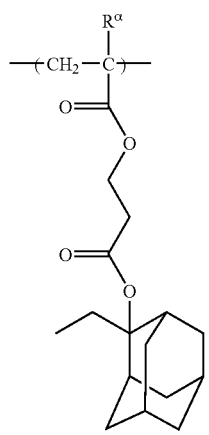
(a1-3-17)
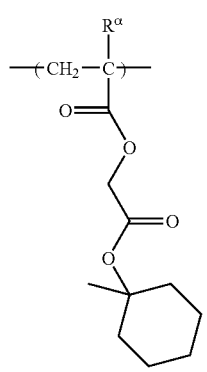
(a1-3-18)
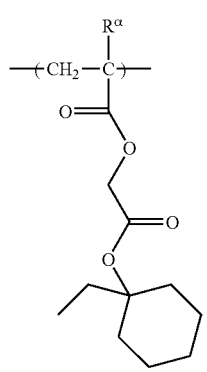
[Chemical Formula 34]
(a1-3-19)
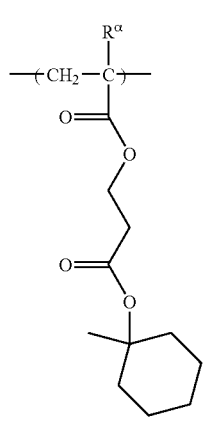
(a1-3-20)
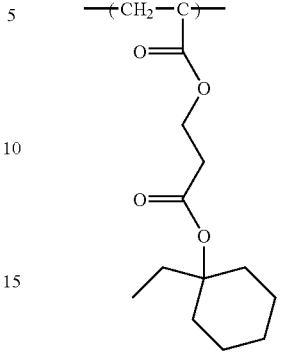
(a1-3-21)
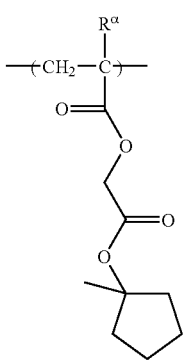
(a1-3-22)
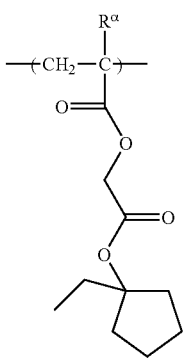
(a1-3-23)
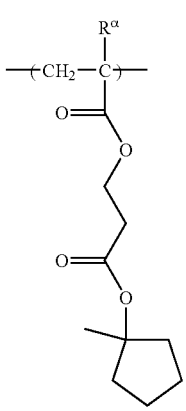

(a1-3-24) 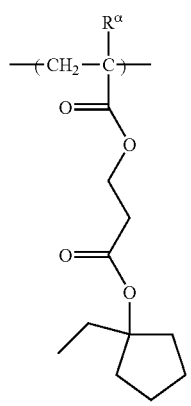
[Chemical Formula 35]
(a1-3-25) 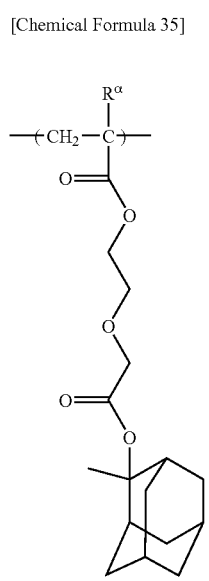
(a1-3-26) 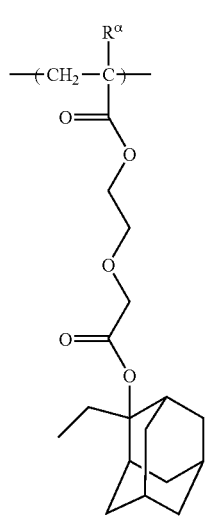
(a1-3-27) 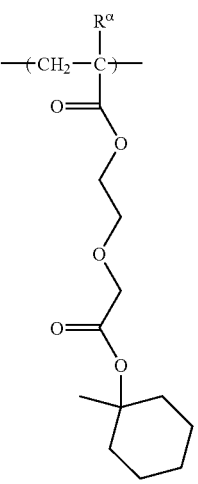
(a1-3-28) 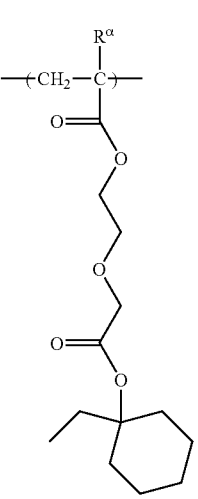
(a1-3-29) 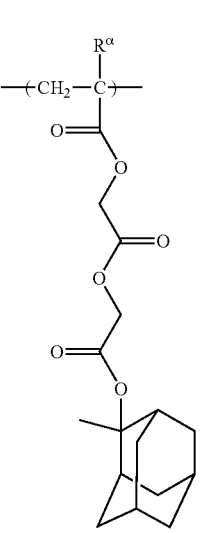

(a1-3-30)
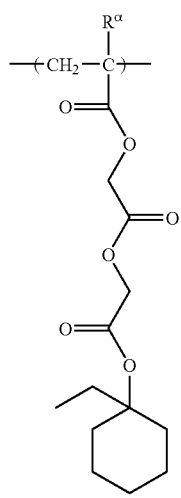
(a1-3-31)
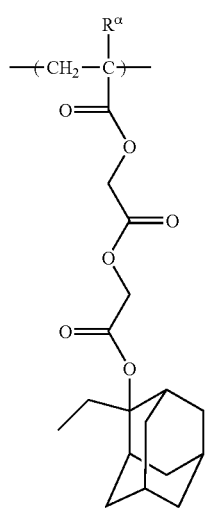
(a1-3-32)
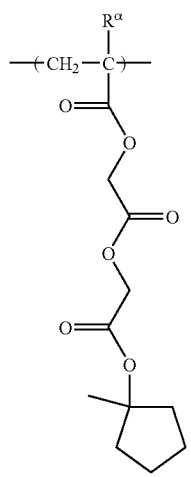
[Chemical Formula 36]
(a1-4-1)
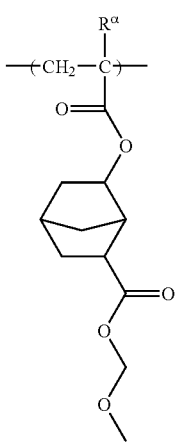
(a1-4-2)
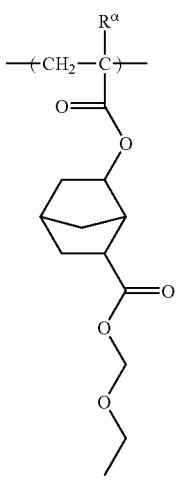
(a1-4-3)
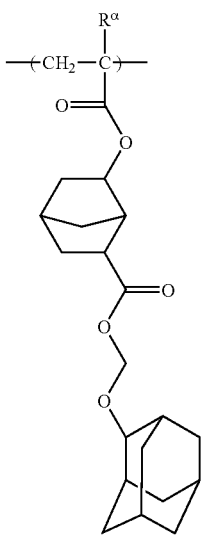

(a1-4-4) 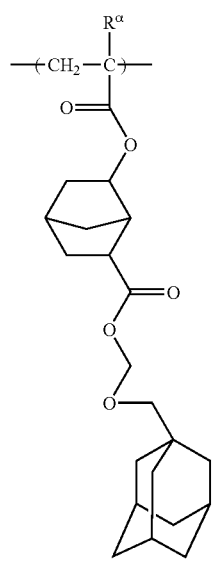
(a1-4-5) 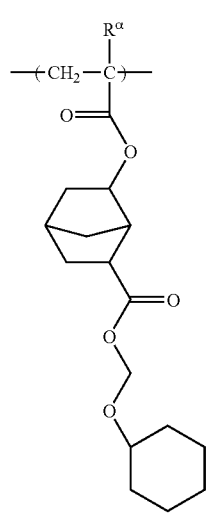
(a1-4-6) 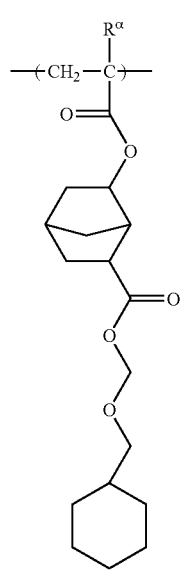
(a1-4-7) 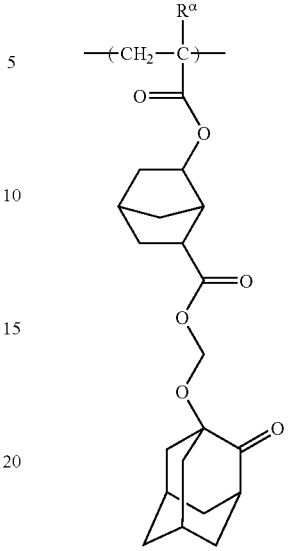
(a1-4-8) 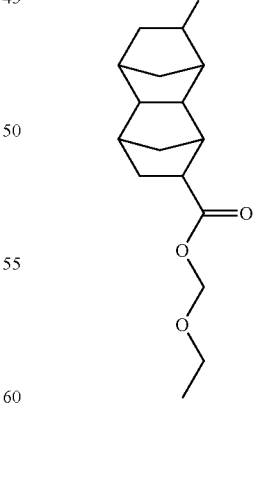

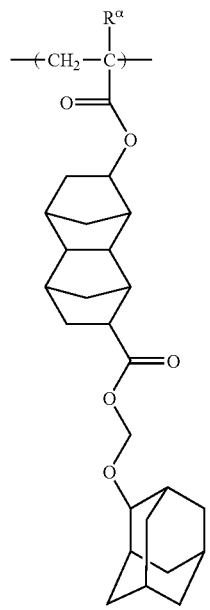 (a1-4-9)
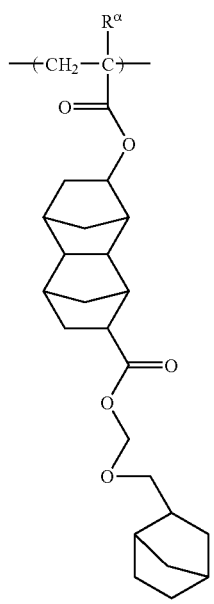 (a1-4-11)
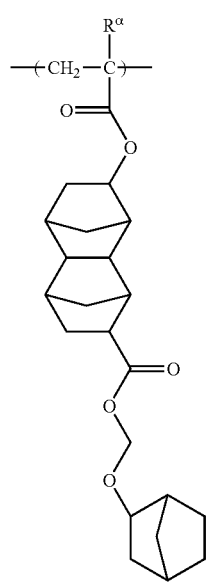 (a1-4-10)
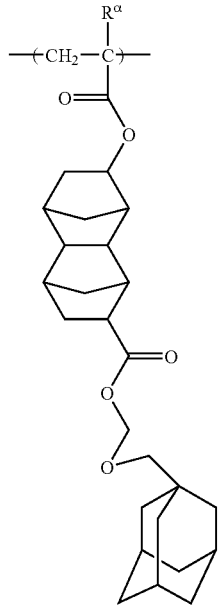 (a1-4-12)

(a1-4-13)
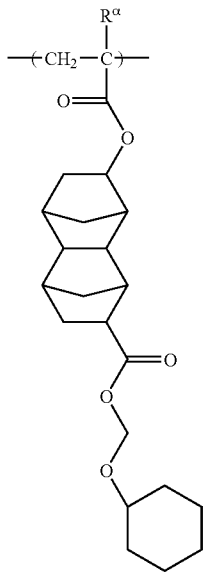

(a1-4-14)
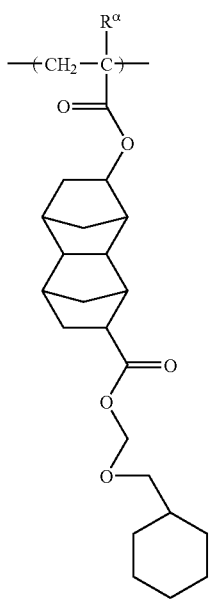

(a1-4-15)
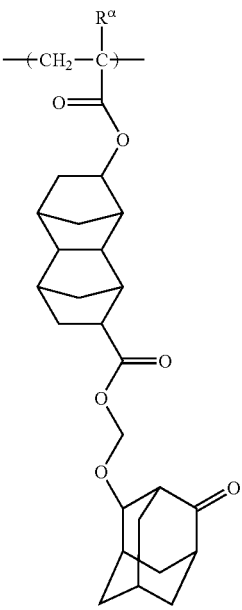

As the structural unit (a1), one type of structural unit may be used alone, or two or more types of structural units may be used in combination.

Among these, structural units represented by general formula (a1-1) to (a1-3) are preferable, and more specifically, the use of at least one structural unit selected from the group consisting of structural units represented by formulas (a1-1-1) to (a1-1-14), (a1-1-20) to (a1-1-23) and (a1-3-25) to (a1-3-28) is more preferable.

Moreover, as the structural unit (a1), structural units represented by general formula (a1-1-01) shown below, which includes the structural units represented by formulas (a1-1-1) to (a1-1-3), structural units represented by general formula (a1-1-02) shown below, which includes the structural units represented by formulas (a1-1-16) and (a1-1-17) and formulas (a1-1-20) to (a1-1-23), structural units represented by general formula (a1-3-01) shown below, which includes the structural units represented by formulas (a1-3-25) and (a1-3-26), and structural units represented by general formula (a1-3-02) shown below, which includes the structural units represented by formulas (a1-3-27) and (a1-3-28) are preferred.

[Chemical Formula 37]

(a1-1-01)
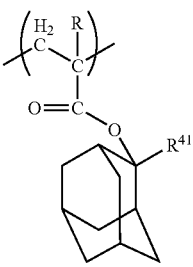

In the formula, R represents a hydrogen atom, a lower alkyl group or a halogenated lower alkyl group, and $R^{41}$ represents a lower alkyl group.

[Chemical Formula 38]

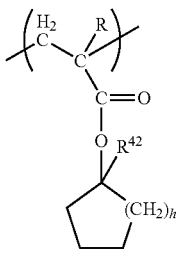

(a1-1-02)

In the formula, R represents a hydrogen atom, a lower alkyl group or a halogenated lower alkyl group, $R^{42}$ represents a lower alkyl group, and h represents an integer of 1 to 6.

In general formula (a1-1-01), R is the same as defined above. The lower alkyl group for $R^{41}$ is the same as defined above for the lower alkyl group for R, and is preferably a methyl group or ethyl group.

In general formula (a1-1-02), R is the same as defined above. The lower alkyl group for $R^{42}$ is the same as defined above for the lower alkyl group for R, is preferably a methyl group or ethyl group, and is most preferably an ethyl group. h is preferably 1 or 2, and is most preferably 2.

[Chemical Formula 39]

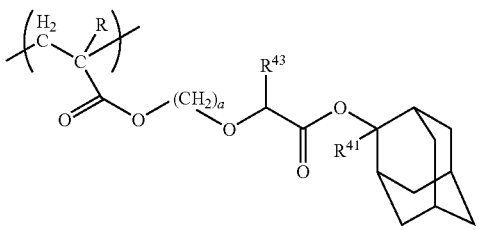

(a1-3-01)

In the formula, R represents a hydrogen atom, a lower alkyl group or a halogenated lower alkyl group, $R^{41}$ is the same as defined above, $R^{43}$ represents a hydrogen atom or a methyl group, and a represents an integer of 1 to 10.

[Chemical Formula 40]

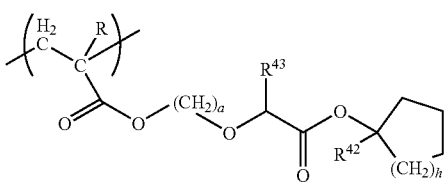

(a1-3-02)

In the formula, R represents a hydrogen atom, a lower alkyl group or a halogenated lower alkyl group, $R^{42}$ and h are the same as defined above, $R^{43}$ represents a hydrogen atom or a methyl group, and a represents an integer of 1 to 10.

In general formulas (a1-3-01) and (a1-3-02), R is the same as defined above.

Each of $R^{41}$ and $R^{42}$ represents a lower alkyl group, which is the same as defined above for the lower alkyl group for R, and is preferably a methyl group or an ethyl group.

$R^{43}$ represents a hydrogen atom or a methyl group, and is preferably a hydrogen atom.

a represents an integer of 1 to 8, is more preferably an integer of 2 to 5, and is most preferably 2.

h represents an integer of 1 to 6, is preferably 1 or 2, and is most preferably 2.

In the component (A1), the amount of the structural unit (a1), based on the combined total of all the structural units that constitute the component (A1), is preferably within a range from 10 to 80 mol %, more preferably from 20 to 70 mol %, and still more preferably from 25 to 50 mol %. By ensuring that the amount of the structural unit (a1) is at least as large as the lower limit of the above range, a pattern can be formed easily using a resist composition prepared from the component (A1), whereas by ensuring that the amount is not more than the upper limit of the above range, a good balance can be achieved with the other structural units.

The monomers that yield the structural unit represented by general formula (a1-3-01) and the structural unit represented by general formula (a1-3-02) (hereafter these monomers are referred to jointly as "the monomer W") can be produced, for example, using the production method described below.

Method of producing monomer W:

A compound represented by general formula (X-2) shown below is added, in the presence of a base, to a solution obtained by dissolving a compound represented by general formula (X-1) shown below in a reaction solvent, and a reaction is then performed to obtain a compound represented by general formula (X-3) shown below (hereafter referred to as "compound (X-3)"). Subsequently, a compound represented by general formula (X-4) shown below is added, in the presence of a base, to the solution containing the compound (X-3) dissolved therein, and the resulting reaction yields the monomer W.

Examples of the base include inorganic bases such as sodium hydride, $K_2CO_3$ and $Cs_2CO_3$, and organic bases such as triethylamine, 4-dimethylaminopyridine (DMAP) and pyridine.

There are no particular limitations on the reaction solvent, provided it is able to dissolve the compound (X-1) and the compound (X-2) that are used as raw materials. Specific examples of the reaction solvent include tetrahydrofuran (THF), acetone, dimethylformamide (DMF), dimethylacetamide, dimethylsulfoxide (DMSO) and acetonitrile.

[Chemical Formula 41]

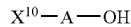

(X-1)

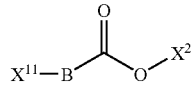

(X-2)

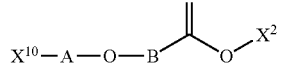

(X-3)

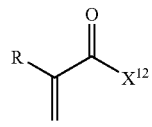

(X-4)

In the formulas, R represents a hydrogen atom, a lower alkyl group or a halogenated lower alkyl group, each of A and B independently represents a divalent hydrocarbon group which may have a substituent, $X^2$ represents an acid-dissociable, dissolution-inhibiting group, each of $X^{10}$ and $X^{12}$ independently represents a hydroxyl group or a halogen atom, provided that one of $X^{10}$ and $X^{12}$ is a hydroxyl group and the other is a halogen atom, and $X^{11}$ represents a halogen atom.

In the above formulas, R, $X^2$, A and B are the same as defined above.

Examples of the halogen atom for $X^{10}$, $X^{11}$ and $X^{12}$ include a bromine atom, chlorine atom, iodine atom, or fluorine atom.

From the perspective of achieving superior reactivity, the halogen atoms for $X^{10}$ and $X^{12}$ are each preferably a chlorine atom or a bromine atom.

In terms of achieving superior reactivity, $X^{11}$ is preferably a bromine atom or a chlorine atom, and is most preferably a bromine atom.

Structural Unit (a2)

The structural unit (a2) is a structural unit derived from an acrylate ester containing a lactone-containing cyclic group.

The term "lactone-containing cyclic group" refers to a cyclic group including one ring containing a —O—C(O)— structure (the lactone ring). This "lactone ring" is counted as the first ring, so that a lactone-containing cyclic group in which the only ring structure is the lactone ring is referred to as a monocyclic group, and groups that also contain other ring structures are described as polycyclic groups regardless of the structure of the other rings.

When the component (A1) is used for forming a resist film, the lactone-containing cyclic group of the structural unit (a2) is effective in improving the adhesion between the resist film and the substrate, and increasing the compatibility with the developing solution containing water.

There are no particular limitations on the structural unit (a2), and an arbitrary structural unit may be used.

Specific examples of lactone-containing monocyclic groups include groups in which one hydrogen atom has been removed from a 4- to 6-membered lactone ring, including a group in which one hydrogen atom has been removed from β-propiolactone, a group in which one hydrogen atom has been removed from γ-butyrolactone, and a group in which one hydrogen atom has been removed from δ-valerolactone. Further, specific examples of lactone-containing polycyclic groups include groups in which one hydrogen atom has been removed from a lactone ring-containing bicycloalkane, tricycloalkane or tetracycloalkane.

More specifically, examples of the structural unit (a2) include structural units represented by general formulas (a2-1) to (a2-5) shown below.

[Chemical Formula 42]

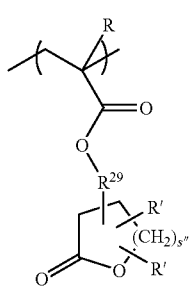

(a2-1)

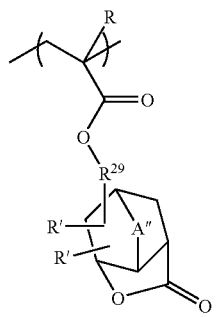

(a2-2)

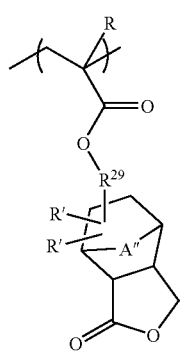

(a2-3)

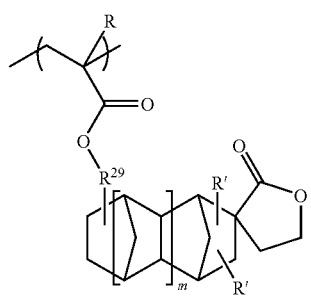

(a2-4)

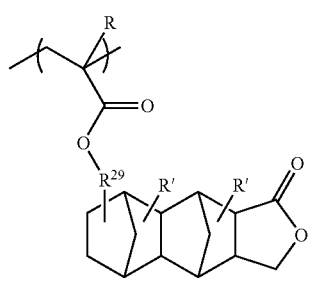

(a2-5)

In the formulas, R represents a hydrogen atom, a lower alkyl group or a halogenated lower alkyl group, each R' independently represents a hydrogen atom, an alkyl group of 1 to 5 carbon atoms, an alkoxy group of 1 to 5 carbon atoms or —COOR", wherein R" represents a hydrogen atom or an alkyl group, $R^{29}$ represents a single bond or a divalent linking group, s" represents 0 or an integer of 1 or 2, A" represents an oxygen atom, a sulfur atom or an alkylene group of 1 to 5 carbon atoms which may contain an oxygen atom or a sulfur atom, and m represents an integer of 0 or 1.

In general formulas (a2-1) to (a2-5), R is the same as defined above for R in the structural unit (a1).

Examples of the alkyl group of 1 to 5 carbon atoms for R' include a methyl group, ethyl group, propyl group, n-butyl group or tert-butyl group.

Examples of the alkoxy group of 1 to 5 carbon atoms for R' include a methoxy group, ethoxy group, n-propoxy group, iso-propoxy group, n-butoxy group or tert-butoxy group.

In terms of industrial availability, R' is preferably a hydrogen atom.

When R" represents a linear or branched alkyl group, it is preferably an alkyl group of 1 to 10 carbon atoms, and more preferably an alkyl group of 1 to 5 carbon atoms.

When R" represents a cyclic alkyl group, it preferably contains 3 to 15 carbon atoms, more preferably 4 to 12 carbon atoms, and most preferably 5 to 10 carbon atoms. Examples of the cyclic alkyl group include groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane.

A" is preferably an alkylene group of 1 to 5 carbon atoms or —O—, is more preferably an alkylene group of 1 to 5 carbon atoms, and is most preferably a methylene group.

$R^{29}$ represents a single bond or a divalent linking group. Examples of the divalent linking group include the same divalent linking groups as those described above for $Y^2$ in general formula (a1-0-2), and of these groups, an alkylene group, an ester linkage (—C(=O)—O—) or a combination thereof is preferred. The alkylene group for the divalent linking group for $R^{29}$ is preferably a linear or branched alkylene group. Specific examples include the same linear alkylene groups and branched alkylene groups as those listed above for the aliphatic hydrocarbon group for A within the description for $Y^2$.

s" is preferably an integer of 1 or 2.

Specific examples of structural units represented by general formulas (a2-1) to (a2-5) are shown below. In each of the formulas shown below, $R^\alpha$ represents a hydrogen atom, a methyl group or a trifluoromethyl group.

[Chemical Formula 43]

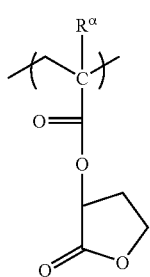

(a2-1-1)

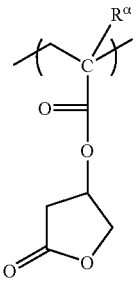

(a2-1-2)

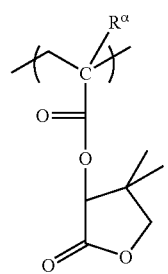

(a2-1-3)

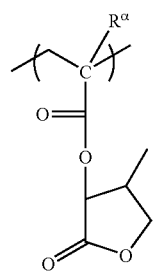

(a2-1-4)

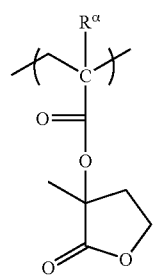

(a2-1-5)

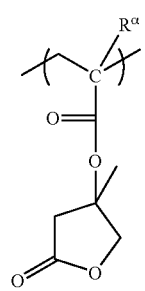

(a2-1-6)

(a2-1-7) 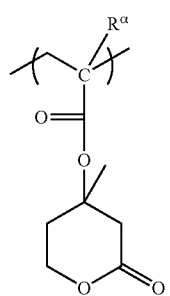
(a2-1-8) 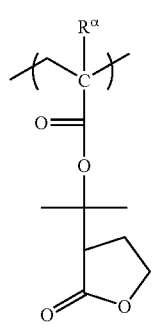
(a2-1-9) 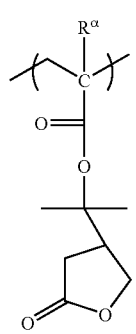
(a2-1-10) 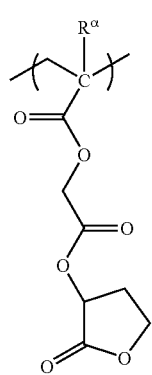
(a2-1-11) 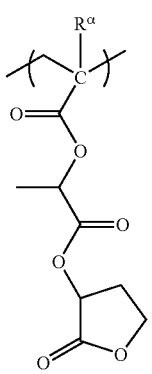
(a2-1-12) 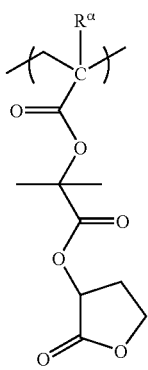
(a2-1-13) 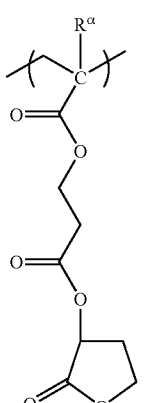
[Chemical Formula 44]
(a2-2-1) 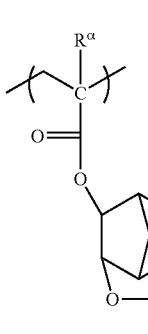

(a2-2-2) (a2-2-3) (a2-2-4) (a2-2-5) (a2-2-6) (a2-2-7) (a2-2-8) (a2-2-9) (a2-2-10) (a2-2-11)

(a2-2-12)
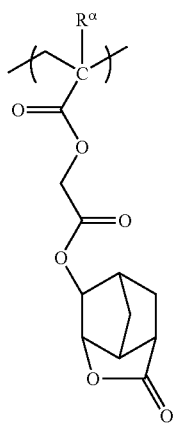
(a2-2-13)
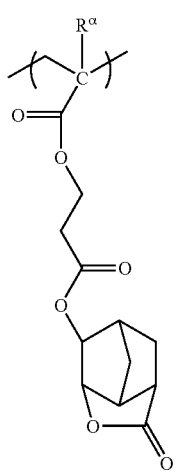
(a2-2-14)
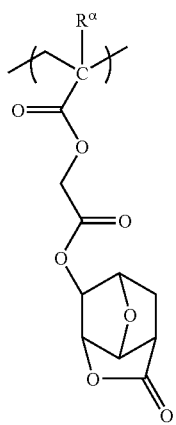
(a2-2-15)
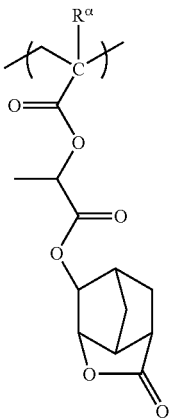
(a2-2-16)
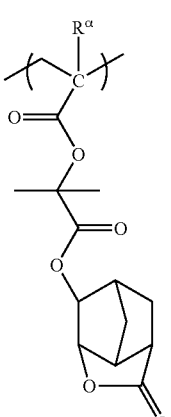
(a2-2-17)
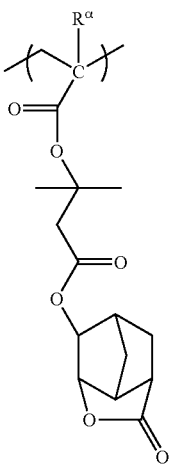

[Chemical Formula 45]
(a2-3-1) 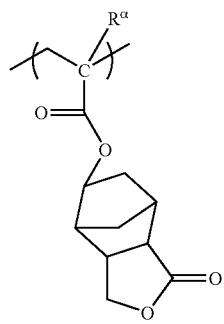
(a2-3-2) 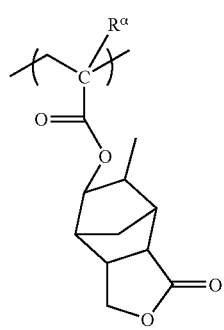
(a2-3-3) 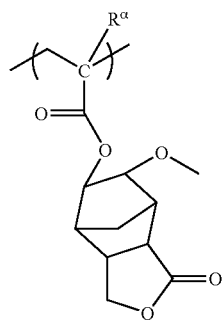
(a2-3-4) 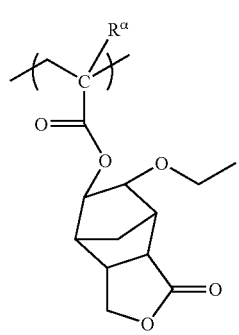
(a2-3-5) 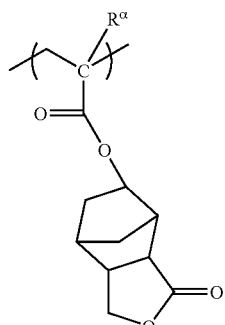
[Chemical Formula 46]
(a2-4-1) 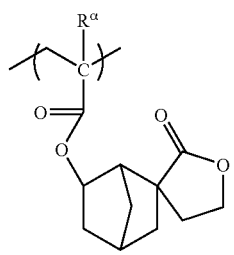
(a2-4-2) 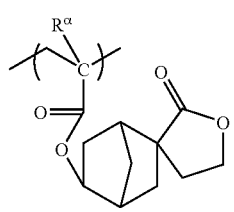
(a2-4-3) 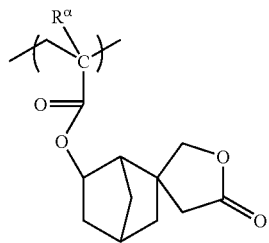
(a2-4-4) 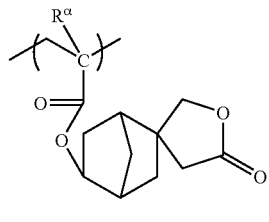
(a2-4-5)

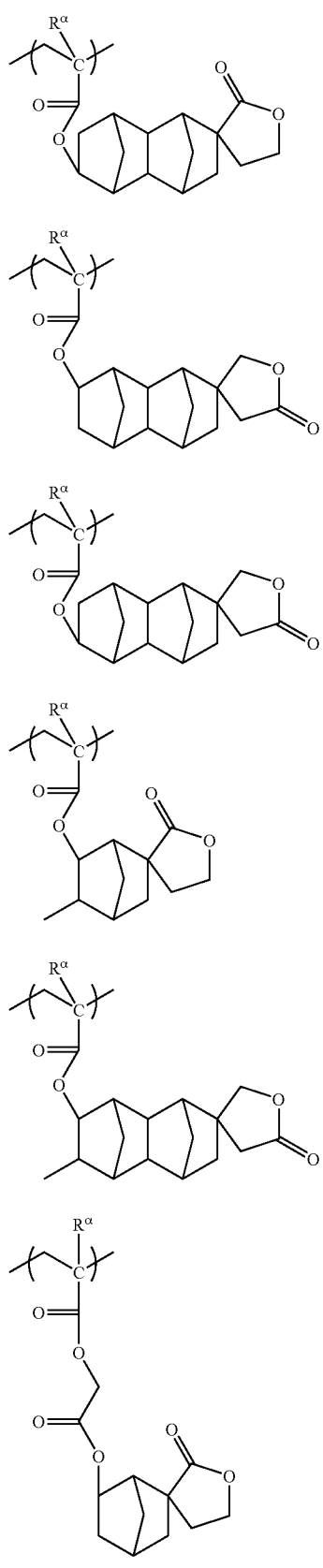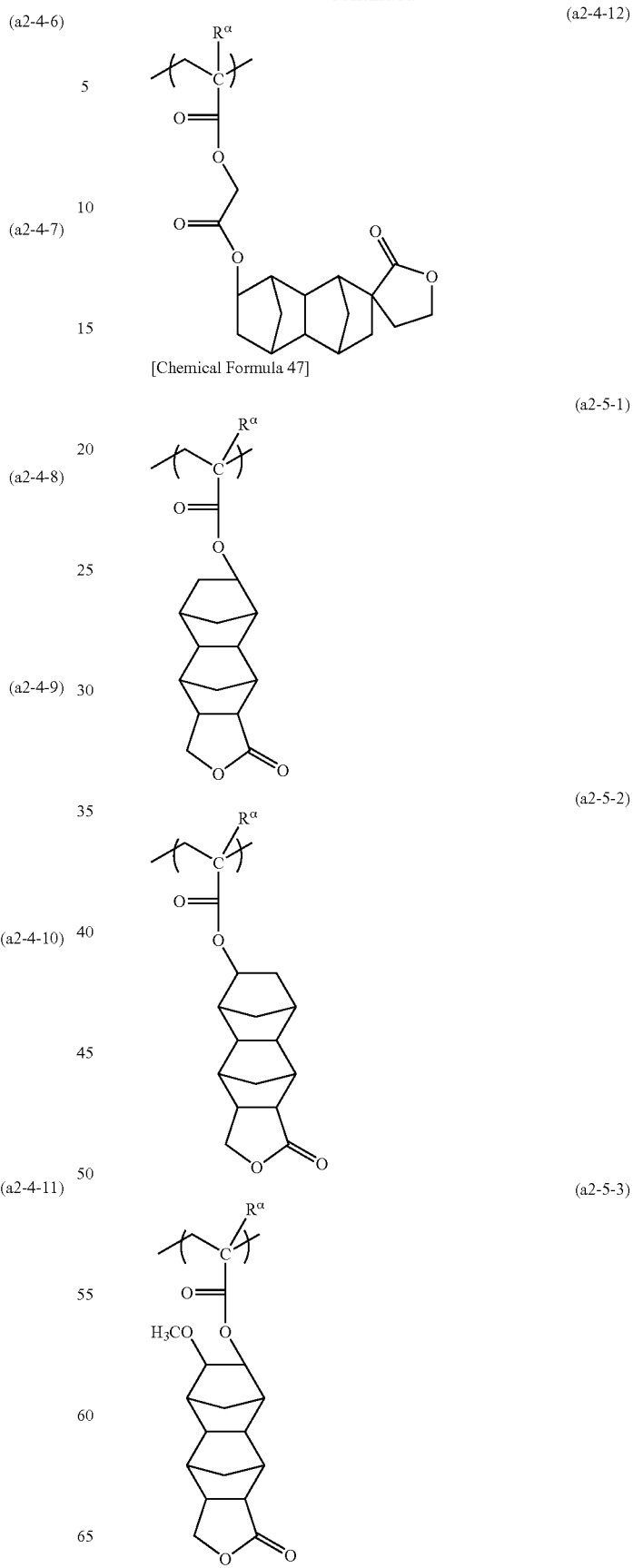

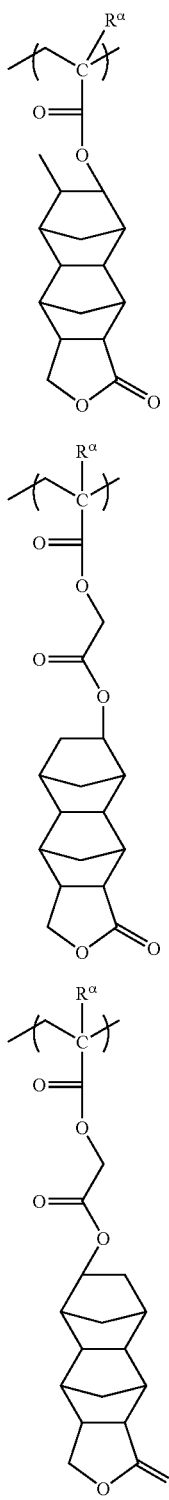

(a2-5-4)

(a2-5-5)

(a2-5-6)

In the component (A1), as the structural unit (a2), one type of structural unit may be used alone, or two or more types of structural units may be used in combination.

The structural unit (a2) is preferably at least one structural unit selected from the group consisting of structural units represented by general formulas (a2-1) to (a2-5), and is more preferably at least one structural unit selected from the group consisting of structural units represented by general formulas (a2-1) to (a2-3). Of these, it is particularly preferable to use at least one structural unit selected from the group consisting of structural units represented by chemical formulas (a2-1-1), (a2-2-1), (a2-2-7), (a2-3-1) and (a2-3-5).

The amount of the structural unit (a2) within the component (A1), based on the combined total of all the structural units that constitute the component (A1), is preferably within a range from 5 to 60 mol %, more preferably from 10 to 50 mol %, and most preferably from 20 to 50 mol %. By ensuring that this amount is at least as large as the lower limit of the above range, the effects achieved by including the structural unit (a2) are able to manifest satisfactorily. On the other hand, by ensuring that the amount is not more than the upper limit of the above range, a good balance can be achieved with the other structural units.

Structural Unit (a3)

The structural unit (a3) is a structural unit derived from an acrylate ester containing a polar group-containing aliphatic hydrocarbon group.

By including the structural unit (a3) within the component (A1), the hydrophilicity of the component (A) is improved, and hence, the compatibility of the component (A) with the developing solution is improved. As a result, the alkali solubility of the exposed portions improves, which contributes to favorable improvements in the resolution.

Examples of the polar group include a hydroxyl group, cyano group, carboxyl group, or hydroxyalkyl group in which some of the hydrogen atoms of the alkyl group have been substituted with fluorine atoms, although a hydroxyl group is particularly desirable.

Examples of the aliphatic hydrocarbon group include linear or branched hydrocarbon groups (and preferably alkylene groups) of 1 to 10 carbon atoms, and cyclic aliphatic hydrocarbon groups (cyclic groups). These cyclic groups may be either monocyclic or polycyclic, and can be selected appropriately from the multitude of groups that have been proposed for the resins of resist compositions designed for use with ArF excimer lasers. The cyclic group is preferably a polycyclic group, and preferably contains 7 to 30 carbon atoms. In the case of a monocyclic group, the group preferably contains 3 to 6 carbon atoms.

Of the various possibilities, structural units derived from an acrylate ester that includes an aliphatic polycyclic group containing a hydroxyl group, cyano group, carboxyl group or a hydroxyalkyl group in which some of the hydrogen atoms of the alkyl group have been substituted with fluorine atoms are particularly desirable. Examples of the polycyclic group include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, groups in which two or more hydrogen atoms have been removed from norbornane, or groups in which two or more hydrogen atoms have been removed from tetracyclododecane are preferred industrially.

When the hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2) and (a3-3) shown below are preferable.

[Chemical Formula 48]

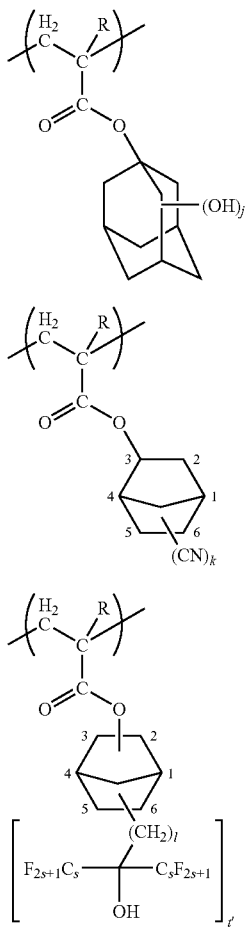

(a3-1)

(a3-2)

(a3-3)

In the formulas, R is the same as defined above, j is an integer of 1 to 3, k is an integer of 1 to 3, t' is an integer of 1 to 3, l is an integer of 1 to 5, and s is an integer of 1 to 3.

In formula (a3-1), j is preferably 1 or 2, and more preferably 1. When j is 2, it is preferable that the hydroxyl groups are bonded to the 3rd and 5th positions of the adamantyl group. When j is 1, it is preferable that the hydroxyl group is bonded to the 3rd position of the adamantyl group.

j is preferably 1, and it is particularly desirable that the hydroxyl group is bonded to the 3rd position of the adamantyl group.

In formula (a3-2), k is preferably 1. The cyano group is preferably bonded to the 5th or 6th position of the norbornyl group.

In formula (a3-3), t' is preferably 1. l is preferably 1. s is preferably 1. Further, in formula (a3-3), it is preferable that a 2-norbornyl group or 3-norbornyl group is bonded to the terminal of the carboxyl group of the acrylic acid. The fluorinated alkyl alcohol is preferably bonded to the 5th or 6th position of the norbornyl group.

In the component (A1), as the structural unit (a3), one type of structural unit may be used alone, or two or more types may be used in combination.

The amount of the structural unit (a3) within the component (A1), based on the combined total of all the structural units that constitute the component (A1), is preferably within a range from 5 to 50 mol %, more preferably from 5 to 40 mol %, and still more preferably from 5 to 25 mol %. By ensuring that this amount is at least as large as the lower limit of the above range, the effects achieved by including the structural unit (a3) are able to manifest satisfactorily. On the other hand, by ensuring that the amount is not more than the upper limit of the above range, a good balance can be achieved with the other structural units.

Structural Unit (a4)

The structural unit (a4) is a structural unit derived from an acrylate ester containing a non-acid-dissociable aliphatic polycyclic group.

Examples of the polycyclic group within the structural unit (a4) include the same groups as those described above in connection with the aforementioned structural unit (a1), and any of the multitude of conventional polycyclic groups used within the resin component of resist compositions for ArF excimer lasers or KrF excimer lasers (and particularly for ArF excimer lasers) can be used.

In terms of factors such as industrial availability and the like, at least one polycyclic group selected from amongst a tricyclodecyl group, adamantyl group, tetracyclododecyl group, isobornyl group and norbornyl group is particularly desirable. These polycyclic groups may be substituted with a linear or branched alkyl group of 1 to 5 carbon atoms.

Specific examples of the structural unit (a4) include units with structures represented by general formulas (a-4-1) to (a-4-5) shown below.

[Chemical Formula 49]

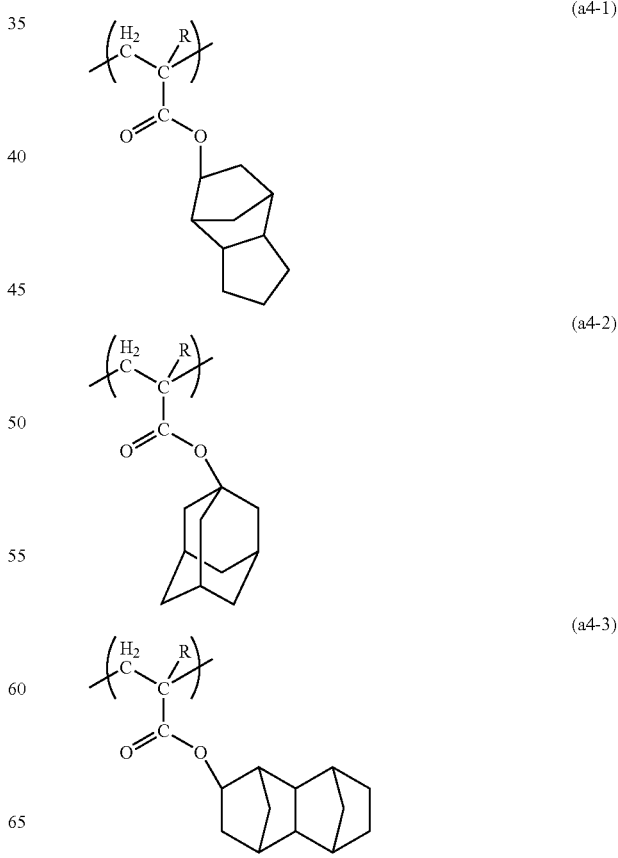

(a4-1)

(a4-2)

(a4-3)

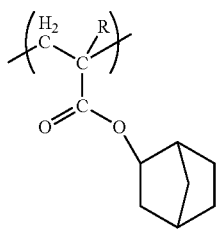
(a4-4)

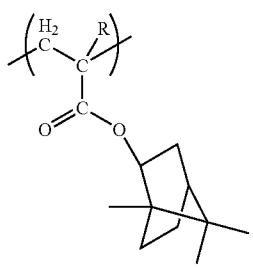
(a4-5)

In the formulas, R is the same as defined above.

When the structural unit (a4) is included in the component (A1), the amount of the structural unit (a4), based on the combined total of all the structural units that constitute the component (A1), is preferably within the range from 1 to 30 mol %, and more preferably from 10 to 20 mol %.

Structural Unit (a6)

The structural unit (a6) is a structural unit derived from a styrene.

Although the structural unit (a6) is not essential in the present invention, including the structural unit (a6) enables the solubility in alkali developing solutions to be altered. Further, the structural unit (a6) also yields improved dry etching resistance, which is desirable.

In the present description, the term "styrene" includes both styrene and compounds in which the α-position hydrogen atom of styrene has been substituted with another substituent such as an alkyl group.

A "structural unit derived from a styrene" describes a structural unit formed by cleavage of the ethylenic double bond of the styrene. One or more hydrogen atoms bonded to the phenyl group of the styrene may be substituted with substituents such as an alkyl group of 1 to 5 carbon atoms.

Examples of preferred structures for the structural unit (a6) include the structural units represented by general formula (a6-1) shown below.

[Chemical Formula 50]

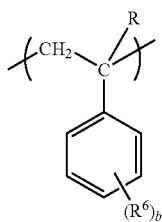
(a6-1)

In formula (a6-1), R is the same as defined above, $R^6$ represents a halogen atom, a lower alkyl group of 1 to 5 carbon atoms or a halogenated alkyl group of 1 to 5 carbon atoms, and b represents an integer of 0 to 3.

In general formula (a6-1), R is the same as defined above for R in general formula (a5-1).

Examples of $R^6$ include the same groups as those listed above for $R^{12}$ in formula (a5-1).

b represents an integer of 0 to 3, is preferably 0 or 1, and from an industrial viewpoint, is most preferably 0.

When b is 1, the substitution position for $R^6$ may be any of the o-position, m-position or p-position on the phenyl group.

When b is 2 or 3, any combination of substitution positions may be used. The plurality of $R^6$ groups may be either the same or different.

As the structural unit (a6), one type of structural unit may be used alone, or two or more types may be used in combination.

When the structural unit (a6) is included in the component (A1), the amount of the structural unit (a6) within the component (A1), based on the combined total of all the structural units that constitute the component (A1), is preferably within the range from 1 to 20 mol %, more preferably from 3 to 15 mol %, and still more preferably from 5 to 15 mol %. By ensuring that this amount is at least as large as the lower limit of the above range, the effects achieved by including the structural unit (a6) manifest more readily. On the other hand, by ensuring that the amount is not more than the upper limit of the above range, a good balance can be achieved with the other structural units.

Structural Unit (a7)

The structural unit (a7) is a structural unit derived from a hydroxystyrene in which at least a portion of the hydroxyl group hydrogen atoms have been protected with substituents.

In the structural unit (a7), examples of the substituent include tertiary alkyl group-containing groups, alkoxyalkyl groups, acid-dissociable, dissolution-inhibiting groups, and organic groups that contain an acid-dissociable, dissolution-inhibiting group. These acid-dissociable, dissolution-inhibiting groups exclude groups that have a 1,3-dioxole skeleton.

Tertiary Alkyl Group-Containing Group

In the present description, the term "tertiary alkyl group" describes an alkyl group containing a tertiary carbon atom. As mentioned above, the term "alkyl group" describes monovalent saturated hydrocarbon groups, and includes chain-like (linear or branched) alkyl groups as well as alkyl groups having a cyclic structure.

The "tertiary alkyl group-containing group" describes a group containing a tertiary alkyl group within its structure. The tertiary alkyl group-containing group may be composed solely of the tertiary alkyl group, or may be composed of the tertiary alkyl group and other atom(s) or group(s) besides the tertiary alkyl group.

Examples of these "other atom(s) or group(s) besides the tertiary alkyl group" that may constitute the tertiary alkyl group-containing group together with the tertiary alkyl group include a carbonyloxy group, carbonyl group, alkylene group or oxygen atom.

In the structural unit (a7), examples of the tertiary alkyl group-containing group include tertiary alkyl group-containing groups which do not contain a cyclic structure, and tertiary alkyl group-containing groups which contain a cyclic structure.

A tertiary alkyl group-containing group which does not contain a cyclic structure contains a branched-chain tertiary alkyl group as the tertiary alkyl group, and includes no cyclic structure within the group structure.

Examples of branched-chain tertiary alkyl groups include the groups represented by general formula (I) shown below.

[Chemical Formula 51]

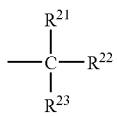
(I)

In formula (I), each of $R^{21}$ to $R^{23}$ independently represents a linear or branched alkyl group. These alkyl groups preferably contain 1 to 5 carbon atoms, and more preferably 1 to 3 carbon atoms.

Further, the total number of carbon atoms within the group represented by general formula (I) is preferably from 4 to 7 carbon atoms, more preferably from 4 to 6 carbon atoms, and most preferably 4 or 5 carbon atoms.

Specific examples of the group represented by general formula (I) include a tert-butyl group and tert-pentyl group, and a tert-butyl group is particularly desirable.

Examples of the tertiary alkyl group-containing groups which do not contain a cyclic structure include the branched-chain tertiary alkyl groups described above (these are acid-dissociable, dissolution-inhibiting groups), tertiary alkyl group-containing chain-like alkyl groups in which an aforementioned branched-chain tertiary alkyl group is bonded to a linear or branched alkylene group, tertiary alkyloxycarbonyl groups containing an aforementioned branched-chain tertiary alkyl group as the tertiary alkyl group, and tertiary alkyloxycarbonylalkyl groups containing an aforementioned branched-chain tertiary alkyl group as the tertiary alkyl group.

The alkylene group in the tertiary alkyl group-containing chain-like alkyl group is preferably an alkylene group of 1 to 5 carbon atoms, more preferably an alkylene group of 1 to 4 carbon atoms, and still more preferably an alkylene group of 1 or 2 carbon atoms.

Examples of the chain-like tertiary alkyloxycarbonyl groups include groups represented by general formula (II) shown below. In formula (II), $R^{21}$ to $R^{23}$ are the same as defined above for $R^{21}$ to $R^{23}$ in formula (I). As this chain-like tertiary alkyloxycarbonyl group, a tert-butyloxycarbonyl group (t-boc) or tert-pentyloxycarbonyl group is preferred.

[Chemical Formula 52]

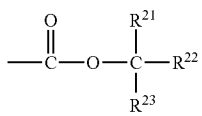
(II)

Examples of the chain-like tertiary alkyloxycarbonylalkyl groups include groups represented by general formula (III) shown below. In formula (III), $R^{21}$ to $R^{23}$ are the same as defined above for $R^{21}$ to $R^{23}$ in formula (I). f represents an integer of 1 to 3, and is preferably 1 or 2. As this chain-like tertiary alkyloxycarbonylalkyl group, a tert-butyloxycarbonylmethyl group or tert-butyloxycarbonylethyl group is preferred.

Of the above groups, the tertiary alkyl group-containing group which does not contain a cyclic structure is preferably a tertiary alkyloxycarbonyl group or a tertiary alkyloxycarbonylalkyl group, is more preferably a tertiary alkyloxycarbonyl group, and is most preferably a tert-butyloxycarbonyl group (t-boc).

[Chemical Formula 53]

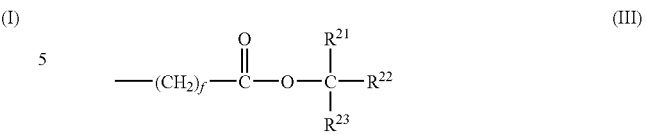
(III)

A tertiary alkyl group-containing group which contains a cyclic structure describes a group that includes a tertiary carbon atom and a cyclic structure within the group structure.

In the tertiary alkyl group-containing group which contains a cyclic structure, the cyclic structure preferably contains 4 to 12 carbon atoms, more preferably 5 to 10 carbon atoms, and most preferably 6 to 10 carbon atoms within the ring. Examples of the cyclic structure include groups in which one or more hydrogen atoms have been removed from a monocycloalkane or a polycycloalkane such as a bicycloalkane, tricycloalkane or tetracycloalkane. Preferable examples include groups in which one or more hydrogen atoms have been removed from a monocycloalkane such as cyclopentane or cyclohexane, or a polycycloalkane such as adamantane, norbornane, isobornane, tricyclodecane or tetracyclododecane Examples of the tertiary alkyl group-containing group which contains a cyclic structure include groups having the following group [1] or [2] as the tertiary alkyl group.

(1) A group in which a linear or branched alkyl group is bonded to a carbon atom which constitutes part of the ring of a cyclic alkyl group (cycloalkyl group), so that the carbon atom becomes a tertiary carbon atom (this group functions as an acid-dissociable, dissolution-inhibiting group)

(2) A group in which an alkylene group (branched alkylene group) having a tertiary carbon atom is bonded to a carbon atom which constitutes part of the ring of a cycloalkyl group.

In the above group (1), the linear or branched alkyl group preferably has 1 to 5 carbon atoms, more preferably 1 to 4 carbon atoms, and most preferably 1 to 3 carbon atoms.

Examples of the group (1) include a 2-methyl-2-adamantyl group, 2-ethyl-2-adamantyl group, 1-methyl-1-cycloalkyl group or 1-ethyl-1-cycloalkyl group.

In the above group (2), the cycloalkyl group having a branched alkylene group bonded thereto may have a substituent. Examples of the substituent include a fluorine atom, a fluorinated lower alkyl group of 1 to 5 carbon atoms, and an oxygen atom (=O).

Examples of the group (2) include groups represented by chemical formula (IV) shown below (these are acid-dissociable, dissolution-inhibiting groups).

[Chemical Formula 54]

(IV)

In formula (IV), $R^{24}$ represents a cycloalkyl group which may or may not have a substituent. Examples of the substituent which the cycloalkyl group may have include a fluorine atom, a fluorinated lower alkyl group of 1 to 5 carbon atoms, and an oxygen atom (=O).

Each of $R^{25}$ and $R^{26}$ independently represents a linear or branched alkyl group.

Examples of the alkyl group include the same alkyl groups as those listed above for $R^{21}$ to $R^{23}$ in formula (I).

Alkoxyalkyl Group

In the structural unit (a7), examples of the alkoxyalkyl group include groups represented by general formula (V) shown below.

[Chemical Formula 55]

$$—R^{52}—O—R^{51} \quad (V)$$

In formula (V), $R^{51}$ represents a linear, branched or cyclic alkyl group.

When $R^{51}$ represents a linear or branched alkyl group, it is preferably an alkyl group of 1 to 5 carbon atoms, more preferably an ethyl group or methyl group, and is most preferably an ethyl group.

When $R^{51}$ represents a cyclic alkyl group, it preferably has 4 to 15 carbon atoms, more preferably 4 to 12 carbon atoms, and most preferably 5 to 10 carbon atoms. Examples of the cyclic alkyl group include groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group. Specific examples include groups in which one or more hydrogen atoms have been removed from a monocycloalkane such as cyclopentane and cyclohexane, or a polycycloalkane such as adamantane, norbornane, isobornane, tricyclodecane or tetracyclododecane. Of these, groups in which one or more hydrogen atoms have been removed from adamantane are preferable.

$R^{52}$ represents a linear or branched alkylene group. The alkylene group preferably has 1 to 5 carbon atoms, more preferably 1 to 3 carbon atoms, and most preferably 1 or 2 carbon atoms.

Of the above possibilities, the alkoxyalkyl group is preferably a group represented by general formula (VI) shown below (which is an acid-dissociable, dissolution-inhibiting group).

[Chemical Formula 56]

In formula (VI), $R^{51}$ is the same as defined above, and each of $R^{53}$ and $R^{54}$ independently represents a linear or branched alkyl group, or a hydrogen atom.

For $R^{53}$ and $R^{54}$, the alkyl group preferably has 1 to 15 carbon atoms, and may be either linear or branched. The alkyl group for $R^{53}$ and $R^{54}$ is preferably an ethyl group or methyl group, and is most preferably a methyl group.

It is particularly desirable one of $R^{53}$ and $R^{54}$ is a hydrogen atom, and the other is a methyl group.

Acid-Dissociable, Dissolution-Inhibiting Group

In the structural unit (a7), there are no particular restrictions on the above acid-dissociable, dissolution-inhibiting group, provided it does not include a 1,3-dioxole skeleton, and any of the multitude of acid-dissociable, dissolution-inhibiting groups proposed for use within resins for resist compositions designed for use with a KrF excimer laser or ArF excimer laser can be used. Specific examples include the acid-dissociable, dissolution-inhibiting group (VII) described below.

Examples of the acid-dissociable, dissolution-inhibiting group (VII) include groups represented by general formula (VII-b) shown below.

[Chemical Formula 57]

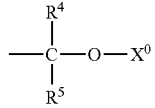

$$(VII\text{-}b)$$

In formula (VII-b), $X^0$ represents an aliphatic cyclic group, an aromatic cyclic hydrocarbon group or a lower alkyl group of 1 to 5 carbon atoms, $R^4$ represents a hydrogen atom or a lower alkyl group of 1 to 5 carbon atoms, or alternatively, each of $X^0$ and $R^4$ may independently represent an alkylene group of 1 to 5 carbon atoms, wherein $X^0$ and $R^4$ are bonded together, and $R^5$ represents a hydrogen atom or a lower alkyl group of 1 to 5 carbon atoms.

In general formula (VII-b), $X^0$ represents an aliphatic cyclic group, an aromatic cyclic hydrocarbon group or a lower alkyl group of 1 to 5 carbon atoms.

The aliphatic cyclic group for $X^0$ is a monovalent aliphatic cyclic group. The aliphatic cyclic group can use any of the multitude of aliphatic cyclic groups proposed for use within conventional ArF resists. Examples include aliphatic monocyclic groups of 5 to 7 carbon atoms and aliphatic polycyclic groups of 7 to 16 carbon atoms.

Examples of the aliphatic monocyclic groups of 5 to 7 carbon atoms include groups in which one hydrogen atom has been removed from a monocycloalkane, and specific examples include groups in which one hydrogen atom has been removed from cyclopentane or cyclohexane.

Examples of the aliphatic polycyclic groups of 7 to 16 carbon atoms include groups in which one hydrogen atom has been removed from a bicycloalkane, tricycloalkane or tetracycloalkane or the like. Specific examples include groups in which one hydrogen atom has been removed from a polycycloalkane such as adamantane, norbornane, isobornane, tricyclodecane or tetracyclododecane. Of these, an adamantyl group, norbornyl group or tetracyclododecyl group is preferred industrially, and an adamantyl group is particularly desirable.

Examples of the aromatic cyclic hydrocarbon group for $X^0$ include aromatic polycyclic groups of 10 to 16 carbon atoms. Specific examples include groups in which one hydrogen atom has been removed from naphthalene, anthracene, phenanthrene or pyrene or the like. Specific examples include a 1-naphthyl group, 2-naphthyl group, 1-anthryl group, 2-anthryl group, 1-phenanthryl group, 2-phenanthryl group, 3-phenanthryl group or 1-pyrenyl group, and of these, a 2-naphthyl group is particularly desirable.

Examples of the lower alkyl group for $X^0$ include the same groups as those listed above for the lower alkyl group which may be bonded to the α-position of the aforementioned hydroxystyrene, although a methyl group or ethyl group is preferred, and an ethyl group is the most desirable.

In formula (VII-b), examples of the lower alkyl group for $R^4$ includes the same groups as those described for the lower alkyl group for $X^0$. From an industrial perspective, a methyl group or ethyl group is preferred, and a methyl group is particularly desirable.

$R^5$ represents a lower alkyl group or a hydrogen atom. Examples of the lower alkyl group for $R^5$ include the same groups as those described above for the lower alkyl group for $R^4$. From an industrial perspective, $R^5$ is most preferably a hydrogen atom.

It is particularly desirable that one of $R^4$ and $R^5$ is a hydrogen atom, and the other is a methyl group.

In the above general formula (VII-b), each of $X^0$ and $R^4$ may independently represent an alkylene group of 1 to 5 carbon atoms, wherein $X^0$ and $R^4$ are bonded together.

In such a case, within the general formula (VII-b), $R^4$, $X^0$, the oxygen atom to which $X^0$ is bonded, and the carbon atom to which the oxygen atom and $R^4$ are bonded form a cyclic group. This cyclic group is preferably a 4- to 7-membered ring, and more preferably a 4- to 6-membered ring. Specific examples of this cyclic group include a tetrahydropyranyl group and a tetrahydropyranyl group.

In terms of achieving superior resist pattern shape and the like, $R^5$ within the acid-dissociable, dissolution-inhibiting group (VII) is preferably a hydrogen atom, and $R^4$ is preferably a hydrogen atom or a lower alkyl group.

Specific examples of the acid-dissociable, dissolution-inhibiting group (VII) in those cases where $X^0$ represents a lower alkyl group include, namely in those cases where the acid-dissociable, dissolution-inhibiting group is a 1-alkoxyalkyl group, include a 1-methoxyethyl group, 1-ethoxyethyl group, 1-iso-propoxyethyl group, 1-n-butoxyethyl group, 1-tert-butoxyethyl group, methoxymethyl group, ethoxymethyl group, iso-propoxymethyl group, n-butoxymethyl group or tert-butoxymethyl group.

Further, in those cases where $X^0$ represents an aliphatic cyclic group, examples of the acid-dissociable, dissolution-inhibiting group (VII) include a 1-cyclohexyloxyethyl group, 1-(2-adamantyl)oxyethyl group, or 1-(1-adamantyl)oxyethyl group represented by formula (VII-a-1) shown below.

In those cases where $X^0$ represents an aromatic cyclic hydrocarbon group, an example of the acid-dissociable, dissolution-inhibiting group (VII) is 1-(2-naphthyl)oxyethyl group represented by formula (VII-b-1) shown below.

Of the above groups, a 1-ethoxyethyl group is particularly desirable.

[Chemical Formula 58]

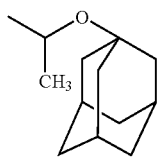

(VII-a-1)

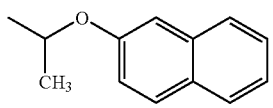

(VII-b-1)

Organic Group that Contains an Acid-Dissociable, Dissolution-Inhibiting Group

In the present description, an "organic group that contains an acid-dissociable, dissolution-inhibiting group" describes a group composed of an acid-dissociable, dissolution-inhibiting group, and a group or atom that does not dissociate under the action of acid (namely a group or atom that does not dissociate under the action of acid, but rather remains bonded to the component (A1) following dissociation of the acid-dissociable, dissolution-inhibiting group).

However, this organic group that contains an acid-dissociable, dissolution-inhibiting group excludes groups containing an acid-dissociable, dissolution-inhibiting group having a 1,3-dioxole skeleton.

There are no particular restrictions on the organic group that contains an acid-dissociable, dissolution-inhibiting group, which may be selected appropriately from the multitude of groups that have been proposed for the resins of resist compositions designed for use with a KrF excimer laser or ArF excimer laser or the like. Examples include organic groups that contain an acid-dissociable, dissolution-inhibiting group described above. For example, an example of an organic group that contains the acid-dissociable, dissolution-inhibiting group (VII) is an organic group (VIII) containing an acid-dissociable, dissolution-inhibiting group shown below.

Examples of this acid-dissociable, dissolution-inhibiting group-containing organic group (VIII) include groups represented by general formula (VIII) shown below.

In the organic group (VIII) of this structure, when acid is generated from the component (B) upon exposure, the action of the acid causes a cleavage of the bond between the oxygen atom bonded to Q, and the carbon atom to which $R^4$ and $R^5$ are bonded, causing dissociation of the group —$C(R^4)(R^5)$—$OX^0$.

[Chemical Formula 59]

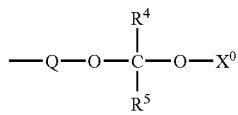

(VIII)

In formula (VIII), $X^0$ represents an aliphatic cyclic group, an aromatic cyclic hydrocarbon group or a lower alkyl group of 1 to 5 carbon atoms, $R^4$ represents a hydrogen atom or a lower alkyl group of 1 to 5 carbon atoms, or alternatively, each of $X^0$ and $R^4$ may independently represent an alkylene group of 1 to 5 carbon atoms, wherein $X^0$ and $R^4$ are bonded together, $R^5$ represents a lower alkyl group or a hydrogen atom, and Q represents a divalent aliphatic cyclic group.

In general formula (VIII), $X^0$, $R^4$ and $R^5$ are the same as defined above for $X^0$, $R^4$ and $R^5$ in general formula (VII-b).

Examples of the divalent aliphatic cyclic group for Q include groups in which an additional one hydrogen atom has been removed from the aliphatic cyclic group described above for $X^0$.

Of the above possibilities, the hydroxyl group hydrogen atom within the structural unit (a7) is preferably protected with a tertiary alkyl group-containing group, is more preferably protected by substitution with a group represented by general formula (II), and is most preferably protected by substitution with a tert-butyloxycarbonyl group (t-boc).

Preferred examples of the structural unit (a7) include the structural units represented by general formula (a7-1) shown below.

[Chemical Formula 60]

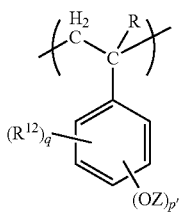

(a7-1)

In formula (a7-1), R, $R^{12}$ and q are same as defined above, and p' represents an integer of 1 to 3. However, p'+q must be not less than 1 and not more than 5. Z represents a tertiary alkyl group-containing group, alkoxyalkyl group, acid-dissociable, dissolution-inhibiting group, or organic group that contains an acid-dissociable, dissolution-inhibiting group. These acid-dissociable, dissolution-inhibiting groups exclude groups that have a 1,3-dioxole skeleton.

In formula (a7-1), R, $R^{12}$ and q are same as defined above for R, $R^{12}$ and q in formula (a5-1).

p' represents an integer of 1 to 3, and is preferably 1. The bonding position for the —OZ group may be any of the o-position, m-position or p-position. When p' is 1, the p-position is preferred in terms of ready availability and low cost. In those cases where p' is 2 or 3, any combination of substitution positions can be used.

The value of p'+q must be not less than 1 and not more than 5.

Z represents a tertiary alkyl group-containing group, alkoxyalkyl group, acid-dissociable, dissolution-inhibiting group, or organic group that contains an acid-dissociable, dissolution-inhibiting group (provided these acid-dissociable, dissolution-inhibiting groups exclude groups that have a 1,3-dioxole skeleton). Examples of these groups are the same as those described above. Of these groups, a tertiary alkyl group-containing group is preferred, a group represented by the above general formula (II) is more preferred, and a tert-butyloxycarbonyl group (t-boc) is particularly desirable.

As the structural unit (a7), either a single type of structural unit may be used alone, or a combination of two or more types of structural units may be used.

In those cases where the component (A1) includes the structural unit (a7), the amount of the structural unit (a7) within the component (A1), based on the combined total of all the structural units that constitute the component (A1), is preferably within a range from 1 to 40 mol %, more preferably from 5 to 40 mol %, still more preferably from 14 to 40 mol %, and most preferably from 20 to 40 mol %. By ensuring that this amount is at least as large as the lower limit of the above range, the solubility of the component (A1) in organic solvents can be improved. On the other hand, by ensuring that the amount is not more than the upper limit of the above range, a good balance can be achieved with the other structural units.

Structural Unit (a8)

The structural unit (a8) is a structural unit derived from a vinylnaphthol.

The structural unit (a8) may be any structural unit formed by the cleavage of the ethylenic double bond of a vinylnaphthol, a compound in which the α-position hydrogen atom of a vinylnaphthol has been substituted with a substituent such as an alkyl group, or a derivative thereof.

Examples of preferred forms of the structural unit (a8) include structural units represented by general formula (a8-1) shown below.

[Chemical Formula 61]

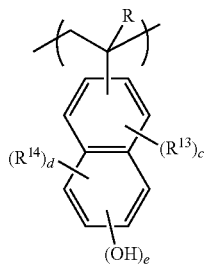

(a8-1)

In formula (a8-1), R represents a hydrogen atom, an alkyl group of 1 to 5 carbon atoms or a halogenated alkyl group of 1 to 5 carbon atoms, each of $R^{13}$ and $R^{14}$ independently represents a halogen atom, an alkyl group of 1 to 5 carbon atoms or a halogenated alkyl group of 1 to 5 carbon atoms, c represents an integer of 0 to 3, d represents an integer of 0 to 2, and e represents an integer of 1 to 3, provided that d+e is an integer of 1 to 4.

In the above formula (a8-1), R, $R^{13}$, $R^{14}$, d and e are the same as defined above for R, $R^{13}$, $R^{14}$, c, d and e in formula (a0-1-20).

In the component (A1), as the structural unit (a8), either a single type of structural unit may be used alone, or a combination of two or more types of structural units may be used.

The amount of the structural unit (a8) within the component (A1), based on the combined total of all the structural units that constitute the component (A1), is preferably within a range from 5 to 90 mol %, more preferably from 10 to 85 mol %, and still more preferably from 30 to 80 mol %. By ensuring that this amount is at least as large as the lower limit of the above range, an appropriate alkali solubility can be achieved. Further, the effects achieved by including the structural unit (a8) (such as improvements in the sensitivity and the etching resistance) manifest more readily. On the other hand, by ensuring that the amount is not more than the upper limit of the above range, a good balance can be achieved with the other structural units.

Structural Unit (a9)

The structural unit (a9) is a structural unit derived from a vinylbenzoic acid.

The structural unit (a9) may be any structural unit formed by the cleavage of the ethylenic double bond of a vinylbenzoic acid, a compound in which the α-position hydrogen atom of a vinylbenzoic acid has been substituted with a substituent such as an alkyl group, or a derivative thereof.

Examples of preferred forms of the structural unit (a9) include structural units in which the —(OH)$_p$ moiety within the aforementioned general formula (a5-1) has been substituted with a —(COOH)$_p$ moiety.

In the component (A1), as the structural unit (a9), either a single type of structural unit may be used alone, or a combination of two or more types of structural units may be used.

The amount of the structural unit (a9) within the component (A1), based on the combined total of all the structural units that constitute the component (A1), is preferably within a range from 1 to 10 mol %.

In the present invention, the component (A1) is a polymeric compound that includes the structural unit (a0), and examples of that polymeric compound include polymers containing the structural unit (a01), polymers containing the structural unit (a02), polymers containing the structural unit (a03), polymers containing the structural unit (a06), copolymers containing the structural unit (a01) and the structural unit (a02), copolymers containing the structural unit (a01) and the structural unit (a03), copolymers containing the structural unit (a02) and the structural unit (a03), and copolymers containing the structural unit (a01), the structural unit (a02) and the structural unit (a03).

Specific examples of the polymers containing the structural unit (a01) include copolymers containing the structural unit (a01) and the structural unit (a5), copolymers containing the structural unit (a01), the structural unit (a5) and the structural unit (a1), copolymers containing the structural unit (a01), the structural unit (a5), the structural unit (a1) and the structural unit (a6), copolymers containing the structural unit (a01), the structural unit (a5) and the structural unit (a6), copolymers containing the structural unit (a01), the structural unit (a5) and the structural unit (a7), and copolymers containing the structural unit (a01), the structural unit (a5), the structural unit (a6) and the structural unit (a7).

Specific examples of the polymers containing the structural unit (a02) include copolymers containing the structural unit (a02) and the structural unit (a8), and copolymers containing the structural unit (a02), the structural unit (a8) and the structural unit (a1).

Specific examples of the polymers containing the structural unit (a03) include copolymers containing the structural unit (a03) and the structural unit (a1), copolymers containing the structural unit (a03) and the structural unit (a2), copolymers containing the structural unit (a03) and the structural unit (a3), copolymers containing the structural unit (a03), the structural unit (a2) and the structural unit (a3), copolymers containing the structural unit (a03), the structural unit (a1) and the structural unit (a2), copolymers containing the structural unit (a03), the structural unit (a1) and the structural unit (a3), copolymers containing the structural unit (a03), the structural unit (a1), the structural unit (a2) and the structural unit (a3), copolymers containing the structural unit (a03) and the structural unit (a5), copolymers containing the structural unit (a03), the structural unit (a5) and the structural unit (a6), copolymers containing the structural unit (a03), the structural unit (a5) and the structural unit (a1), and copolymers containing the structural unit (a03), the structural unit (a5), the structural unit (a1) and the structural unit (a6).

Specific examples of the copolymers containing the structural unit (a01) and the structural unit (a03) include copolymers containing the structural unit (a01), the structural unit (a03) and the structural unit (a6), and copolymers containing the structural unit (a01), the structural unit (a03), the structural unit (a6) and the structural unit (a7).

Specific examples of the polymers containing the structural unit (a06) include copolymers containing the structural unit (a06) and the structural unit (a5), copolymers containing the structural unit (a06) and the structural unit (a1), copolymers containing the structural unit (a06) and the structural unit (a2), copolymers containing the structural unit (a06) and the structural unit (a8), copolymers containing the structural unit (a06), the structural unit (a8) and the structural unit (a6), copolymers containing the structural unit (a06), the structural unit (a01) and the structural unit (a8), and copolymers containing the structural unit (a06), the structural unit (a01), the structural unit (a8) and the structural unit (a6).

As the component (A1) within the component (A), either a single polymeric compound may be used alone, or a combination of two or more polymeric compounds may be used.

Of the various possibilities outlined above, in terms of achieving superior effects for the present invention, the component (A1) is preferably a copolymer containing the structural unit (a5) and the structural unit (a01), or a copolymer containing the structural unit (a8) and the structural unit (a06), and is most preferably a copolymer formed from the structural unit (a5) and the structural unit (a01).

In the present invention, the component (A1) is preferably a polymeric compound containing the types of structural unit combinations shown below.

[Chemical Formula 62]

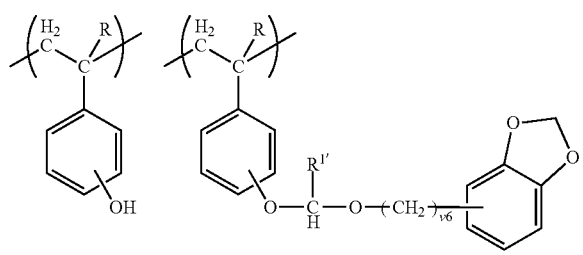

(A1-11)

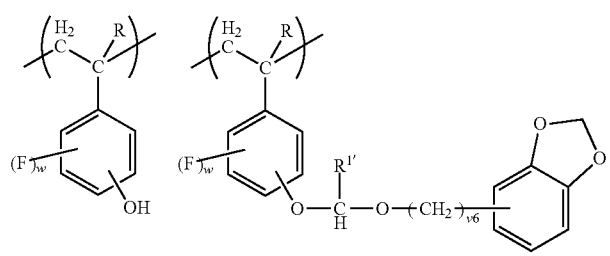

(A1-12)

-continued
[Chemical Formula 63]
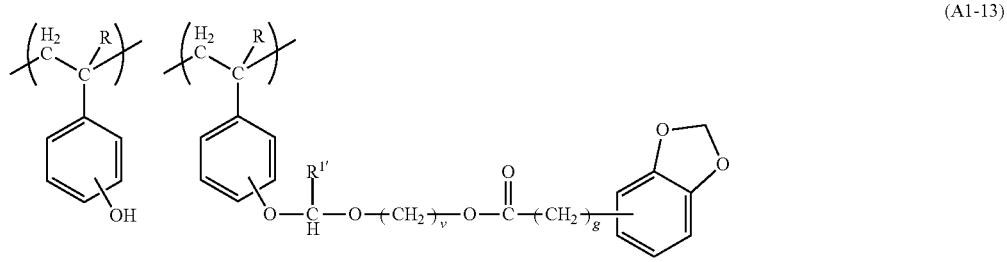
(A1-13)
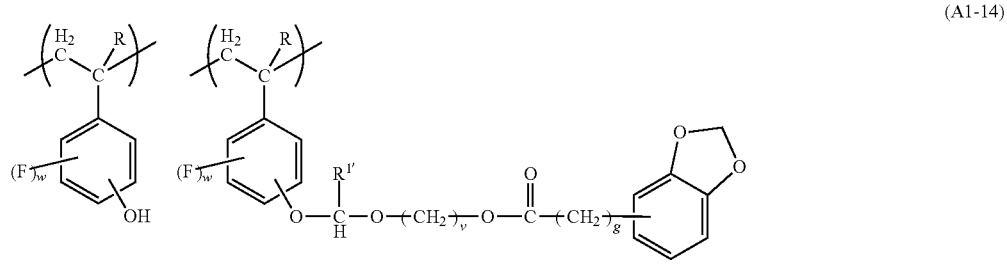
(A1-14)
[Chemical Formula 64]
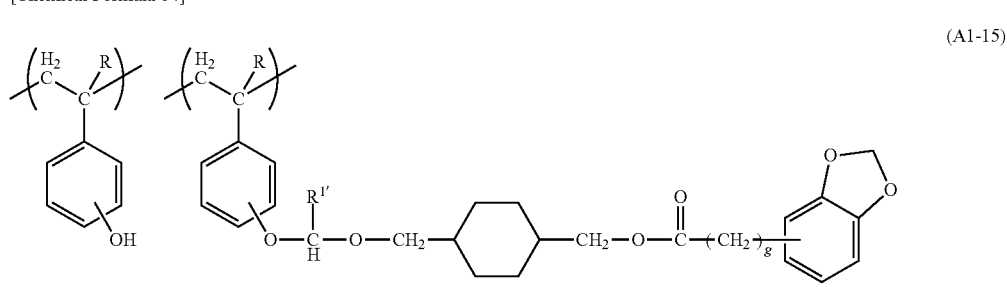
(A1-15)
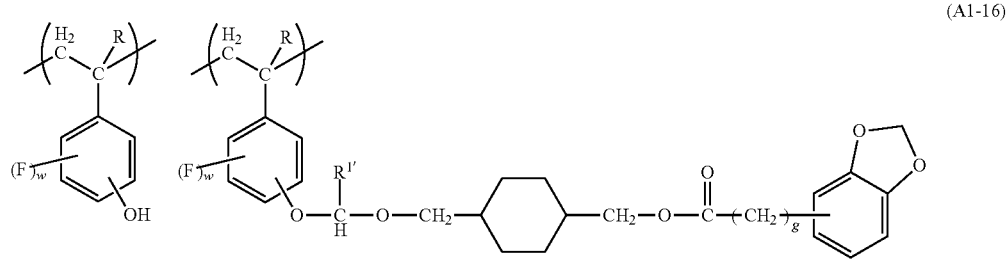
(A1-16)
[Chemical Formula 65]
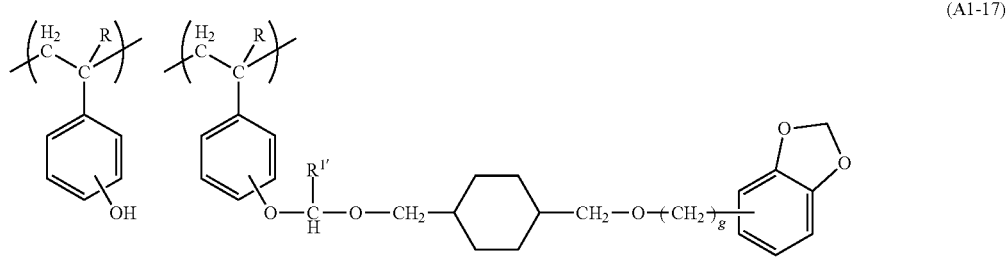
(A1-17)
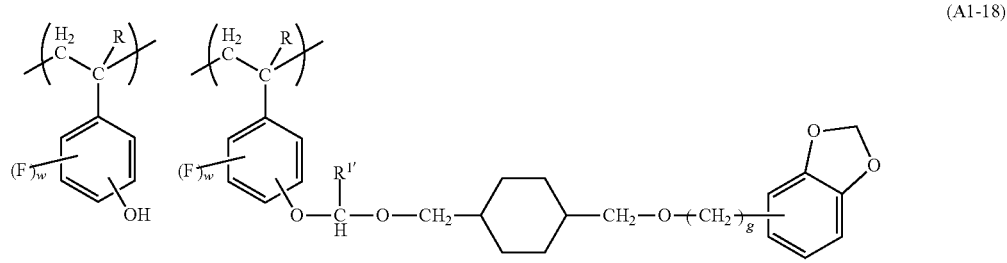
(A1-18)

[Chemical Formula 66]

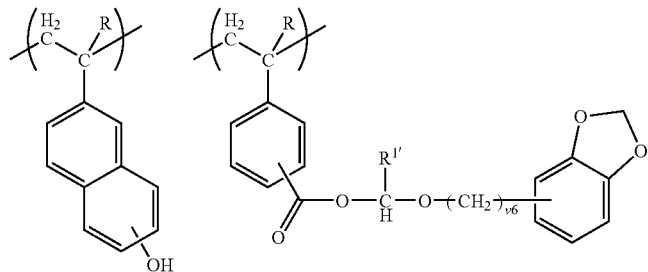

(A1-19)

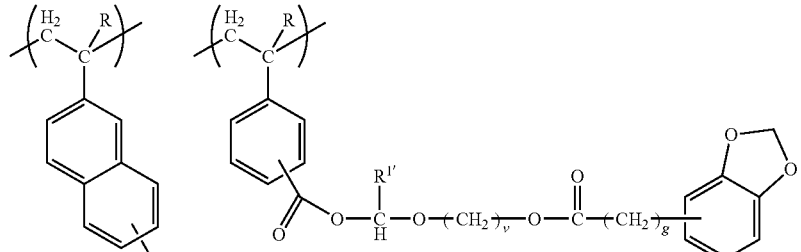

(A1-20)

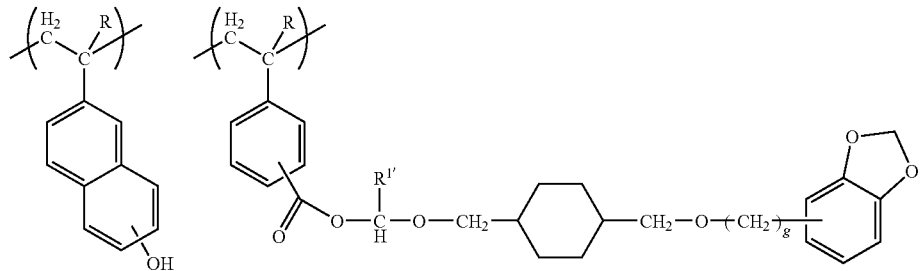

(A1-21)

In formulas (A1-11) to (A1-21), $R^{1'}$ represents a hydrogen atom or an alkyl group of 1 to carbon atoms, v6 represents an integer of 0 to 15, v represents an integer of 2 to 15, and each w independently represents an integer of 1 to 4. g represents an integer of 0 to 5, and R is the same as defined above.

In the above formulas, $R^{1'}$ represents a hydrogen atom or an alkyl group of 1 to 5 carbon atoms, and is preferably a hydrogen atom or a methyl group.

v6 represents an integer of 0 to 15, preferably 0 to 10, more preferably 0 to 5, and most preferably 0 to 2.

v represents an integer of 2 to 15, preferably 2 to 10, more preferably 2 to 5, and most preferably 2.

Each w independently represents an integer of 1 to 4, and preferably an integer of 2 to 4.

g represents an integer of 0 to 5, preferably 0 to 3, and more preferably 0 to 2.

R is the same as defined above, and is preferably a hydrogen atom or a methyl group. The plurality of R groups within a copolymer may be the same or different.

The component (A1) can be obtained, for example, by a conventional radical polymerization or the like of the monomers corresponding with each of the structural units, using a radical polymerization initiator such as azobisisobutyronitrile (AIBN).

Furthermore, in the component (A1), by using a chain transfer agent such as HS—$CH_2$—$CH_2$—$CH_2$—$C(CF_3)_2$—OH during the above polymerization, a —$C(CF_3)_2$—OH group can be introduced at the terminals of the component (A1). Such a copolymer having an introduced hydroxyalkyl group in which some of the hydrogen atoms of the alkyl group have been substituted with fluorine atoms is effective in reducing LWR (line width roughness: a phenomenon in which the line widths of a line pattern lose uniformity). Further, such a copolymer is also effective in reducing developing defects and LER (line edge roughness: unevenness in the side walls of a line pattern).

Further, in those cases where the component (A1) includes a structural unit derived from a hydroxystyrene, the component (A1) can be produced, for example, by reacting a polyhydroxystyrene with a vinyl ether compound containing a structure that includes an "acid-dissociable, dissolution-inhibiting group having a 1,3-dioxole skeleton".

Furthermore, the component (A1) may also be produced by polymerizing a vinylnaphthol with a compound according to the fifth aspect of the present invention (described below).

The weight average molecular weight (Mw) (the polystyrene equivalent value determined by gel permeation chromatography) of the component (A1) is not particularly limited, but is preferably within a range from 1,000 to 50,000, more preferably from 1,500 to 30,000, and most preferably from 2,000 to 20,000. By ensuring that the weight average molecular weight is not more than the upper limit of the above-mentioned range, the polymeric compound (A1) exhibits satisfactory solubility in a resist solvent when used as a resist. On the other hand, ensuring that the weight average molecular weight is at least as large as the lower limit of the above-mentioned range yields more favorable dry etching resistance and cross-sectional shape for the resist pattern.

Further, the dispersity (Mw/Mn) of the component (A1) is preferably within a range from 1.0 to 5.0, more preferably from 1.0 to 3.0, and most preferably from 1.2 to 2.5. Here, Mn represents the number average molecular weight.

[Component (A2)]

As the component (A2), a low molecular weight compound that has a molecular weight of at least 500 but less than 2,000, contains a hydrophilic group, and also contains an acid-dissociable, dissolution-inhibiting group such as the groups exemplified above in the description of the component (A1) is preferred. Specific examples of the component (A2) include compounds containing a plurality of phenol structures, in which a portion of the hydroxyl group hydrogen atoms have been substituted with the acid-dissociable, dissolution-inhibiting groups.

Preferred examples of the component (A2) include low molecular weight phenolic compounds in which a portion of the hydroxyl group hydrogen atoms have been substituted with an aforementioned acid-dissociable, dissolution-inhibiting group. These types of compounds are known, for example, as sensitizers or heat resistance improvers for use in non-chemically amplified g-line or i-line resists.

Specific examples of the low molecular weight phenol compounds include bis(4-hydroxyphenyl)methane, bis(2,3,4-trihydroxyphenyl)methane, 2-(4-hydroxyphenyl)-2-(4'-hydroxyphenyl)propane, 2-(2,3,4-trihydroxyphenyl)-2-(2',3',4'-trihydroxyphenyl)propane, tris(4-hydroxyphenyl)methane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, bis(4-hydroxy-2,5-dimethylphenyl)-3,4-dihydroxyphenylmethane, bis(4-hydroxy-3-methylphenyl)-3,4-dihydroxyphenylmethane, bis(3-cyclohexyl-4-hydroxy-6-methylphenyl)-4-hydroxyphenylmethane, bis(3-cyclohexyl-4-hydroxy-6-methylphenyl)-3,4-dihydroxyphenylmethane, 1-[1-(4-hydroxyphenyl)isopropyl]-4-[1,1-bis(4-hydroxyphenyl)ethyl]benzene, and dimers, trimers and tetramers of formalin condensation products of phenols such as phenol, m-cresol, p-cresol and xylenol. Of course, this is not a restrictive list.

There are no particular limitations on the acid-dissociable, dissolution-inhibiting group, and examples include the groups exemplified above.

In the component (A), as the component (A2), one type of compound may be used alone, or two or more types of compounds may be used in combination.

In the positive resist composition of the present invention, as the component (A), one type of component may be used alone, or two or more types of components may be used in combination.

In the resist composition of the present invention, the amount of the component (A) can be appropriately adjusted depending on factors such as the thickness of the resist film that is to be formed.

<Component (B)>

In the present invention, there are no particular limitations on the component (B), and any of the known acid generators used in conventional chemically amplified resist compositions can be used. Examples of these acid generators are numerous, and include onium salt acid generators such as iodonium salts and sulfonium salts, oxime sulfonate acid generators, diazomethane acid generators such as bisalkyl or bisaryl sulfonyl diazomethanes and poly(bis-sulfonyl)diazomethanes, nitrobenzylsulfonate acid generators, iminosulfonate acid generators, and disulfone acid generators.

As an onium salt acid generator, a compound represented by general formula (b-1) or (b-2) shown below can be used.

[Chemical Formula 67]

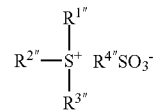

(b-1)

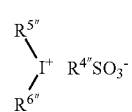

(b-2)

In the formulas above, $R^{1\prime\prime}$ to $R^{3\prime\prime}$, $R^{5\prime\prime}$ and $R^{6\prime\prime}$ each independently represents an aryl group or alkyl group, wherein two of $R^{1\prime\prime}$ to $R^{3\prime\prime}$ may be bonded to each other to form a ring with the sulfur atom, and $R^{4\prime\prime}$ represents an alkyl group, halogenated alkyl group, aryl group or alkenyl group which may have a substituent, with the provision that at least one of $R^{1\prime\prime}$ to $R^{3\prime\prime}$ represents an aryl group, and at least one of $R^{5\prime\prime}$ and $R^{6\prime\prime}$ represents an aryl group.

In formula (b-1), $R^{1\prime\prime}$ to $R^{3\prime\prime}$ each independently represents an aryl group or an alkyl group. In formula (b-1), two of $R^{1\prime\prime}$ to $R^{3\prime\prime}$ may be bonded to each other to form a ring with the sulfur atom.

Further, among $R^{1\prime\prime}$ to $R^{3\prime\prime}$, at least one group represents an aryl group. Among $R^{1\prime\prime}$ to $R^{3\prime\prime}$, two or more groups are preferably aryl groups, and it is particularly desirable that all of $R^{1\prime\prime}$ to $R^{3\prime\prime}$ are aryl groups.

The aryl group for $R^{1\prime\prime}$ to $R^{3\prime\prime}$ is not particularly limited. For example, aryl groups having 6 to 20 carbon atoms may be used, in which part or all of the hydrogen atoms of the aryl group may or may not be substituted with alkyl groups, alkoxy groups, halogen atoms or hydroxyl groups.

The aryl group is preferably an aryl group having 6 to 10 carbon atoms because it enables synthesis to be performed at low cost. Specific examples thereof include a phenyl group and a naphthyl group.

The alkyl group with which hydrogen atoms of the aryl group may be substituted is preferably an alkyl group having 1 to 5 carbon atoms, and most preferably a methyl group, ethyl group, propyl group, n-butyl group or tert-butyl group.

The alkoxy group with which hydrogen atoms of the aryl group may be substituted is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

The halogen atom with which hydrogen atoms of the aryl group may be substituted is preferably a fluorine atom.

The alkyl group for $R^{1\prime\prime}$ to $R^{3\prime\prime}$ is not particularly limited and includes, for example, linear, branched and cyclic alkyl groups of 1 to 10 carbon atoms. In terms of achieving excellent resolution, the alkyl group preferably has 1 to 5 carbon atoms. Specific examples thereof include a methyl group, ethyl group, n-propyl group, isopropyl group, n-butyl group, isobutyl group, n-pentyl group, cyclopentyl group, hexyl group, cyclohexyl group, nonyl group or decyl group, and a methyl group is particularly preferable because it yields excellent resolution and enables synthesis to be performed at low cost.

When two of $R^{1\prime\prime}$ to $R^{3\prime\prime}$ in formula (b-1) are bonded to each other to form a ring with the sulfur atom, it is preferable that the two of $R^{1\prime\prime}$ to $R^{3\prime\prime}$ form a 3- to 10-membered ring including the sulfur atom, and it is particularly desirable that the two of $R^{1\prime\prime}$ to $R^{3\prime\prime}$ form a 5- to 7-membered ring including the sulfur atom.

When two of $R^{1\prime\prime}$ to $R^{3\prime\prime}$ in formula (b-1) are bonded to each other to form a ring with the sulfur atom, the remaining one of $R^{1\prime\prime}$ to $R^{3\prime\prime}$ is preferably an aryl group. Examples of this aryl group include the same groups as the aryl groups mentioned above for $R^{1\prime\prime}$ to $R^{3\prime\prime}$.

Preferred examples of the cation moiety for the compound represented by general formula (b-1) include cation moieties represented by formulas (I-1-1) to (I-1-10) shown below. Among these, a cation moiety having a triphenylmethane skeleton, such as a cation moiety represented by any one of formulas (I-1-1) to (I-1-8) shown below is particularly desirable.

In formulas (I-1-9) and (I-1-10), each of $R^9$ and $R^{10}$ independently represents a phenyl group which may have a substituent, or a naphthyl group.

u is an integer of 1 to 3, and most preferably 1 or 2.

[Chemical Formula 68]

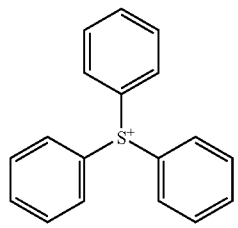

(I-1-1)

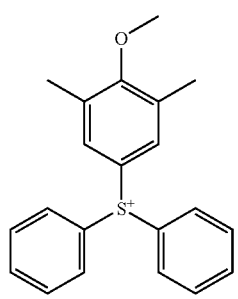

(I-1-2)

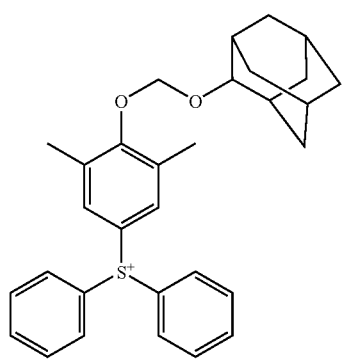

(I-1-3)

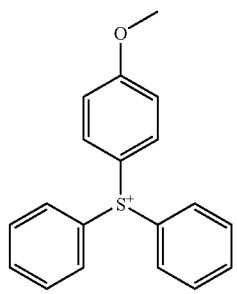

(I-1-4)

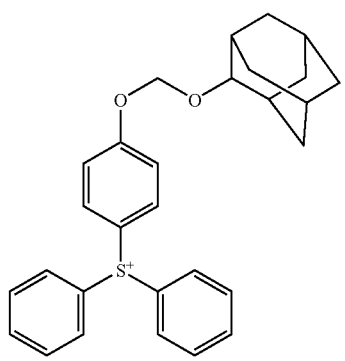

(I-1-5)

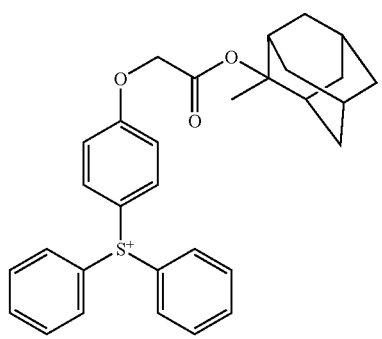

(I-1-6)

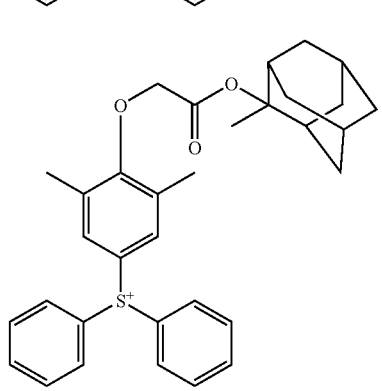

(I-1-7)

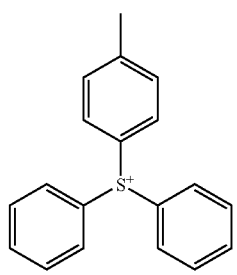

(I-1-8)

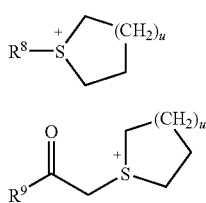

(I-1-9)

(I-1-10)

$R^{4'''}$ represents an alkyl group, halogenated alkyl group, aryl group or alkenyl group which may have a substituent.

The alkyl group for $R^{4'''}$ may be any of linear, branched or cyclic.

The linear or branched alkyl group preferably has 1 to 10 carbon atoms, more preferably 1 to 8 carbon atoms, and most preferably 1 to 4 carbon atoms.

The cyclic alkyl group preferably has 4 to 15 carbon atoms, more preferably 4 to 10 carbon atoms, and most preferably 6 to 10 carbon atoms.

Examples of the halogenated alkyl group for $R^{4'''}$ include groups in which part or all of the hydrogen atoms of an aforementioned linear, branched or cyclic alkyl group have been substituted with halogen atoms. Examples of the halogen atom include a fluorine atom, chlorine atom, bromine atom or iodine atom, and a fluorine atom is preferable.

In the halogenated alkyl group, the percentage of the number of halogen atoms based on the total number of halogen atoms and hydrogen atoms (namely, the halogenation ratio (%)) is preferably within a range from 10 to 100%, more preferably from 50 to 100%, and most preferably 100%. A higher halogenation ratio is preferable because the acid strength increases.

The aryl group for $R^{4'''}$ is preferably an aryl group of 6 to 20 carbon atoms.

The alkenyl group for $R^{4'''}$ is preferably an alkenyl group of 2 to 10 carbon atoms.

With respect to $R^{4'''}$, the expression "may have a substituent" means that part or all of the hydrogen atoms within the aforementioned linear, branched or cyclic alkyl group, halogenated alkyl group, aryl group or alkenyl group may be substituted with substituents (atoms other than hydrogen atoms, or groups).

$R^{4'''}$ may have one substituent, or two or more substituents.

Examples of the substituent include a halogen atom, a hetero atom, an alkyl group, and a group represented by the formula X-Q²- (wherein Q² represents a divalent linking group containing an oxygen atom, and X represents a hydrocarbon group of 3 to 30 carbon atoms which may have a substituent).

Examples of halogen atoms and alkyl groups as substituents for $R^{4'''}$ include the same halogen atoms and alkyl groups as those described above with respect to the halogenated alkyl group for $R^{4'''}$.

Examples of hetero atoms include an oxygen atom, a nitrogen atom, and a sulfur atom.

In the group represented by formula X-$Q^2$-, $Q^2$ represents a divalent linking group containing an oxygen atom.

$Q^2$ may contain atoms other than the oxygen atom. Examples of atoms other than an oxygen atom include a carbon atom, a hydrogen atom, a sulfur atom and a nitrogen atom.

Examples of divalent linking groups containing an oxygen atom include non-hydrocarbon, oxygen atom-containing linking groups such as an oxygen atom (an ether bond, —O—), an ester bond (—C(=O)—O—), an amido bond (—C(=O)—NH—), a carbonyl group (—C(=O)—), a carbonate linkage (—O—C(=O)—O—), and combinations of the aforementioned non-hydrocarbon, hetero atom-containing linking groups with an alkylene group.

Specific examples of the combinations of the aforementioned non-hydrocarbon, hetero atom-containing linking groups and an alkylene group include —$R^{91}$—O—, —$R^{92}$—O—C(=O)—, —C(=O)—O—$R^{93}$—O—C(=O)— (wherein each of $R^{91}$ to $R^{93}$ independently represents an alkylene group).

The alkylene group for $R^{91}$ to $R^{93}$ is preferably a linear or branched alkylene group, and preferably has 1 to 12 carbon atoms, more preferably 1 to 5 carbon atoms, and most preferably 1 to 3 carbon atoms.

Specific examples of alkylene groups include a methylene group [—CH₂—], alkylmethylene groups such as —CH(CH₃)—, —CH(CH₂CH₃)—, —C(CH₃)₂—, —C(CH₃)(CH₂CH₃)—, —C(CH₃)(CH₂CH₂CH₃)— and —C(CH₂CH₃)₂—, an ethylene group [—CH₂CH₂—], alkylethylene groups such as —CH(CH₃)CH₂—, —CH(CH₃)CH(CH₃)—, —C(CH₃)₂CH₂— and —CH(CH₂CH₃)CH₂—, a trimethylene group (n-propylene group) [—CH₂CH₂CH₂—], alkyltrimethylene groups such as —CH(CH₃)CH₂CH₂— and —CH₂CH(CH₃)CH₂—, a tetramethylene group [—CH₂CH₂CH₂CH₂—], alkyltetramethylene groups such as —CH(CH₃)CH₂CH₂CH₂— and —CH₂CH(CH₃)CH₂CH₂—, and a pentamethylene group [—CH₂CH₂CH₂CH₂CH₂—].

$Q^2$ is preferably a divalent linking group containing an ester linkage or ether linkage, and more preferably a group represented by —$R^{91}$—O—, —$R^{92}$—O—C(=O)— or —C(=O)—O—$R^{93}$—O—C(=O)—.

In the group represented by the formula X-$Q^2$-, the hydrocarbon group for X may be either an aromatic hydrocarbon group or an aliphatic hydrocarbon group.

The aromatic hydrocarbon group is a hydrocarbon group having an aromatic ring. The aromatic hydrocarbon ring preferably has 3 to 30 carbon atoms, more preferably 5 to 30, still more preferably 5 to 20, still more preferably 6 to 15, and most preferably 6 to 12 carbon atoms. Here, the number of carbon atoms within a substituent(s) is not included in the number of carbon atoms of the aromatic hydrocarbon group.

Specific examples of the aromatic hydrocarbon group include aryl groups, which are aromatic hydrocarbon rings having one hydrogen atom removed therefrom, such as a phenyl group, biphenyl group, fluorenyl group, naphthyl group, anthryl group or phenanthryl group, and alkylaryl groups such as a benzyl group, phenethyl group, 1-naphthylmethyl group, 2-naphthylmethyl group, 1-naphthylethyl group or 2-naphthylethyl group. The alkyl chain within the arylalkyl group preferably has 1 to 4 carbon atoms, more preferably 1 or 2 carbon atoms, and most preferably 1 carbon atom.

The aromatic hydrocarbon group may have a substituent. For example, part of the carbon atoms constituting the aromatic ring within the aromatic hydrocarbon group may be substituted with a hetero atom, or a hydrogen atom bonded to the aromatic ring within the aromatic hydrocarbon group may be substituted with a substituent.

Examples of the former include heteroaryl groups in which some of the carbon atoms constituting the ring within an aforementioned aryl group have been substituted with a hetero atom such as an oxygen atom, a sulfur atom or a nitrogen atom, and heteroarylalkyl groups in which a portion of the carbon atoms constituting the aromatic hydrocarbon ring within an aforementioned arylalkyl group have been substituted with an aforementioned hetero atom.

In the latter example, examples of the substituent for the aromatic hydrocarbon group include an alkyl group, an alkoxy group, a halogen atom, a halogenated alkyl group, a hydroxyl group or an oxygen atom (=O) or the like.

The alkyl group as the substituent for the aromatic hydrocarbon group is preferably an alkyl group of 1 to 5 carbon atoms, and a methyl group, ethyl group, propyl group, n-butyl group or tert-butyl group is particularly desirable.

The alkoxy group as the substituent for the aromatic hydrocarbon group is preferably an alkoxy group having 1 to 5 carbon atoms, is more preferably a methoxy group, ethoxy group, n-propoxy group, iso-propoxy group, n-butoxy group or tert-butoxy group, and is most preferably a methoxy group or an ethoxy group.

Examples of the halogen atom as the substituent for the aromatic hydrocarbon group include a fluorine atom, a chlorine atom, a bromine atom and an iodine atom, and a fluorine atom is preferable.

Examples of the halogenated alkyl group as the substituent for the aromatic hydrocarbon group includes a group in which part or all of the hydrogen atoms within the aforementioned alkyl group have been substituted with the aforementioned halogen atoms.

The aliphatic hydrocarbon group for X may be either a saturated aliphatic hydrocarbon group, or an unsaturated aliphatic hydrocarbon group. Further, the aliphatic hydrocarbon group may be linear, branched or cyclic.

In the aliphatic hydrocarbon group for X, a portion of the carbon atoms constituting the aliphatic hydrocarbon group may be substituted with a substituent group containing a hetero atom, or part or all of the hydrogen atoms constituting the aliphatic hydrocarbon group may be substituted with a substituent group containing a hetero atom.

As this "hetero atom" within X, there is no particular limitation as long as it is an atom other than a carbon atom and a hydrogen atom. Examples of the hetero atom include a halogen atom, an oxygen atom, a sulfur atom and a nitrogen atom. Examples of the halogen atom include a fluorine atom, a chlorine atom, an iodine atom and a bromine atom.

The substituent group containing a hetero atom may consist solely of the hetero atom, or may be a group containing a group or atom other than a hetero atom.

Specific examples of the substituent group for substituting a portion of the carbon atoms include —O—, —C(=O)—O—, —C(=O)—, —O—C(=O)—O—, —C(=O)—NH—, —NH— (wherein H may be replaced with a substituent such as an alkyl group or an acyl group), —S—, —S(=O)$_2$— and —S(=O)$_2$—O—. When the aliphatic hydrocarbon group is cyclic, the aliphatic hydrocarbon group may contain any of these substituent groups within the ring structure.

Examples of the substituent group for substituting part or all of the hydrogen atoms include an alkoxy group, a halogen atom, a halogenated alkyl group, a hydroxyl group, an oxygen atom (=O) and a cyano group.

The alkoxy group is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the halogen atom include a fluorine atom, a chlorine atom, a bromine atom and an iodine atom, and a fluorine atom is preferable.

Examples of the halogenated alkyl group includes a group in which part or all of the hydrogen atoms within an alkyl group of 1 to 5 carbon atoms (such as a methyl group, ethyl group, propyl group, n-butyl group or tert-butyl group) have been substituted with the aforementioned halogen atoms.

As the aliphatic hydrocarbon group, a linear or branched saturated hydrocarbon group, a linear or branched monovalent unsaturated hydrocarbon group, or a cyclic aliphatic hydrocarbon group (aliphatic cyclic group) is preferable.

The linear saturated hydrocarbon group (alkyl group) preferably has 1 to 20 carbon atoms, more preferably 1 to 15 carbon atoms, and most preferably 1 to 10 carbon atoms. Specific examples include a methyl group, ethyl group, propyl group, butyl group, pentyl group, hexyl group, heptyl group, octyl group, nonyl group, decyl group, undecyl group, dodecyl group, tridecyl group, isotridecyl group, tetradecyl group, pentadecyl group, hexadecyl group, isohexadecyl group, heptadecyl group, octadecyl group, nonadecyl group, eicosyl group, heneicosyl group or docosyl group.

The branched saturated hydrocarbon group (alkyl group) preferably has 3 to 20 carbon atoms, more preferably 3 to 15 carbon atoms, and most preferably 3 to 10 carbon atoms. Specific examples include a 1-methylethyl group, 1-methylpropyl group, 2-methylpropyl group, 1-methylbutyl group, 2-methylbutyl group, 3-methylbutyl group, 1-ethylbutyl group, 2-ethylbutyl group, 1-methylpentyl group, 2-methylpentyl group, 3-methylpentyl group or 4-methylpentyl group.

The unsaturated hydrocarbon group preferably has 2 to 10 carbon atoms, more preferably 2 to 5 carbon atoms, still more preferably 2 to 4 carbon atoms, and most preferably 3 carbon atoms. Examples of linear monovalent unsaturated hydrocarbon groups include a vinyl group, a propenyl group (an allyl group) and a butynyl group. Examples of branched monovalent unsaturated hydrocarbon groups include a 1-methylpropenyl group and a 2-methylpropenyl group.

Among the above-mentioned examples, as the unsaturated hydrocarbon group, a propenyl group is particularly desirable.

The aliphatic cyclic group may be either a monocyclic group or a polycyclic group. The aliphatic cyclic group preferably has 3 to 30 carbon atoms, more preferably 5 to 30, still more preferably 5 to 20, still more preferably 6 to 15, and most preferably 6 to 12 carbon atoms.

Examples of the aliphatic cyclic group include groups in which one or more hydrogen atoms have been removed from a monocycloalkane or a polycycloalkane such as a bicycloalkane, tricycloalkane or tetracycloalkane. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane.

When the aliphatic cyclic group does not contain a hetero atom-containing substituent group in the ring structure thereof, the aliphatic cyclic group is preferably a polycyclic group, more preferably a group in which one or more hydrogen atoms have been removed from a polycycloalkane, and most preferably a group in which one or more hydrogen atoms have been removed from adamantane.

When the aliphatic cyclic group contains a hetero atom-containing substituent group in the ring structure thereof, the hetero atom-containing substituent group is preferably —O—, —C(=O)—O—, —S—, —S(=O)$_2$— or —S(=O)$_2$—O—. Specific examples of such aliphatic cyclic groups include the aliphatic cyclic groups represented by formulas (L1) to (L5) and (S1) to (S4) shown below.

[Chemical Formula 69]

(L1) 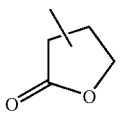

(L2) 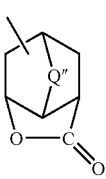

(L3) 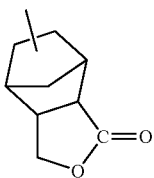

(L4) 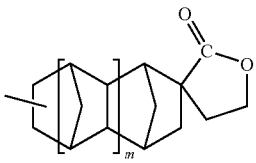

(L5) 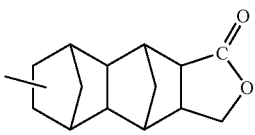

(S1) 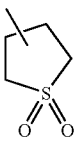

(S2) 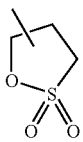

(S3) 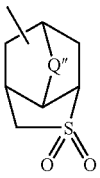

(S4) 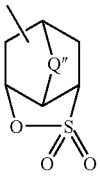

In the formulas, Q" represents an alkylene group of 1 to 5 carbon atoms, —O—, —S—, —O—$R^{94}$— or —S—$R^{95}$— (wherein each of $R^{94}$ and $R^{95}$ independently represents an alkylene group of 1 to 5 carbon atoms), and m represents 0 or 1.

Examples of the alkylene groups for Q", $R^{94}$ and $R^{95}$ include the same alkylene groups as those described above for $R^{91}$ to $R^{93}$.

In these aliphatic cyclic groups, part of the hydrogen atoms bonded to the carbon atoms that constitute the ring structure may be substituted with a substituent. Examples of this substituent include an alkyl group, an alkoxy group, a halogen atom, a halogenated alkyl group, a hydroxyl group and an oxygen atom (=O).

As the alkyl group, an alkyl group of 1 to 5 carbon atoms is preferable, and a methyl group, ethyl group, propyl group, n-butyl group or tert-butyl group is particularly desirable.

Examples of the alkoxy group and the halogen atom include the same groups as those exemplified above for the substituent group used for substituting part or all of the hydrogen atoms.

Of the above options, X is preferably a cyclic group which may have a substituent. This cyclic group may be either an aromatic hydrocarbon group which may have a substituent, or an aliphatic cyclic group which may have a substituent, although an aliphatic cyclic group which may have a substituent is preferable As the aromatic hydrocarbon group, a naphthyl group which may have a substituent or a phenyl group which may have a substituent is preferable.

As the aliphatic cyclic group which may have a substituent, an aliphatic polycyclic group which may have a substituent is preferable. As this aliphatic polycyclic group, groups in which one or more hydrogen atoms have been removed from an aforementioned polycycloalkane, and groups represented by formulas (L2) to (L5), and (S3) and (S4) above are preferable.

Further, in the present invention, X is preferably a group with a structure having a similar skeleton to that of the $R^{11}$ group within the structural unit (a0) of the aforementioned component (A1), as such groups yield improved lithography properties and a superior resist pattern shape. Of such groups, those containing a polar region are particularly desirable.

Examples of these groups containing a polar region include groups in which a portion of the carbon atoms that constitute the aliphatic cyclic group of an aforementioned group X have been substituted with a substituent containing a hetero atom, namely with a substituent such as —O—, —C(=O)—O—, —C(=O)—, —C(=O)—NH—, —NH— (wherein H may be replaced with a substituent such as an alkyl group or acyl group or the like), —S—, —S(=O)$_2$— or —S(=O)$_2$—O.

In the present invention, $R^{4'''}$ preferably has X-$Q^2$- as a substituent. In such a case, $R^{4'''}$ is preferably a group represented by the formula X-$Q^2$-$Y^3$— (wherein $Q^2$ and X are the same as defined above, and $Y^3$ represents an alkylene group of 1 to 4 carbon atoms which may have a substituent, or a fluorinated alkylene group of 1 to 4 carbon atoms which may have a substituent).

In the group represented by the formula X-$Q^2$-$Y^3$—, examples of the alkylene group represented by $Y^3$ include those alkylene groups described above for $Q^2$ in which the number of carbon atoms is from 1 to 4.

Examples of the fluorinated alkylene group for $Y^3$ include groups in which part or all of the hydrogen atoms of an aforementioned alkylene group have been substituted with fluorine atoms.

Specific examples of $Y^3$ include —$CF_2$—, —$CF_2CF_2$—, —$CF_2CF_2CF_2$—, —$CF(CF_3)CF_2$—, —$CF(CF_2CF_3)$—, —$C(CF_3)_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—, —$CF(CF_2CF_2CF_3)$—, —$C(CF_3)(CF_2CF_3)$—, —CHF—, —$CH_2CF_2$—, —CH$_2$CH$_2$CF$_2$—, —CH$_2$CF$_2$CF$_2$—, —CH(CF$_3$)CH$_2$—, —CH(CF$_2$CF$_3$)—, —C(CH$_3$)(CF$_3$)—, —CH$_2$CH$_2$CH$_2$CF$_2$—, —CH$_2$CH$_2$CF$_2$CF$_2$—, —CH(CF$_3$)CH$_2$CH$_2$—, —CH$_2$CH(CF$_3$)CH$_2$—, —CH(CF$_3$)CH(CF$_3$)—, —C(CF$_3$)$_2$CH$_2$—, —CH$_2$—, —CH$_2$CH$_2$—, —CH$_2$CH$_2$CH$_2$—, —CH(CH$_3$)CH$_2$—, —CH(CH$_2$CH$_3$)—, —C(CH$_3$)$_2$—, —CH$_2$CH$_2$CH$_2$CH$_2$—, —CH(CH$_3$)CH$_2$CH$_2$—, —CH$_2$CH(CH$_3$)CH$_2$—, —CH(CH$_3$)CH(CH$_3$)—, —C(CH$_3$)$_2$CH$_2$—, —CH(CH$_2$CH$_3$)CH$_2$—, —CH(CH$_2$CH$_2$CH$_3$)— and —C(CH$_3$)(CH$_2$CH$_3$)—.

$Y^3$ is preferably a fluorinated alkylene group, and particularly preferably a fluorinated alkylene group in which the carbon atom bonded to the adjacent sulfur atom is fluorinated. Examples of such fluorinated alkylene groups include —CF$_2$—, —CF$_2$CF$_2$—, —CF$_2$CF$_2$CF$_2$—, —CF(CF$_3$)CF$_2$—, —CF$_2$CF$_2$CF$_2$CF$_2$—, —CF(CF$_3$)CF$_2$CF$_2$—, —CF$_2$CF(CF$_3$)CF$_2$—, —CF(CF$_3$)CF(CF$_3$)—, —C(CF$_3$)$_2$CF$_2$—, —CF(CF$_2$CF$_3$)CF$_2$—, —CH$_2$CF$_2$—, —CH$_2$CH$_2$CF$_2$—, —CH$_2$CF$_2$CF$_2$—, —CH$_2$CH$_2$CH$_2$CF$_2$—, —CH$_2$CH$_2$CF$_2$CF$_2$— and —CH$_2$CF$_2$CF$_2$CF$_2$—.

Of these, —CF$_2$—, —CF$_2$CF$_2$—, —CF$_2$CF$_2$CF$_2$— or CH$_2$CF$_2$CF$_2$— is preferable, —CF$_2$—, —CF$_2$CF$_2$— or —CF$_2$CF$_2$CF$_2$— is more preferable, and —CF$_2$— is particularly desirable.

The alkylene group or fluorinated alkylene group may have a substituent. The expression that the alkylene group or fluorinated alkylene group "may have a substituent" means that part or all of the hydrogen atoms or fluorine atoms in the alkylene group or fluorinated alkylene group may be substituted, either with atoms other than hydrogen atoms and fluorine atoms, or with groups.

Examples of substituents which the alkylene group or fluorinated alkylene group may have include alkyl groups of 1 to 4 carbon atoms, alkoxy groups of 1 to 4 carbon atoms, and a hydroxyl group.

In formula (b-2), $R^{5\prime\prime\prime}$ and $R^{6\prime\prime\prime}$ each independently represent an aryl group or alkyl group. At least one of $R^{5\prime\prime\prime}$ and $R^{6\prime\prime\prime}$ represents an aryl group. It is preferable that both of $R^{5\prime\prime\prime}$ and $R^{6\prime\prime\prime}$ represent aryl groups.

Examples of the aryl group for $R^{5\prime\prime\prime}$ and $R^{6\prime\prime\prime}$ include the same aryl groups as those listed above for $R^{1\prime\prime\prime}$ to $R^{3\prime\prime\prime}$.

Examples of the alkyl group for $R^{5\prime\prime\prime}$ and $R^{6\prime\prime\prime}$ include the same alkyl groups as those listed above for $R^{1\prime\prime\prime}$ to $R^{3\prime\prime\prime}$.

It is particularly desirable that both of $R^{5\prime\prime\prime}$ and $R^{6\prime\prime\prime}$ represent phenyl groups.

As $R^{4\prime\prime\prime}$ in formula (b-2), the same groups as those mentioned above for $R^{4\prime\prime\prime}$ in formula (b-1) can be used.

Specific examples of suitable onium salt acid generators represented by formula (b-1) or (b-2) include diphenyliodonium trifluoromethanesulfonate or nonafluorobutanesulfonate, bis(4-tert-butylphenyl)iodonium trifluoromethanesulfonate or nonafluorobutanesulfonate, triphenylsulfonium trifluoromethanesulfonate, heptafluoropropanesulfonate or nonafluorobutanesulfonate, tri(4-methylphenyl)sulfonium trifluoromethanesulfonate, heptafluoropropanesulfonate or nonafluorobutanesulfonate, dimethyl(4-hydroxynaphthyl)sulfonium trifluoromethanesulfonate, heptafluoropropanesulfonate or nonafluorobutanesulfonate, monophenyldimethylsulfonium trifluoromethanesulfonate, heptafluoropropanesulfonate or nonafluorobutanesulfonate, diphenylmonomethylsulfonium trifluoromethanesulfonate, heptafluoropropanesulfonate or nonafluorobutanesulfonate, (4-methylphenyl)diphenylsulfonium trifluoromethanesulfonate, heptafluoropropanesulfonate or nonafluorobutanesulfonate, (4-methoxyphenyl)diphenylsulfonium trifluoromethanesulfonate, heptafluoropropanesulfonate or nonafluorobutanesulfonate, tri(4-tert-butyl)phenylsulfonium trifluoromethanesulfonate, heptafluoropropanesulfonate or nonafluorobutanesulfonate, diphenyl(1-(4-methoxy)naphthyl)sulfonium trifluoromethanesulfonate, heptafluoropropanesulfonate or nonafluorobutanesulfonate, di(1-naphthyl)phenylsulfonium trifluoromethanesulfonate, heptafluoropropanesulfonate, or nonafluorobutanesulfonate, 1-phenyltetrahydrothiophenium trifluoromethanesulfonate, heptafluoropropanesulfonate or nonafluorobutanesulfonate, 1-(4-methylphenyl)tetrahydrothiophenium trifluoromethanesulfonate, heptafluoropropanesulfonate or nonafluorobutanesulfonate, 1-(3,5-dimethyl-4-hydroxyphenyl)tetrahydrothiophenium trifluoromethanesulfonate, heptafluoropropanesulfonate or nonafluorobutanesulfonate, 1-(4-methoxynaphthalene-1-yl)tetrahydrothiophenium trifluoromethanesulfonate, heptafluoropropanesulfonate or nonafluorobutanesulfonate, 1-(4-ethoxynaphthalene-1-yl)tetrahydrothiophenium trifluoromethanesulfonate, heptafluoropropanesulfonate or nonafluorobutanesulfonate, 1-(4-n-butoxynaphthalene-1-yl)tetrahydrothiophenium trifluoromethanesulfonate, heptafluoropropanesulfonate or nonafluorobutanesulfonate, 1-phenyltetrahydrothiopyranium trifluoromethanesulfonate, heptafluoropropanesulfonate or nonafluorobutanesulfonate, 1-(4-hydroxyphenyl)tetrahydrothiopyranium trifluoromethanesulfonate, heptafluoropropanesulfonate or nonafluorobutanesulfonate, 1-(3,5-dimethyl-4-hydroxyphenyl)tetrahydrothiopyranium trifluoromethanesulfonate, heptafluoropropanesulfonate or nonafluorobutanesulfonate, and 1-(4-methylphenyl)tetrahydrothiopyranium trifluoromethanesulfonate, heptafluoropropanesulfonate or nonafluorobutanesulfonate.

It is also possible to use onium salts in which the anion moiety of these onium salts has been replaced by an alkylsulfonate such as methanesulfonate, n-propanesulfonate, n-butanesulfonate, or n-octanesulfonate.

Further, onium salts in which the anion moiety of these onium salts has been replaced by an anion moiety containing an alicyclic group represented by any one of chemical formulas (b0-1) to (b0-8) shown below can also be used.

Furthermore, onium salts in which the anion moiety of these onium salts has been replaced by an anion moiety represented by any one of formulas (b1) to (b8) shown below can also be used.

[Chemical Formula 70]

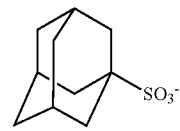

(b0-1)

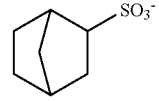

(b0-2)

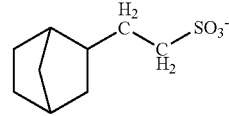

(b0-3)

-continued (b0-4)
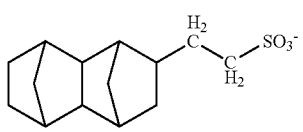

(b0-5)
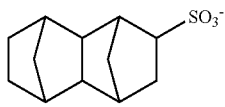

(b0-6)
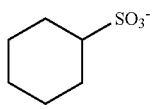

(b0-7)
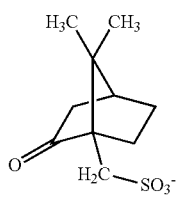

(b0-8)
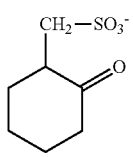

[Chemical Formula 71]

(b1)
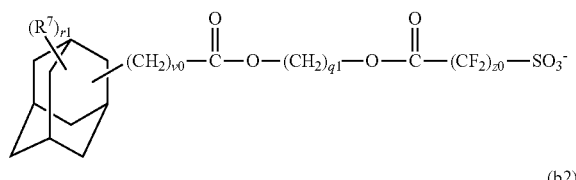

(b2)
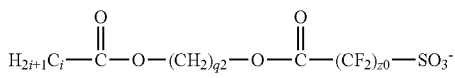

(b3)
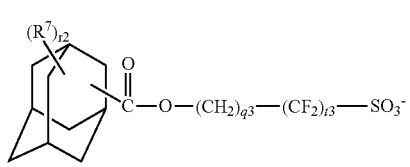

(b4)
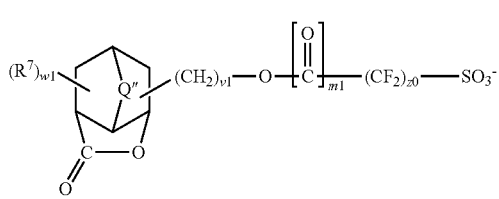

(b5)
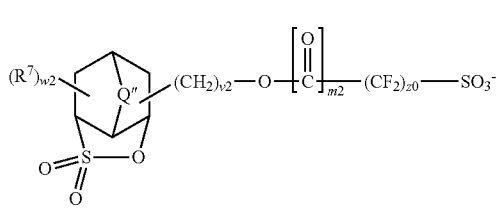

-continued (b6)
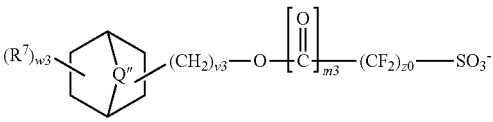

(b7)
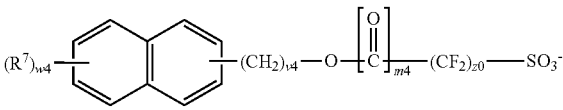

(b8)
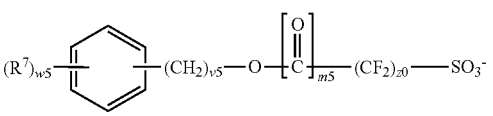

In the formulas, each z0 independently represents an integer of 1 to 3, each of q1 and q2 independently represents an integer of 1 to 5, q3 represents an integer of 1 to 12, t3 represents an integer of 1 to 3, each of r1 and r2 independently represents an integer of 0 to 3, i represents an integer of 1 to 20, $R^7$ represents a substituent, each of m1 to m5 independently represents 0 or 1, each of v0 to v5 independently represents an integer of 0 to 3, each of w1 to w5 independently represents an integer of 0 to 3, and Q" is the same as defined above.

Examples of the substituent for $R^7$ include the same groups as those which the aforementioned aliphatic hydrocarbon group or aromatic hydrocarbon group for X may have as a substituent.

If there are two or more of the $R^7$ group, as indicated by the values r1 and r2, and w1 to w5, then the two or more of the $R^7$ groups may be the same or different from each other.

Of the above possibilities for the onium salt acid generator, the $R^{4\prime\prime}$ group in the above general formula (b-1) or (b-2) is preferably an alkyl group which may have a substituent, and of such acid generators, those represented by general formula (b1-1-20) shown below are particularly desirable because they produce particularly favorable effects for the present invention.

[Chemical Formula 72]

(b1-1-20)
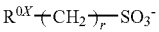

In formula (b1-1-20), $R^{OX}$ represents a cyclic alkyl group of 4 to 12 carbon atoms which contains an oxygen atom (=O) as a substituent, and r represents either 0 or 1.

In general formula (b1-1-20), $R^{OX}$ represents a cyclic alkyl group of 4 to 12 carbon atoms which contains an oxygen atom (=O) as a substituent.

The expression "contains an oxygen atom (=O) as a substituent" means that two hydrogen atoms bonded to one carbon atom that constitutes part of the cyclic alkyl group of 4 to 12 carbon atoms have been substituted with an oxygen atom (=O).

There are no particular limitations on the cyclic alkyl group for $R^{OX}$, provided it contains 4 to 12 carbon atoms, and the group may be either monocyclic or polycyclic. Examples include groups in which one hydrogen atom has been removed from a monocycloalkane or a polycycloalkane such as a bicycloalkane, tricycloalkane or tetracycloalkane. As the monocycle group, groups in which one hydrogen atom has been removed from a monocycloalkane of 3 to 8 carbon atoms are preferred, and specific examples include a cyclopentyl group, cyclohexyl group, cycloheptyl group or cyclooctyl group. As the polycyclic group, groups of 7 to 12 carbon atoms are preferred, and specific examples include an adamantyl group, norbornyl group, isobornyl group, tricyclodecyl group or tetracyclododecyl group.

As $R^{OX}$, a polycyclic alkyl group of 4 to 12 carbon atoms which contains an oxygen atom (=O) as a substituent is preferable, and from an industrial viewpoint, groups in which two hydrogen atoms bonded to one carbon atom that constitutes a part of an adamantyl group, norbornyl group or tetracyclododecyl group have been substituted with an oxygen atom (=O) are more preferable. A norbornyl group which contains an oxygen atom (=O) as a substituent is particularly desirable.

The $R^{OX}$ group may also have another substituent besides the oxygen atom. Examples of this other substituent include lower alkyl groups of 1 to 5 carbon atoms.

In general formula (b1-1-20), r represents 0 or 1, and is preferably 1.

Specific examples of preferred anions represented by the above general formula (b1-1-20) include anions containing an alicyclic group represented by the above chemical formulas (b0-7) and (b0-8).

Further, onium salt acid generators in which the anion moiety in general formula (b-1) or (b-2) is replaced by an anion moiety represented by general formula (b-3) or (b-4) shown below may also be used. In these acid generators, the cation moiety is the same as that shown in (b-1) or (b-2).

[Chemical Formula 73]

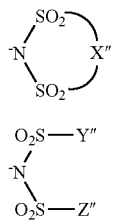

(b-3)

(b-4)

In formulas (b-3) and (b-4) above, X" represents an alkylene group of 2 to 6 carbon atoms in which at least one hydrogen atom has been substituted with a fluorine atom, and each of Y" and Z" independently represents an alkyl group of 1 to 10 carbon atoms in which at least one hydrogen atom has been substituted with a fluorine atom.

X" represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

Each of Y" and Z" independently represents a linear or branched alkyl group in which at least one hydrogen atom has been substituted with a fluorine atom, and the alkyl group has 1 to 10 carbon atoms, preferably 1 to 7 carbon atoms, and most preferably 1 to 3 carbon atoms.

The smaller the number of carbon atoms of the alkylene group for X" or the alkyl group for Y" and Z" within the above-mentioned range of the number of carbon atoms, the more the solubility in a resist solvent is improved, and therefore a smaller number is preferred.

Further, in the alkylene group for X" or the alkyl group for Y" and Z", it is preferable that the number of hydrogen atoms substituted with fluorine atoms is as large as possible, because the acid strength increases and the transparency to high energy radiation of 200 nm or less or electron beam is improved.

The ratio of fluorine atoms within the alkylene group or alkyl group, namely the fluorination ratio, is preferably within a range from 70 to 100%, and more preferably from 90 to 100%. It is particularly desirable that the alkylene group or alkyl group is a perfluoroalkylene group or perfluoroalkyl group in which all of the hydrogen atoms have been substituted with fluorine atoms.

Furthermore, a sulfonium salt having a cation moiety represented by general formula (b-5) or (b-6) shown below may also be used as an onium salt acid generator.

[Chemical Formula 74]

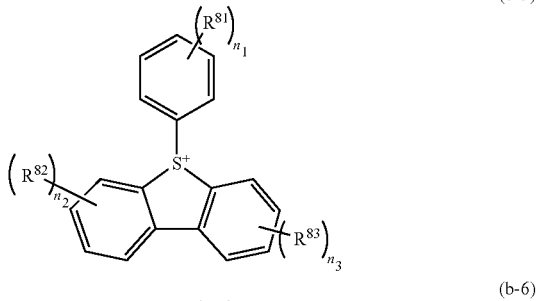

(b-5)

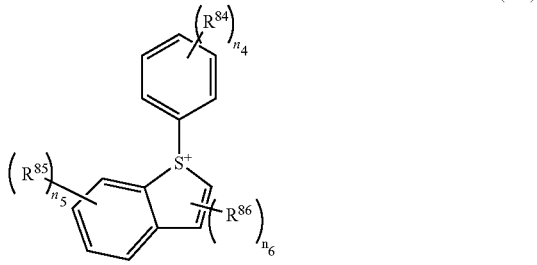

(b-6)

In formulas (b-5) and (b-6) above, each of $R^{81}$ to $R^{86}$ independently represents an alkyl group, acetyl group, alkoxy group, carboxyl group, hydroxyl group or hydroxyalkyl group, each of $n_1$ to $n_5$ independently represents an integer of 0 to 3, and $n_6$ represents an integer of 0 to 2.

With respect to $R^{81}$ to $R^{86}$, the alkyl group is preferably an alkyl group of 1 to 5 carbon atoms, more preferably a linear or branched alkyl group, and most preferably a methyl group, ethyl group, propyl group, isopropyl group, n-butyl group or tert butyl group.

The alkoxy group is preferably an alkoxy group of 1 to 5 carbon atoms, more preferably a linear or branched alkoxy group, and most preferably a methoxy group or ethoxy group.

The hydroxyalkyl group is preferably an aforementioned alkyl group hi which one or more hydrogen atoms have been substituted with hydroxy groups, and examples thereof include a hydroxymethyl group, hydroxyethyl group and hydroxypropyl group.

If there are two or more of an individual $R^{81}$ to $R^{86}$ group, as indicated by the corresponding value of $n_1$ to $n_6$, then the two or more of the individual $R^{81}$ to $R^{86}$ group may be the same or different from each other.

$n_1$ is preferably 0 to 2, more preferably 0 or 1, and still more preferably 0.

It is preferable that $n_2$ and $n_3$ each independently represents 0 or 1, and more preferably 0.

$n_4$ is preferably 0 to 2, and more preferably 0 or 1.

$n_5$ is preferably 0 or 1, and more preferably 0.

$n_6$ is preferably 0 or 1, and more preferably 1.

The anion moiety of the sulfonium salt having a cation moiety represented by general formula (b-5) or (b-6) is not particularly limited, and the same anion moieties as those used within the various onium salt-based acid generators that have been proposed before now may be used. Examples of such anion moieties include fluorinated alkylsulfonate ions such as the anion moieties ($R^{4''}SO_3^-$) for the onium salt acid generators represented by general formula (b-1) or (b-2) shown above, and anion moieties represented by general formula (b-3) or (b-4) shown above.

In the present description, an oxime sulfonate acid generator is a compound having at least one group represented by general formula (B-1) shown below, and has a feature of generating acid upon irradiation (exposure). Such oxime sulfonate acid generators are widely used for chemically amplified resist compositions, and may be selected as appropriate.

[Chemical Formula 75]

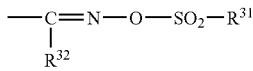

(B-1)

In formula (B-1), each of $R^{31}$ and $R^{32}$ independently represents an organic group.

The organic groups for $R^{31}$ and $R^{32}$ refer to groups containing a carbon atom, which may also include atoms other than carbon atoms (such as a hydrogen atom, oxygen atom, nitrogen atom, sulfur atom or halogen atom (such as a fluorine atom or chlorine atom) or the like).

As the organic group for $R^{31}$, a linear, branched, or cyclic alkyl group or aryl group is preferable. The alkyl group or the aryl group may have a substituent. The substituent is not particularly limited, and examples thereof include a fluorine atom and a linear, branched or cyclic alkyl group having 1 to 6 carbon atoms. The expression that the alkyl group or the aryl group "may have a substituent" means that part or all of the hydrogen atoms of the alkyl group or aryl group may be substituted with a substituent.

The alkyl group preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. A "partially halogenated alkyl group" refers to an alkyl group in which part of the hydrogen atoms are substituted with halogen atoms and the "completely halogenated alkyl group" refers to an alkyl group in which all of the hydrogen atoms are substituted with halogen atoms. Examples of halogen atoms include fluorine atoms, chlorine atoms, bromine atoms and iodine atoms, and fluorine atoms are particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, a partially or completely halogenated aryl group is particularly desirable. A "partially halogenated aryl group" refers to an aryl group in which some of the hydrogen atoms are substituted with halogen atoms and a "completely halogenated aryl group" refers to an aryl group in which all of hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched, or cyclic alkyl group, aryl group, or cyano group is preferable. Examples of the alkyl group and the aryl group for $R^{32}$ include the same alkyl groups and aryl groups as those described above for $R^{31}$.

As $R^{32}$, a cyano group, an alkyl group of 1 to 8 carbon atoms having no substituent or a fluorinated alkyl group of 1 to 8 carbon atoms is particularly desirable.

Preferred examples of the oxime sulfonate acid generator include compounds represented by general formula (B-2) or (B-3) shown below.

[Chemical Formula 76]

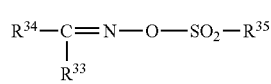

(B-2)

In formula (B-2), $R^{33}$ represents a cyano group, an alkyl group having no substituent or a halogenated alkyl group, $R^{34}$ represents an aryl group, and $R^{35}$ represents an alkyl group having no substituent or a halogenated alkyl group.

[Chemical Formula 77]

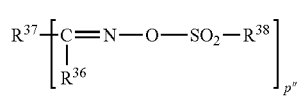

(B-3)

In formula (B-3), $R^{36}$ represents a cyano group, an alkyl group having no substituent or a halogenated alkyl group, $R^{37}$ represents a divalent or trivalent aromatic hydrocarbon group, $R^{38}$ represents an alkyl group having no substituent or a halogenated alkyl group, and p" represents 2 or 3.

In general formula (B-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more fluorinated, and most preferably 90% or more fluorinated.

Examples of the aryl group for $R^{34}$ include groups in which one hydrogen atom has been removed from an aromatic hydrocarbon ring, such as a phenyl group, biphenyl group, fluorenyl group, naphthyl group, anthryl group or phenanthryl group, and heteroaryl groups in which some of the carbon atoms constituting the ring(s) of these groups are substituted with hetero atoms such as an oxygen atom, a sulfur atom or a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group or halogenated alkyl group as the substituent preferably has 1 to 8 carbon atoms, and more preferably 1 to 4 carbon atoms. Further, the halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms fluorinated, more preferably 70% or more fluorinated, still more preferably 90% or more fluorinated. A completely fluorinated alkyl group in which 100% of the hydrogen atoms are substituted with fluorine atoms is particularly desirable.

In general formula (B-3), examples of the alkyl group having no substituent and the halogenated alkyl group for $R^{36}$ include the same groups as those described above for the alkyl group having no substituent and the halogenated alkyl group for $R^{33}$.

Examples of the divalent or trivalent aromatic hydrocarbon group for $R^{37}$ include groups in which one or two hydrogen atoms have been removed from the aforementioned aryl group for $R^{34}$.

Examples of the alkyl group having no substituent or the halogenated alkyl group for $R^{38}$ include the same groups as those exemplified above for the alkyl group having no substituent or the halogenated alkyl group for $R^{35}$.

p" is preferably 2.

Specific examples of suitable oxime sulfonate acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate-based acid generators disclosed in Japanese Unexamined Patent Application, First Publication No. Hei 9-208554 (Chemical Formulas 18 and 19 shown in paragraphs [0012] to [0014]) and oxime sulfonate acid generators disclosed in International Patent Publication 04/074242 pamphlet (Examples 1 to 40 described at pages 65 to 85) may also be used favorably.

Furthermore, the following compounds may also be used as preferred examples.

[Chemical Formula 78]

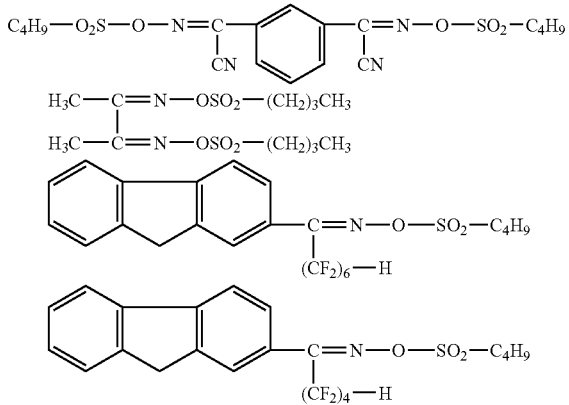

Of the aforementioned diazomethane acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and his(2,4-dimethylphenylsulfonyl)diazomethane.

Further, diazomethane acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may also be used favorably.

Furthermore, examples of poly(bis-sulfonyl)diazomethanes include those disclosed in Japanese Unexamined Patent Application, First Publication No. Hei 11-322707, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane and 1,10-bis(cyclohexylsulfonyldiazomethylsulfonyl)decane.

As the component (B), one type of acid generator described above may be used alone, or two or more types of acid generators may be used in combination.

In the present invention, as the component (B), it is preferable to use an acid generator that generates an acid containing a —$SO_3^-$ moiety upon exposure, and the use of at least one acid generator selected from the group consisting of oxime sulfonate acid generators and onium salt acid generators in which the carbon atom adjacent to the sulfur atom of the —$SO_3^-$ moiety has no fluorine atoms bonded thereto is particularly desirable.

In the positive resist composition of the present invention, by combining this type of acid with the component (A1), the effects of the present invention can be further enhanced.

In the positive resist composition of the present invention, the amount of the component (B) relative to 100 parts by weight of the component (A) is preferably within a range from 0.5 to 50 parts by weight, and more preferably 1 to 40 parts by weight. By ensuring that the amount of the component (B) is within the above-mentioned range, formation of a resist pattern can be performed satisfactorily. Further, by virtue of the above-mentioned range, a uniform solution can be obtained and the storage stability tends to improve.

<Component (D)>

The positive resist composition of the present invention may further contain a nitrogen-containing organic compound (D) (hereafter referred to as "component (D)") as an optional component.

There are no particular limitations on the component (D) as long as it functions as an acid diffusion control agent, namely, a quencher which traps the acid generated from the component (B) upon exposure. A multitude of these components (D) have already been proposed, and any of these known compounds may be used, although an aliphatic amine, and particularly a secondary aliphatic amine or tertiary aliphatic amine is preferable.

An "aliphatic amine" is an amine having one or more aliphatic groups, wherein the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of not more than 12 carbon atoms (namely, alkylamines or alkyl alcohol amines), and cyclic amines.

Specific examples of alkylamines and alkyl alcohol amines include monoalkylamines such as n-hexylamine, n-heptylamine, n-octylamine, n-nonylamine and n-decylamine, dialkylamines such as diethylamine, di-n-propylamine, di-n-heptylamine, di-n-octylamine and dicyclohexylamine, trialkylamines such as trimethylamine, triethylamine, tri-n-propylamine, tri-n-butylamine, tri-n-pentylamine, tri-n-hexylamine, tri-n-heptylamine, tri-n-octylamine, tri-n-nonylamine, tri-n-decylamine and tri-n-dodecylamine, and alkyl alcohol amines such as diethanolamine, triethanolamine, diisopropanolamine, triisopropanolamine, di-n-octanolamine and tri-n-octanolamine. Among these, trialkylamines of 5 to 10 carbon atoms are preferable, and tri-n-octylamine is particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine and 1,4-diazabicyclo[2.2.2]octane.

As the component (D), one compound may be used alone, or two or more different compounds may be used in combination.

The component (D) is typically used in an amount within a range from 0.01 to 5.0 parts by weight, relative to 100 parts by weight of the component (A). By ensuring that the amount of the component (D) is within the above-mentioned range, the shape of the resist pattern and the post exposure stability of the latent image formed by the pattern-wise exposure of the resist layer are improved.

<Optional Components>

[Component (E)]

Furthermore, in the positive resist composition of the present invention, in order to prevent any deterioration in sensitivity and improve the resist pattern shape and the post exposure stability of the latent image formed by the pattern-wise exposure of the resist layer, at least one compound (E) (hereafter referred to as "component (E)") selected from the group consisting of organic carboxylic acids, phosphorus oxo acids and derivatives thereof may be added.

Examples of the organic carboxylic acids include acetic acid, malonic acid, citric acid, malic acid, succinic acid, benzoic acid and salicylic acid.

Examples of the phosphorus oxo acids include phosphoric acid, phosphonic acid and phosphinic acid. Among these, phosphonic acid is particularly desirable.

Examples of the phosphorus oxo acid derivatives include esters in which a hydrogen atom within an above-mentioned oxo acid is substituted with a hydrocarbon group. Examples of the hydrocarbon group include alkyl groups of 1 to 5 carbon atoms and aryl groups of 6 to 15 carbon atoms.

Examples of phosphoric acid derivatives include phosphate esters such as di-n-butyl phosphate and diphenyl phosphate.

Examples of phosphonic acid derivatives include phosphonate esters such as dimethyl phosphonate, di-n-butyl phosphonate, diphenyl phosphonate and dibenzyl phosphonate, as well as phenylphosphonic acid.

Examples of phosphinic acid derivatives include phosphinate esters and phenylphosphinic acid.

As the component (E), one type of compound may be used alone, or two or more types of compounds may be used in combination.

The component (E) is preferably an organic carboxylic acid, and is more preferably salicylic acid.

The component (E) is typically used in an amount within a range from 0.01 to 5.0 parts by weight per 100 parts by weight of the component (A).

If desired, other miscible additives can also be added to the positive resist composition of the present invention. Examples of such miscible additives include additive resins for improving the performance of the resist film, surfactants for improving the applicability, dissolution inhibitors, plasticizers, stabilizers, colorants, halation prevention agents, and dyes.

[Component (S)]

The positive resist composition of the present invention can be prepared by dissolving the materials for the resist composition in an organic solvent (hereafter, frequently referred to as "component (S)").

The component (S) may be any organic solvent which can dissolve the respective components to give a uniform solution, and one or more kinds of organic solvent can be appropriately selected from those which have been conventionally known as solvents for chemically amplified resists.

Specific examples of the organic solvent include lactones such as γ-butyrolactone; ketones such as acetone, methyl ethyl ketone, cyclohexanone, methyl-n-pentyl ketone, methyl isopentyl ketone and 2-heptanone; polyhydric alcohols, such as ethylene glycol, diethylene glycol, propylene glycol and dipropylene glycol; polyhydric alcohol derivatives, including compounds having an ester bond such as ethylene glycol monoacetate, diethylene glycol monoacetate, propylene glycol monoacetate and dipropylene glycol monoacetate, and compounds having an ether bond such as a monoalkyl ether (such as a monomethyl ether, monoethyl ether, monopropyl ether or monobutyl ether) or a monophenyl ether of any of the above polyhydric alcohols or compounds having an ester bond [among these derivatives, propylene glycol monomethyl ether acetate (PGMEA) and propylene glycol monomethyl ether (PGME) are preferred]; cyclic ethers such as dioxane; esters such as methyl lactate, ethyl lactate (EL), methyl acetate, ethyl acetate, butyl acetate, methyl pyruvate, ethyl pyruvate, methyl methoxypropionate and ethyl ethoxypropionate; and aromatic organic solvents such as anisole, ethyl benzyl ether, cresyl methyl ether, diphenyl ether, dibenzyl ether, phenetole, butyl phenyl ether, ethylbenzene, diethylbenzene, pentylbenzene, isopropylbenzene, toluene, xylene, cymene and mesitylene.

These organic solvents may be used individually, or as mixed solvents containing two or more solvents.

Among these, PGMEA, PGME and EL are preferable.

Further, a mixed solvent obtained by mixing PGMEA with a polar solvent is also preferable. The mixing ratio (weight ratio) of this mixed solvent can be determined appropriately with due consideration of the compatibility of the PGMEA with the polar solvent, but is preferably in the range of 1:9 to 9:1, and more preferably from 2:8 to 8:2.

Specifically, when EL is mixed as the polar solvent, the PGMEA:EL weight ratio is preferably from 1:9 to 9:1, and more preferably from 2:8 to 8:2. Alternatively, when PGME is mixed as the polar solvent, the ratio of PGMEA:PGME is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably within a range from 70:30 to 95:5.

The amount of the organic solvent is not particularly limited, and may be adjusted appropriately to a concentration which enables coating of a coating solution to a substrate in accordance with the thickness of the coating film. In general, the organic solvent is used in an amount that yields a solid content for the resist composition that is within a range from 0.5 to 20% by weight, and preferably from 1 to 15% by weight.

Dissolving of the resist materials in the component (S) can be conducted, for example, by simply mixing and stirring each of the above components using a conventional method. Where required, the composition may also be mixed and dispersed using a dispersion device such as a dissolver, a homogenizer, or a triple roll mill. Furthermore, following mixing, the composition may also be filtered using a mesh or a membrane filter or the like.

The positive resist composition of the present invention described above has the effect of enabling the formation of a resist pattern that exhibits excellent resolution and a superior shape, with reduced line width roughness (LWR). It is thought that the reasons that this effect is obtained are as follows.

Namely, the polymeric compound (A1) in the present invention has a structural unit (a0) containing an "acid-dissociable, dissolution-inhibiting group having a 1,3-dioxole skeleton". Because this acid-dissociable, dissolution-inhibiting group has a 1,3-dioxole skeleton, it can be more readily dissociated by the acid generated from the component (B) upon exposure, meaning the dissociation efficiency of the acid-dissociable, dissolution-inhibiting group improves. As a result, it is thought that the difference in solubility within the alkali developing solution of the unexposed portions and the exposed portions (namely, the solubility contrast) is greater than that observed for conventional positive resist compositions, resulting in an improvement in the resolution.

Further, during resist pattern formation, it is thought that the action of the acid generated from the component (B) upon exposure causes cleavage of the bonds that constitute the 1,3-dioxole skeleton, which enhances the hydrophilicity and increases the solubility within the alkali developing solution, enabling the formation of a resist pattern of superior shape, with reduced LWR.

Furthermore, during resist pattern formation, the positive resist composition of the present invention tends to yield a higher sensitivity than that conventionally achievable. In addition, another effect provided by the positive resist composition of the present invention is suppression of the generation of outgas. As a result, contamination of the exposure apparatus and the like is reduced. Accordingly, the positive resist composition of the present invention is ideal as a resist for use with EB and EUV. Furthermore, the positive resist composition can also be used favorably with a KrF excimer laser.

<<Method of Forming a Resist Pattern>>

The method of forming a resist pattern according to the second aspect of the present invention includes: applying a positive resist composition of the present invention to a substrate to form a resist film on the substrate, conducting exposure of the resist film, and alkali developing the resist film to form a resist pattern.

The method of forming a resist pattern according to the present invention can be performed, for example, as follows.

Firstly, the aforementioned positive resist composition according to the present invention is applied onto a substrate using a spinner or the like, and a prebake (post applied bake (PAB)) is conducted under temperature conditions of 80 to 150° C. for 40 to 120 seconds, and preferably 60 to 90 seconds, to form a resist film. Following selective exposure of the thus formed resist film, either by exposure through a mask pattern using an exposure apparatus such as an ArF exposure apparatus, an electron beam lithography apparatus or an EUV exposure apparatus, or by patterning via direct irradiation with an electron beam without using a mask pattern, PEB (post exposure baking) is conducted under temperature conditions of 80 to 150° C. for 40 to 120 seconds, and preferably 60 to 90 seconds. Subsequently, a developing treatment is conducted using an alkali developing solution such as a 0.1 to 10% by weight aqueous solution of tetramethylammonium hydroxide (TMAH), preferably followed by rinsing with pure water, and drying. If desired, a bake treatment (post bake) may be conducted following the above developing treatment. In this manner, a resist pattern that is faithful to the mask pattern can be obtained.

The substrate is not specifically limited, and conventionally known substrates can be used. For example, substrates for electronic components, and such substrates having predetermined wiring patterns formed thereon can be used. Specific examples of the substrate include substrates made from metals such as silicon wafer, copper, chromium, iron and aluminum, as well as glass substrates. Suitable materials for the wiring pattern include copper, aluminum, nickel, and gold.

Further, as the substrate, any one of the above-mentioned substrates provided with an inorganic and/or organic film on the surface thereof may also be used. As the inorganic film, an inorganic antireflection film (inorganic BARC) may be used. As the organic film, an organic antireflection film (organic BARC) or an organic film such as the lower-layer organic film used in a multilayer resist method may be used.

Here, a "multilayer resist method" is a method in which at least one layer of an organic film (a lower-layer organic film) and at least one layer of a resist film (an upper resist film) are provided on a substrate, and a resist pattern formed within the upper resist film is used as a mask to conduct patterning of the lower-layer organic film. This method is capable of forming a pattern with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed.

The multilayer resist method can be broadly classified into a method in which a double-layer structure consisting of an upper-layer resist film and a lower-layer organic film is formed (a double-layer resist method), and a method in which a multilayer structure having at least three layers consisting of an upper-layer resist film, a lower-layer organic film and at least one intermediate layer (a thin metal film or the like) provided between the upper-layer resist film and the lower-layer organic film is formed (a three-layer resist method).

The wavelength to be used for exposure is not particularly limited and the exposure can be conducted using radiation such as an ArF excimer laser, KrF excimer laser, $F_2$ excimer laser, extreme ultraviolet rays (EUV), vacuum ultraviolet rays (VUV), electron beam (EB), X-rays, and soft X-rays. The resist composition of the present invention described above is effective for use with a KrF excimer laser, ArF excimer laser, EB and EUV, and is particularly effective to ArF excimer laser.

The exposure of the resist film can be either a general exposure (dry exposure) conducted in air or an inert gas such as nitrogen, or an immersion exposure (liquid immersion lithography).

In liquid immersion lithography, the region between the resist film and the lens at the lowermost point of the exposure apparatus is pre-filled with a solvent (an immersion medium) that has a larger refractive index than the refractive index of air, and the exposure (immersion exposure) is conducted in this state.

The immersion medium preferably exhibits a refractive index larger than the refractive index of air but smaller than the refractive index of the resist film to be exposed. The refractive index of the immersion medium is not particularly limited as long at it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, wherein the boiling point of the fluorine-based inert liquid is preferably within a range from 70 to 180° C., and more preferably from 80 to 160° C. A fluorine-based inert liquid having a boiling point within the above-mentioned range is advantageous in that the removal of the immersion medium after the exposure can be conducted by a simple method.

As the fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkyl amine compounds.

Specifically, one example of a suitable perfluoroalkyl ether compound is perfluoro(2-butyl-tetrahydrofuran) (boiling point: 102° C.), and an example of a suitable perfluoroalkyl amine compound is perfluorotributylamine (boiling point: 174° C.).

As the immersion medium, water is preferable in terms of cost, safety, environment and versatility.

Moreover, the method of forming a resist pattern according to the present invention can also be applied to double exposure methods and double patterning methods.

<<Polymeric Compound>>

The polymeric compound according to the third aspect of the present invention has a structural unit represented by general formula (a0-1') shown below.

[Chemical Formula 79]

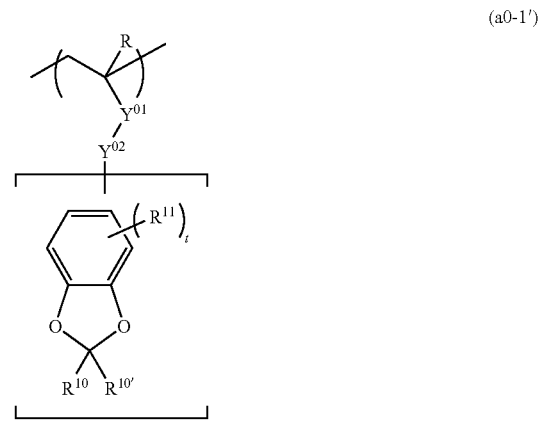

(a0-1')

In formula (a0-1'), R represents a hydrogen atom, an alkyl group of 1 to 5 carbon atoms or a halogenated alkyl group of 1 to 5 carbon atoms, $Y^{01}$ represents a divalent organic group that becomes an alkali-soluble group upon cleavage of the bond to $Y^{02}$ under the action of acid, $Y^{02}$ represents a single bond or a divalent linking group, which substitutes one of the hydrogen atoms of the group within the brackets [ ] of formula (a0-1') that is derived from either a 1,3-benzodioxole or a derivative thereof, $R^{11}$ represents a hydrocarbon group of 1 to 30 carbon atoms which may have a substituent, t represents an integer of 0 to 3, and in those cases where t is 2 or 3, a plurality of $R^{11}$ groups may be bonded together to form a ring, or may be bonded to the benzene ring to form an aromatic ring, $R^{10}$ represents a hydrogen atom or an alkyl group of 1 to 5 carbon atoms which may have a substituent, $R^{10'}$ represents a hydrogen atom or an alkyl group of 1 to 5 carbon atoms which may have a substituent, and $R^{10}$ and $R^{10'}$ may be bonded together to form a ring.

In the polymeric compound of the present invention, $Y^{02}$ within the general formula (a0-1') is preferably a divalent linking group containing a group represented by general formula (p11') shown below.

[Chemical Formula 80]

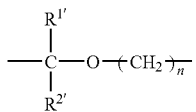

(p11')

In formula (p11'), each of $R^{1\prime}$ and $R^{2\prime}$ independently represents a hydrogen atom or an alkyl group of 1 to 5 carbon atoms, and n represents an integer of 0 to 3.

Further, in addition to the above structural unit (a0), the polymeric compound of the present invention preferably also includes a structural unit (a5) derived from a hydroxystyrene.

The structural unit (a5) is preferably a structural unit represented by general formula (a5-1) shown below.

[Chemical Formula 81]

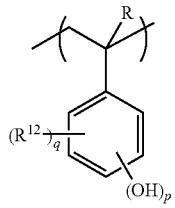

(a5-1)

In formula (a5-1), R represents a hydrogen atom, an alkyl group of 1 to 5 carbon atoms or a halogenated alkyl group of 1 to 5 carbon atoms, $R^{12}$ represents a halogen atom, an alkyl group of 1 to 5 carbon atoms or a halogenated alkyl group of 1 to 5 carbon atoms, p represents an integer of 1 to 3, and q represents an integer of 0 to 4, provided that p+q is an integer of 1 to 5.

The polymeric compound of the present invention described above is the same as the component (A1) of the above-described positive resist composition of the present invention.

Descriptions relating to the general formulas (a0-1'), (p11') and (a5-1) are the same as the descriptions for the general formulas (a0-1'), (p11') and (a5-1) presented above in relation to the positive resist composition of the present invention.

The polymeric compound of the present invention can be produced, for example, by using conventional methods to react a polyhydroxystyrene with a vinyl ether compound containing a "1,3-dioxole skeleton" structure in the presence of an acid.

The structure of the thus obtained polymeric compound can be confirmed by general organic analysis methods such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elemental analysis and X-ray diffraction analysis (this also applies to the structure of the compound described below).

By using the polymeric compound of the present invention as the base component (A) within a positive resist composition containing a base component (A) and an acid generator component (B), a resist pattern can be formed that exhibits excellent resolution and a superior shape, with reduced line width roughness (LWR).

<<Compound>>

The compound according to the fourth aspect of the present invention is a compound represented by general formula (a0-1-1) shown below.

[Chemical Formula 82]

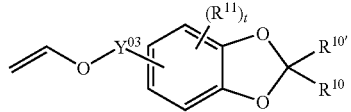

(a0-1-1)

In formula (a0-1-1), $Y^{03}$ represents a single bond or a divalent linking group, $R^{11}$ represents a hydrocarbon group of 1 to 30 carbon atoms which may have a substituent, t represents an integer of 0 to 3, and in those cases where t is 2 or 3, a plurality of $R^{11}$ groups may be bonded together to form a ring, or may be bonded to the benzene ring to form an aromatic ring, $R^{10}$ represents a hydrogen atom or an alkyl group of 1 to 5 carbon atoms which may have a substituent, $R^{10\prime}$ represents a hydrogen atom or an alkyl group of 1 to 5 carbon atoms which may have a substituent, and $R^{10}$ and $R^{10\prime}$ may be bonded together to form a ring.

$R^{11}$, t, $R^{10}$ and $R^{10\prime}$ in general formula (a0-1-1) are the same as defined above for $R^{11}$, t, $R^{10}$ and $R^{10\prime}$ in general formula (a0-1') within the description for the positive resist composition of the present invention.

$Y^{03}$ represents a single bond or a divalent linking group, and examples include the same groups as those described above for $Q^0$ in the general formula (p11) described in relation to the positive resist composition of the present invention.

Specific examples of the compound according to the fourth aspect of the present invention are shown below.

[Chemical Formula 83]

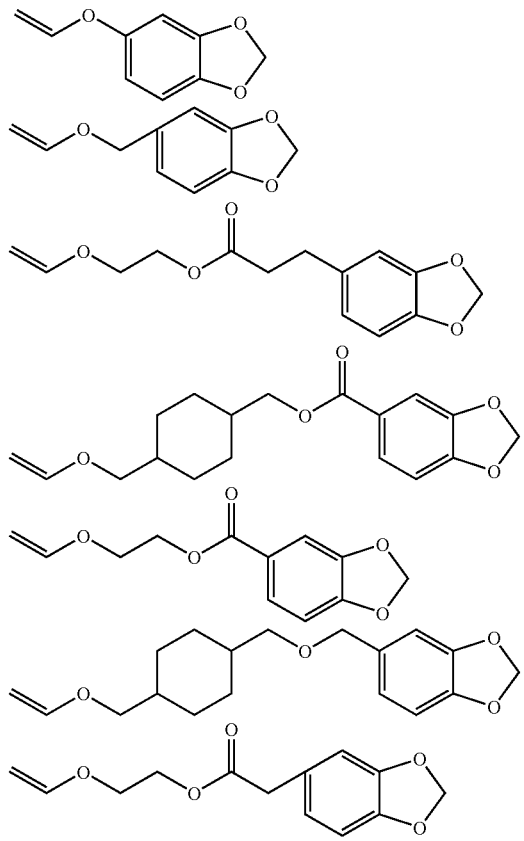

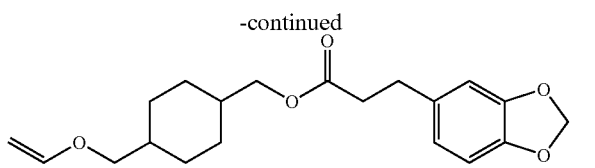

The compound of the fourth aspect of the present invention can be synthesized, for example, by a method in which an alcohol compound containing a "1,3-dioxole skeleton" structure is reacted with 1-bromo-2-chloroethane in the presence of a strong base, and the resultant is then reacted with a metal alkoxide such as potassium butoxide.

The compound according to the fourth aspect of the present invention is a material that is useful for substituting the hydrogen atom of an alkali-soluble group (namely, for protecting the alkali-soluble group), for example during formation of a resin component for a resist. By using the thus obtained resist resin component as the base component (A) of a positive resist composition, a resist pattern can be formed that exhibits excellent resolution and a superior shape, with reduced line width roughness (LWR).

The compound according to the fifth aspect of the present invention is a compound represented by general formula (a0-1-1-1) shown below.

[Chemical Formula 84]

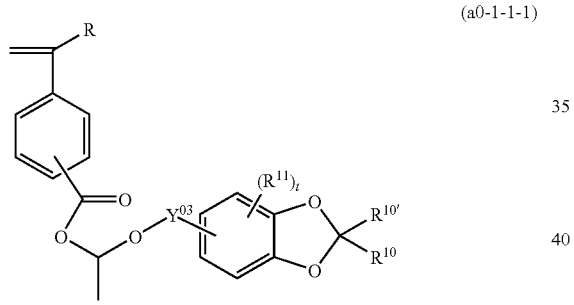

(a0-1-1-1)

In formula (a0-1-1-1), R represents a hydrogen atom, an alkyl group of 1 to 5 carbon atoms or a halogenated alkyl group of 1 to 5 carbon atoms, $Y^{03}$ represents a single bond or a divalent linking group, $R^{11}$ represents a hydrocarbon group of 1 to 30 carbon atoms which may have a substituent, t represents an integer of 0 to 3, and in those cases where t is 2 or 3, a plurality of $R^{11}$ groups may be bonded together to form a ring, or may be bonded to the benzene ring to form an aromatic ring, $R^{10}$ represents a hydrogen atom or an alkyl group of 1 to 5 carbon atoms which may have a substituent, $R^{10'}$ represents a hydrogen atom or an alkyl group of 1 to 5 carbon atoms which may have a substituent, and $R^{10}$ and $R^{10'}$ may be bonded together to form a ring.

In formula (a0-1-1-1), R is the same as defined above, and is preferably a hydrogen atom or a methyl group.

In formula (a0-1-1-1), $Y^{03}$, $R^{11}$, t, $R^{10}$ and $R^{10'}$ are the same as defined above for $Y^{03}$, $R^{11}$, t, $R^{10}$ and $R^{10'}$ in general formula (a0-1-1).

Specific examples of the compound according to the fifth aspect of the present invention are shown below.

In each of the following formulas, $R^{\alpha}$ represents a hydrogen atom, a methyl group or a trifluoromethyl group.

[Chemical Formula 85]

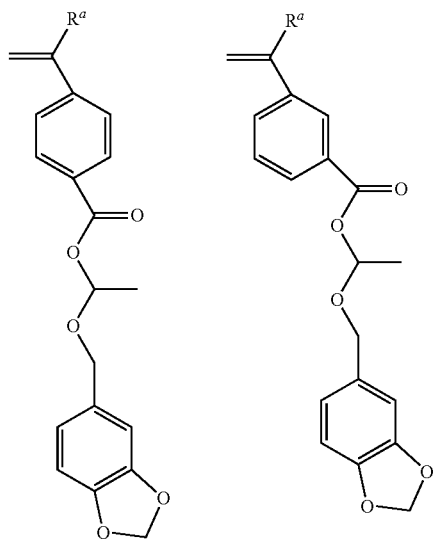

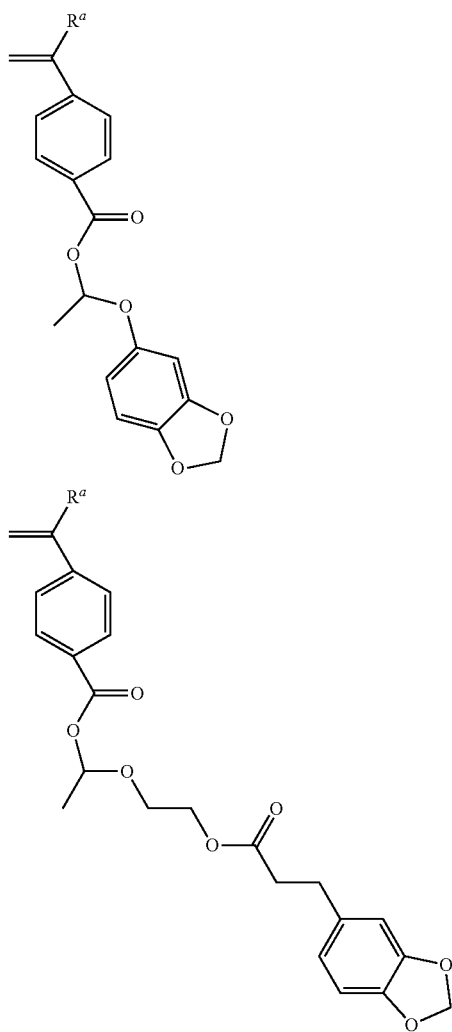

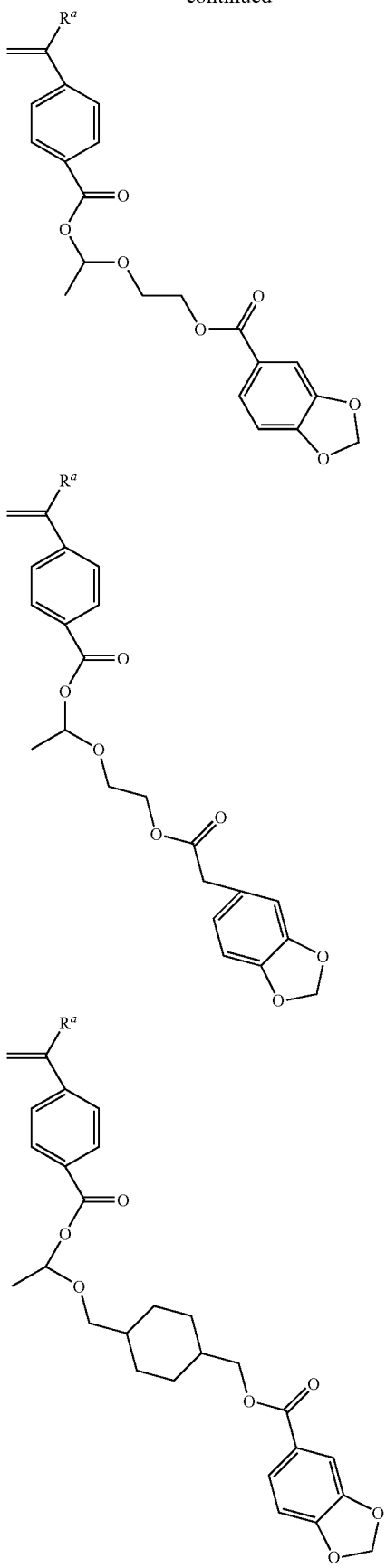
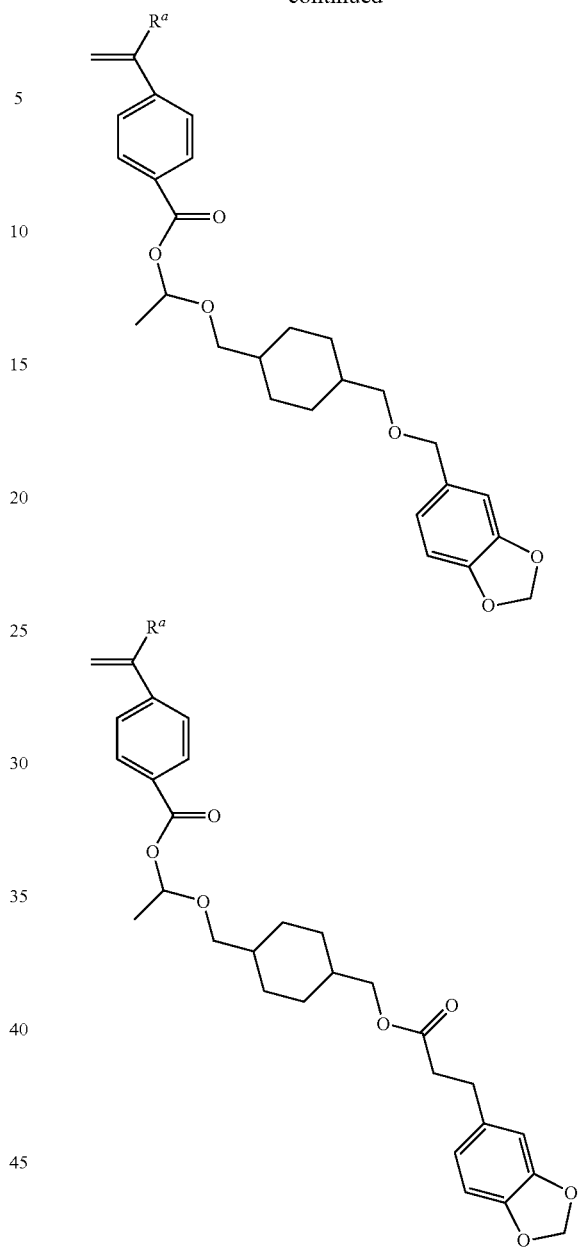

The compound according to the fifth aspect of the present invention can be synthesized, for example, by a method in which a vinylbenzoic acid is reacted with a vinyl ether compound containing a "1,3-dioxole skeleton" structure, in the presence of a strong acid such as trifluoroacetic acid. Besides trifluoroacetic acid, a compound such as pyridinium p-toluenesulfonate may also be used as the acid catalyst.

The compound according to the fifth aspect of the present invention is a material that is useful as a monomer that yields a structural unit of the polymeric compound (A1) that is used within the aforementioned positive resist composition of the present invention.

EXAMPLES

A more detailed description of the present invention is presented below based on a series of examples, although the scope of the present invention is in no way limited by these examples.

<Base Component (A)>

In these examples, the polymeric compound used as the component (A) was synthesized using the method outlined in the following synthesis examples.

Synthesis Example 1

Synthesis of Polymeric Compound (A3-1)

Poly(p-hydroxystyrene) and adamantyl vinyl ether were reacted together in the presence of an acid catalyst using a conventional method, thus yielding a polymeric compound (A3-1).

The structure of the polymeric compound (A3-1) is shown below.

Analysis of the acetal introduction rate within the polymeric compound (A3-1) using $^1$H-NMR revealed a ratio of the number of acetal-type acid-dissociable, dissolution-inhibiting groups represented by the above formula (VII-a-1), relative to the number of p-hydroxystyrene hydroxyl groups of 35%. This result confirmed that the acetal introduction rate (the hydroxyl group protection rate) was 30 mol %.

Further, the weight average molecular weight (Mw) for the polymeric compound (A3-1), measured by GPC and referenced against standard polystyrenes, was 13,000, and the dispersity (Mw/Mn) was 1.3.

The subscript shown at the bottom right of each structural unit within the following chemical formula represents the proportion (mol %) of that structural unit within the polymeric compound.

[Chemical Formula 86]

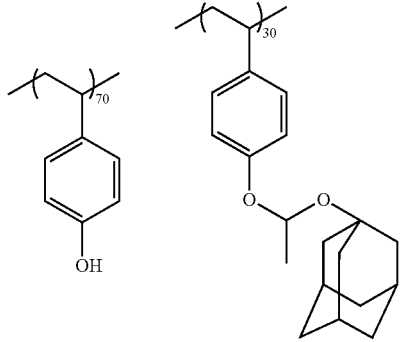

Polymeric compound (A3-1)

Example 1

Synthesis Example 2

Synthesis of Compound (3)

Under a nitrogen atmosphere, a three-necked flask was charged with a compound (1) shown below (50.00 g) and anhydrous THF (250.00 g), and the resulting solution was cooled to 5° C. or lower. NaH (13.15 g, purity: approximately 60% by weight) was added to the flask, and the resulting mixture was stirred for 5 minutes at a temperature of 5° C. or lower. Subsequently, 1-bromo-2-chloroethane (94.25 g) was added. Following stirring for 10 minutes at 5° C. or lower, the temperature was gradually raised, and the reaction mixture was stirred for 24 hours at room temperature. Subsequently, t-butyl methyl ether (250.00 g) was added to the reaction mixture, and the organic layer was washed 3 times with 175 g samples of pure water. The reaction solution was subsequently concentrated and dried, and was then purified by column chromatography (silica gel), yielding 21.15 g of a compound (2).

The results of analyzing the obtained compound (2) by NMR are listed below.

$^1$H-NMR (DMSO-$d_6$, 400 MHz): δ (ppm)=6.79 to 6.86 (m, ArH, 3H), 6.00 (s, ArCH$_2$, 2H), 4.65 (s, OCH$_2$O, 2H), 4.34 to 4.56 (t, OCH$_2$, 2H), 3.59 to 3.81 (t, CH$_2$Cl, 2H).

Based on the above results, it was confirmed that the obtained compound had the structure shown below.

[Chemical Formula 87]

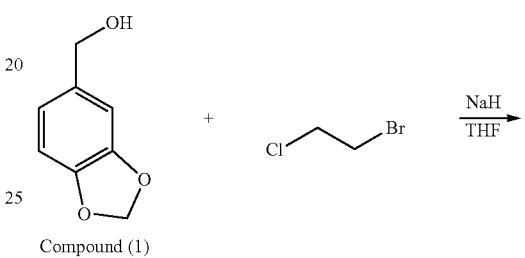

Compound (1)

Compound (2)

Next, under an atmosphere of nitrogen, a three-necked flask was charged with the compound (2) (20.00 g) and anhydrous diethyl ether (200.00 g), and the resulting solution was cooled to 5° C. or lower. Potassium t-butoxide (12.55 g) was then added gradually to the flask over a period of one hour, with the temperature maintained at 5° C. or lower. The resulting reaction mixture was stirred for 30 minutes, and the solid that was produced was removed by filtration. The filtrate was subsequently concentrated and dried, and was then purified by column chromatography (silica gel), yielding 4.15 g of a compound (3).

The results of analyzing the obtained compound (3) by NMR are listed below.

$^1$H-NMR (DMSO-$d_6$, 400 MHz): δ (ppm)=6.80 to 6.87 (m, ArH, 3H), 6.54 (dd, CH, 1H), 6.00 (s, ArCH$_2$, 2H), 4.67 (s, OCH$_2$O, 2H), 4.29 (d, CH, 1H), 4.01 (d, CH, 1H).

Based on the above results, it was confirmed that the obtained compound had the structure shown below.

[Chemical Formula 88]

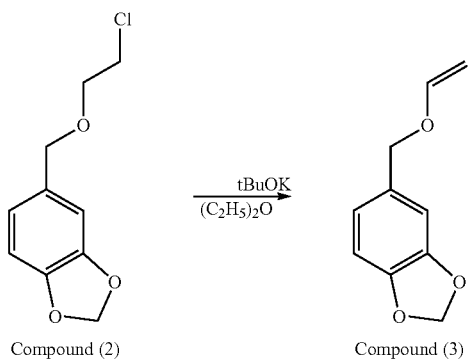

Compound (2)    Compound (3)

[Chemical Formula 89]

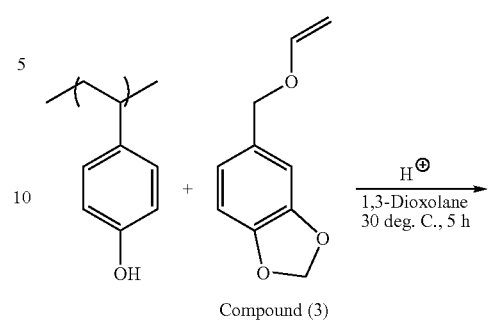

Example 2

Synthesis Example 3

Synthesis of Polymeric Compound (A1-11-1)

Under a nitrogen atmosphere, a three-necked flask was charged with polyhydroxystyrene (24.3 g) and 1,3-dioxolane (90.8 g), and the mixture was stirred to form a solution. The solution was cooled to 10° C., trifluoroacetic acid (0.17 g) was added, and then a 25% by weight dioxolane solution of the compound (3) (11.7 g) was added dropwise to the flask. Following completion of the dropwise addition, the reaction mixture was reacted for 5 hours at 30° C., and then 1% by weight ammonia water (5.2 g) was added and the mixture was stirred for 10 minutes at room temperature. The resulting reaction solution was added dropwise to pure water (2,000 g), and the resulting powder was filtered and then dried under vacuum, yielding 35.1 g of a polymeric compound (A1-11-1).

The acetal introduction rate in this polymeric compound (A1-11-1) was calculated from the integral ratio between the methine carbon (a) of the acetal portion and the aromatic carbon (b) within the $^{13}$C-NMR spectrum. The result revealed an acetal introduction rate of 30.97 mol %.

Further, the weight average molecular weight (Mw) for the polymeric compound (A1-11-1), measured by GPC and referenced against standard polystyrenes, was 10,700, and the dispersity (Mw/Mn) was 1.09.

The results of analyzing the obtained polymeric compound (A1-11-1) by NMR are listed below.

$^1$H-NMR (Acetone-d$_6$, 400 MHz): δ (ppm)=7.95 (br s, OH), 6.71 (br, ArH), 5.91 (br s, ArCH$_2$), 5.42 (br s, acetal H), 4.63 (br s, OCH$_2$O), 4.45 (br s, OCH$_2$O), 1.01 to 2.06 (br m, CH$_3$+CH of main chain).

Based on the above results, it was confirmed that the obtained compound had the structure shown below. The subscript shown at the bottom right of each structural unit within the following chemical formula represents the proportion (mol %) of that structural unit within the polymeric compound.

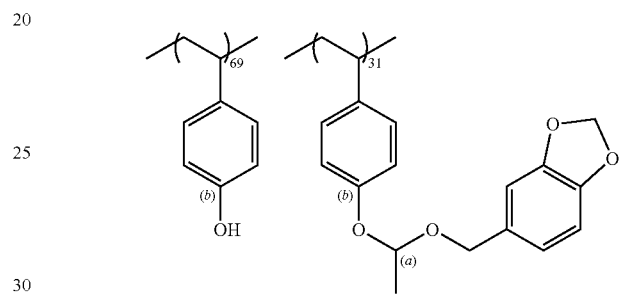

Polymeric compound (A1-11-1)

Example 3

Synthesis Example 4

Synthesis of Compound (4)

4-vinylbenzoic acid (4.7 g) was dissolved in 1,3-dioxolane (23.7 g), the solution was cooled, and then trifluoroacetic acid (0.17 g) was added. Subsequently, a 25% by weight dioxolane solution of the compound (3) (5.65 g) was added dropwise to the flask. Following completion of the dropwise addition, the reaction mixture was reacted for 5 hours at 30° C., and then 1% by weight ammonia water (5.2 g) was added and the mixture was stirred for 10 minutes at room temperature. The reaction solution was fractionated by silica gel chromatography, yielding the target compound (4).

The results of analyzing the obtained compound (4) by NMR are listed below.

$^1$H-NMR (DMSO-d$_6$, 400 MHz): δ (ppm)=8.05 (d, 2H, ArH), 7.45 (d, 2H, ArH), 6.80 to 6.82 (m, ArH, 3H), 6.76 (t, 1H, CH=C), 5.95 (s, ArCH$_2$, 2H), 5.87 (d, 1H, CH=C), 5.49 (q, 1H, acetal-CH), 5.36 (d, 1H, CH=C), 4.65 (s, 2H, OCH$_2$O), 1.61 (d, 3H, CH$_3$).

Based on the above results, it was confirmed that the obtained compound had the structure shown below.

[Chemical Formual 90]

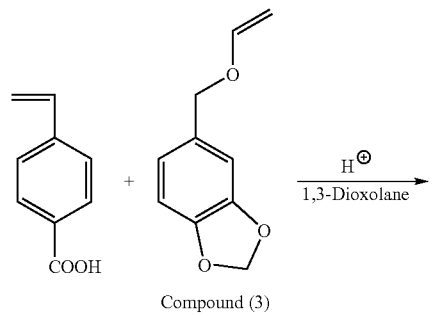

Compound (3)

<Preparation of Positive Resist Compositions>

Examples 4 to 6, Comparative Example 1

The components shown in Table 1 were mixed together and dissolved to prepare a series of positive resist compositions.

TABLE 1

| | Component (A) | Component (B) | Component (D) | Component (S) |
|---|---|---|---|---|
| Comparative example 1 | (A)-1 [100] | (B)-1 [18.9] | (D)-1 [1.5] | (S)-1 [4900] |
| Example 4 | (A)-2 [100] | (B)-1 [18.9] | (D)-1 [1.5] | (S)-1 [4900] |
| Example 5 | (A)-2 [100] | (B)-2 [13.6] | (D)-1 [1.5] | (S)-1 [4900] |
| Example 6 | (A)-2 [100] | (B)-3 [28.5] | (D)-1 [1.5] | (S)-1 [4900] |

In Table 1, the reference symbols have the meanings shown below. Further, the numerical values in brackets [ ] indicate the amount (in parts by weight) of the component added.

(A)-1: the aforementioned polymeric compound (A3-1)
(A)-2: the aforementioned polymeric compound (A1-11-1)
(B)-1: an acid generator represented by chemical formula (B1) shown below
(B)-2: an acid generator represented by chemical formula (B2) shown below
(B)-3: an acid generator represented by chemical formula (B3) shown below

[Chemical Formula 91]

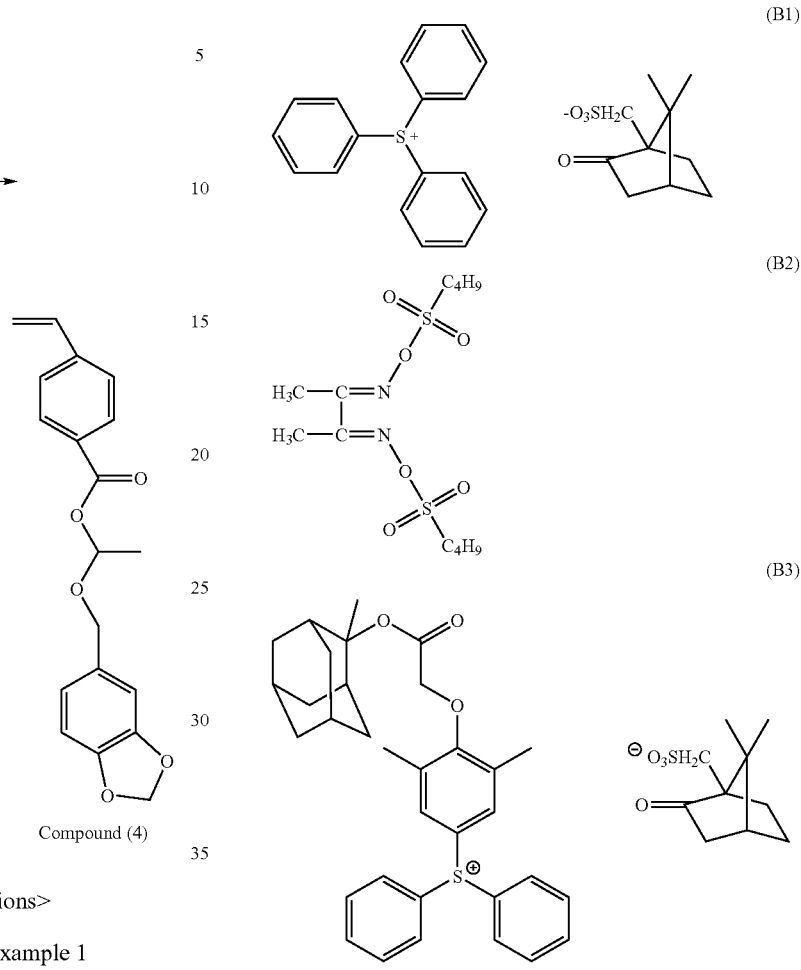

(D)-1: tri-n-octylamine
(S)-1: a mixed solvent of PGMEA/PGME=6/4 (weight ratio)

<Evaluation of Lithography Properties>

Each of the thus obtained positive resist compositions was evaluated for sensitivity, resolution, line width roughness (LWR), and resist pattern shape. The results are shown in Table 2.

[Formation of Resist Pattern]

Using a spinner, each of the above positive resist compositions was applied uniformly onto an 8-inch silicon substrate that had been surface-treated with hexamethyldisilazane (HMDS) for 36 seconds at 90° C., and a prebake (PAB) was then conducted for 60 seconds at the temperature shown in Table 2, thereby forming a resist film (film thickness: 60 nm).

This resist film was subjected to direct patterning with an electron beam lithography apparatus HL-800D (VSB) (manufactured by Hitachi Ltd.) at an accelerating voltage of 70 kV, and was then subjected to a post exposure bake treatment (PEB) for 60 seconds at the temperature shown in Table 2, followed by alkali development for 60 seconds at 23° C. in a 2.38% by weight aqueous solution of tetramethylammonium hydroxide (TMAH) (product name: NMD-3, manufactured by Tokyo Ohka Kogyo Co., Ltd.). The resist film was then rinsed for 15 seconds with pure water, thus forming a line and space pattern (hereafter referred to as an "L/S pattern").

[Evaluation of Sensitivity]

In the above resist pattern formation, the optimum exposure dose Eop ($\mu$C/cm$^2$) at which an L/S pattern having a line width of 100 nm and a pitch of 200 nm was formed was determined.

[Evaluation of Resolution]

The critical resolution (nm) at the above Eop value was determined.

[Evaluation of Line Width Roughness (LWR)]

For each of the L/S patterns having a line width of 100 nm and a pitch of 200 nm formed at the Eop value described above, the line width was measured at 5 points along the lengthwise direction of the line using a measuring scanning electron microscope (SEM) (product name: S-9220, manufactured by Hitachi, Ltd.), and from these results, the value of 3 times the standard deviation (s) (namely, 3s) was calculated as an indicator (nm) of the LWR.

The smaller the value of 3s, the lower the level of roughness in the line width, indicating an L/S pattern of more uniform width.

[Evaluation of Resist Pattern Shape]

Each of the L/S patterns having a line width of 100 nm and a pitch of 200 nm formed at the Eop value described above was inspected using a scanning electron microscope (SEM), and the cross-sectional shape of the pattern and the shape of the pattern when viewed from directly above were evaluated.

TABLE 2

| | PAB (° C.) | PEB (° C.) | Eop ($\mu$C/cm$^2$) | Critical resolution (nm) | LWR (nm) | Resist pattern shape |
|---|---|---|---|---|---|---|
| Comparative example 1 | 100 | 100 | 24 | 80 | 23.0 | T-top |
| Example 4 | 100 | 100 | 24 | 50 | 14.0 | rectangular |
| Example 5 | 100 | 100 | 10 | 50 | 15.4 | rectangular |
| Example 6 | 100 | 100 | 38 | 60 | 18.0 | rectangular |

From the results in Table 2 it was evident that, compared with the positive resist composition of comparative example 1, the positive resist compositions according to the present invention from examples 4 to 6 exhibited superior resolution.

Further, it was also confirmed that, compared with the resist pattern formed using the positive resist composition of comparative example 1, the resist patterns formed using the positive resist compositions according to the present invention from examples 4 to 6 exhibited a more favorable pattern shape, with reduced LWR and a high degree of rectangularity. Furthermore, compared with comparative example 1, the positive resist compositions of examples 4 to 6 were more resistant to pattern collapse.

What is claimed is:

1. A positive resist composition comprising a base component (A) which exhibits increased solubility in an alkali developing solution under action of acid and an acid generator component (B) which generates acid upon exposure, wherein
said base component (A) comprises a polymeric compound (A1) comprising a structural unit (a0) containing an acid-dissociable, dissolution-inhibiting group, and said structural unit (a0) is a structural unit represented by general formula (a0-1') shown below:

[Chemical Formula 1]

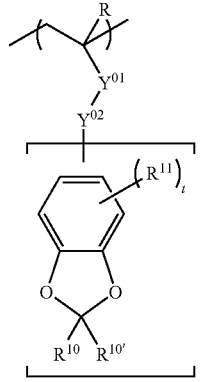

(a0-1')

wherein R represents a hydrogen atom, an alkyl group of 1 to 5 carbons or a halogenated alkyl group of 1 to 5 carbons, Y$^{01}$ represents a divalent organic group that becomes an alkali-soluble group upon cleavage of a bond to Y$^{02}$ under action of an acid, Y$^{02}$ represents a single bond or a divalent linking group, which substitutes 1 hydrogen atom of a group within brackets [ ] of formula (a0-1') that is derived from either a 1,3-benzodioxole or a derivative thereof, R$^{11}$ represents a hydrocarbon group of 1 to 30 carbon atoms that may have a substituent, t represents an integer of 0 to 3, and in those cases where t is 2 or 3, a plurality of R$^{11}$ groups may be bonded together to form a ring, or may be bonded to a benzene ring to form an aromatic ring, R$^{10}$ may be a hydrogen atom or an alkyl group of 1 to 5 carbon atoms which may have a substituent, R$^{10'}$ represents a hydrogen atom or an alkyl group of 1 to 5 carbon atoms which may have a substituent, and R$^{10}$ and R$^{10'}$ may be bonded together to form a ring.

2. The positive resist composition according to claim 1, wherein Y$^{02}$ within said general formula (a0-1') is a divalent linking group comprising a group represented by general formula (p11') shown below:

[Chemical Formula 2]

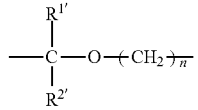

(p11')

wherein each of R$^{1'}$ and R$^{2'}$ independently represents a hydrogen atom or an alkyl group of 1 to 5 carbon atoms, and n represents an integer of 0 to 3.

3. The positive resist composition according to claim 1, wherein said polymeric compound (A1) further comprises a structural unit (a5) derived from a hydroxystyrene.

4. The positive resist composition according to claim 3, wherein said structural unit (a5) is a structural unit represented by general formula (a5-1) shown below:

[Chemical Formula 3]

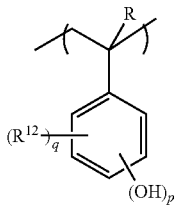

(a 5-1)

wherein R represents a hydrogen atom, an alkyl group of 1 to 5 carbon atoms or a halogenated alkyl group of 1 to 5 carbon atoms, $R^{12}$ represents a halogen atom, an alkyl group of 1 to 5 carbon atoms or a halogenated alkyl group of 1 to 5 carbon atoms, p represents an integer of 1 to 3, and q represents an integer of 0 to 4, provided that p+q is an integer of 1 to 5.

5. The positive resist composition according to claim 1, further comprising a nitrogen-containing organic compound (D).

6. A method of forming a resist pattern, comprising applying a positive resist composition according to claim 1 onto a substrate to form a resist film, subjecting said resist film to exposure, and subjecting said resist film to alkali developing to form a resist pattern.

7. A polymeric compound comprising a structural unit represented by general formula (a0-1') shown below:

[Chemical Formula 4]

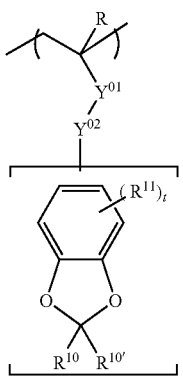

(a 0-1')

wherein R represents a hydrogen atom, an alkyl group of 1 to 5 carbon atoms or a halogenated alkyl group of 1 to 5 carbon atoms, $Y^{01}$ represents a divalent organic group that becomes an alkali-soluble group upon cleavage of a bond to $Y^{02}$ under action of acid, $Y^{02}$ represents a single bond or a divalent linking group, which substitutes one hydrogen atom of a group within brackets [ ] of formula (a0-1') that is derived from either a 1,3-benzodioxole or a derivative thereof, $R^{11}$ represents a hydrocarbon group of 1 to 30 carbon atoms which may have a substituent, t represents an integer of 0 to 3, and in those cases where t is 2 or 3, a plurality of $R^{11}$ groups may be bonded together to form a ring, or may be bonded to a benzene ring to form an aromatic ring, $R^{10}$ represents a hydrogen atom or an alkyl group of 1 to 5 carbon atoms which may have a substituent, $R^{10'}$ represents a hydrogen atom or an alkyl group of 1 to 5 carbon atoms which may have a substituent, and $R^{10}$ and $R^{10'}$ may be bonded together to form a ring.

8. The polymeric compound according to claim 7, wherein $Y^{02}$ within said general formula (a0-1') is a divalent linking group comprising a group represented by general formula (p11') shown below:

[Chemical Formula 5]

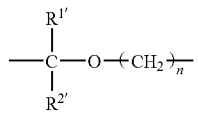

(p 11')

wherein each of $R^{1'}$ and $R^{2'}$ independently represents a hydrogen atom or an alkyl group of 1 to 5 carbon atoms, and n represents an integer of 0 to 3.

9. The polymeric compound according to claim 7, further comprising a structural unit (a5) derived from a hydroxystyrene.

10. The polymeric compound according to claim 9, wherein said structural unit (a5) is a structural unit represented by general formula (a5-1) shown below:

[Chemical Formula 6]

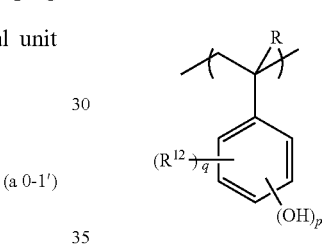

(a 5-1)

wherein R represents a hydrogen atom, an alkyl group of 1 to 5 carbon atoms or a halogenated alkyl group of 1 to 5 carbon atoms, $R^{12}$ represents a halogen atom, an alkyl group of 1 to 5 carbon atoms or a halogenated alkyl group of 1 to 5 carbon atoms, p represents an integer of 1 to 3, and q represents an integer of 0 to 4, provided that p+q is an integer of 1 to 5.

11. A compound represented by general formula (a0-1-1) shown below:

[Chemical Formula 7]

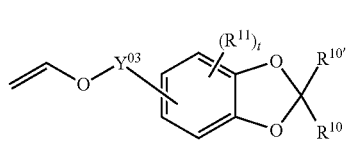

(a 0-1-1)

wherein $Y^{03}$ represents a single bond or a divalent linking group, $R^{11}$ represents a hydrocarbon group of 1 to 30 carbon atoms which may have a substituent, t represents an integer of 0 to 3, and in those cases where t is 2 or 3, a plurality of $R^{11}$ groups may be bonded together to form a ring, or may be bonded to a benzene ring to form an aromatic ring, $R^{10'}$ represents a hydrogen atom or an alkyl group of 1 to 5 carbon atoms which may have a substituent, $R^{10'}$ represents a hydrogen atom or an alkyl group of 1 to 5 carbon atoms which may have a substituent, and $R^{10}$ and $R^{10'}$ may be bonded together to form a ring.

12. A compound represented by a general formula (a0-1-1-1) shown below:

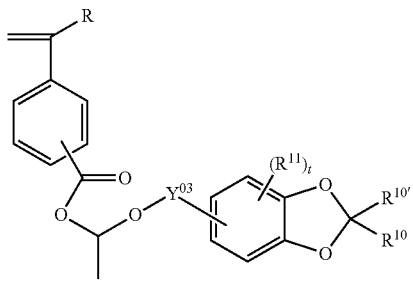

(a0-1-1-1)

wherein R represents a hydrogen atom, an alkyl group of 1 to 5 carbon atoms or a halogenated alkyl group of 1 to 5 carbon atoms, $Y^{03}$ represents a single bond or a divalent linking group, $R^{11}$ represents a hydrocarbon group of 1 to 30 carbon atoms which may have a substituent, t represents an integer of 0 to 3, and in those cases where t is 2 or 3, a plurality of $R^{11}$ groups may be bonded together to form a ring, or may be bonded to a benzene ring to form an aromatic ring, $R^{10}$ represents a hydrogen atom or an alkyl group of 1 to 5 carbon atoms which may have a substituent, $R^{10'}$ represents a hydrogen atom or an alkyl group of 1 to 5 carbon atoms which may have a substituent, and $R^{10}$ and $R^{10'}$ may be bonded together to form a ring.

* * * * *

UNITED STATES PATENT AND TRADEMARK OFFICE
CERTIFICATE OF CORRECTION

PATENT NO. : 8,268,530 B2
APPLICATION NO. : 12/762715
DATED : September 18, 2012
INVENTOR(S) : Yoshiyuki Utsumi and Jun Iwashita It is certified that error appears in the above-identified patent and that said Letters Patent is hereby corrected as shown below:

Title page, between the filing date (22) and the Prior Publication Data (65), please insert --(30) Foreign Application Priority Data Apr. 24, 2009 (JP)   P2009-106711--.

In the Specifications:

In Column 1, Line 39, Change "Wine" to --i-line--.

In Column 7, Line 42, Change "and" to --and $R^{20}$--.

In Column 17, Line 40, Change "$R^{H}$" to --$R^{11}$--.

In Column 23, Line 6, Change "α-position," to --o-position,--.

In Column 23, Line 45, Change " $(-O-C(R^{1\prime})(R^{2\prime})-O-Q^{0}-R^{20})$ " to --$(-O-C(R^{1\prime})(R^{2\prime})-O-Q^{0}-R^{20})$--.

In Column 23, Lines 55-56, Change " $(-O-C(R^{1\prime})(R^{2\prime})-O-Q^{0}-R^{20}).$ " to --$(-O-C(R^{1\prime})(R^{2\prime})-O-Q^{0}-R^{20}).$--.

In Column 110, Line 24 (Approx.), Change "tetraclyclododecane" to --tetracyclododecane.--.

In Column 110, Line 33 (Approx.), Change "group)" to --group).--.

In Column 121, Line 40 (Approx.), Change "carbon" to --5 carbon--.

Signed and Sealed this
Twenty-eighth Day of May, 2013

Teresa Stanek Rea
*Acting Director of the United States Patent and Trademark Office*

CERTIFICATE OF CORRECTION (continued)

In Column 132, Line 22, Change "preferable" to --preferable.--.

In Column 132, Line 44, Change "—C(=O)—," to -- —C(=O)—, —O—C(=O)—O—,--.

In Column 133, Line 6, Change "CH₂CH₂CH₂-," to -- -CH₂CH₂CH₂-,--.

In Column 134, Line 7, Change "heptafluoropropanesulfonate," to --heptafluoropropanesulfonate--.

In Column 142, Lines 23-24,

Change "
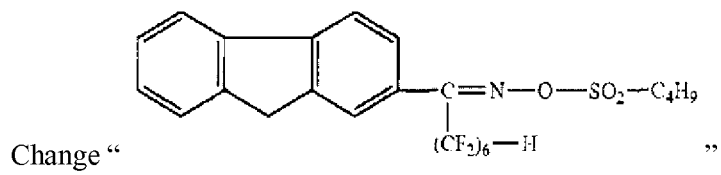
"

to --
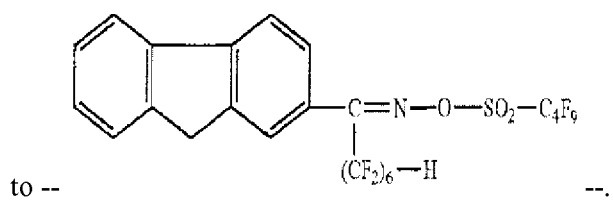
--.

In Column 142, Lines 26, 27,

Change "
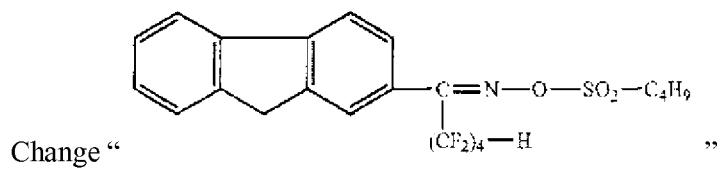
"

to --
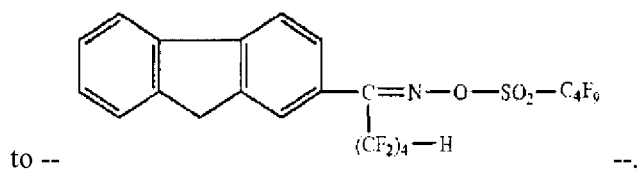
--.

In Column 142, Lines 38-39, Change "his(2,4-dimethylphenylsulfonyl)diazomethane." to --bis(2,4-dimethylphenylsulfonyl)diazomethane.--.

In Column 147, Line 52 (Approx.), Change "as long at" to --as long as--.

In the Claims:

In Column 161, Line 65, In Claim 1, change "group, and" to --group,--.

In Column 164, Line 62, In Claim 11, change "$R^{10'}$" to --$R^{10}$--.